US010565440B2

(12) United States Patent
Wee et al.

(10) Patent No.: US 10,565,440 B2
(45) Date of Patent: Feb. 18, 2020

(54) DEVICE FOR RECOGNIZING ANIMAL'S IDENTITY BY USING ANIMAL NOSE PRINTS

(71) Applicant: ISCILAB CORPORATION, Seoul (KR)

(72) Inventors: Nam Sook Wee, Seoul (KR); Stephanie Sujin Choi, Seoul (KR); Haeng Moon Kim, Gwacheon-si (KR); Hyeong In Choi, Seoul (KR)

(73) Assignee: ISCILAB CORPORATION, Seoul (KR)

( * ) Notice: Subject to any disclaimer, the term of this patent is extended or adjusted under 35 U.S.C. 154(b) by 24 days.

(21) Appl. No.: 16/185,324

(22) Filed: Nov. 9, 2018

(65) Prior Publication Data

US 2019/0080159 A1 Mar. 14, 2019

Related U.S. Application Data

(62) Division of application No. 14/893,043, filed as application No. PCT/KR2014/004487 on May 20, 2014, now Pat. No. 10,268,880.

(30) Foreign Application Priority Data

May 22, 2013 (KR) .................. 10-2013-0057667

(51) Int. Cl.
*A01K 29/00* (2006.01)
*A01K 15/04* (2006.01)
(Continued)

(52) U.S. Cl.
CPC ........ *G06K 9/00362* (2013.01); *A01K 11/006* (2013.01); *A01K 15/04* (2013.01);
(Continued)

(58) Field of Classification Search
CPC .. G06K 9/00362; G06K 9/00885; A61D 3/00; A61D 2003/003; A61D 2003/006;
(Continued)

(56) References Cited

U.S. PATENT DOCUMENTS 4,286,547 A * 9/1981 Nuwbauer et al. .... A01K 15/04
119/815
4,693,212 A * 9/1987 Black ....................... A61D 3/00
119/755

(Continued)

FOREIGN PATENT DOCUMENTS

JP 11-045330 A 2/1999
JP 2001-148957 A 6/2001
(Continued)

OTHER PUBLICATIONS

Search Report, dated Oct. 27, 2014, for International Application No. PCT/KR2014/004487.
(Continued)

*Primary Examiner* — Andrew W Johns
(74) *Attorney, Agent, or Firm* — LRK Patent Law Firm

(57) ABSTRACT

The present invention relates to an animal recognition apparatus using nose patterns, which includes a body stabilizer unit to minimize movement and resistance of an animal during an optimal nose pattern image acquisition, wherein the acquired nose pattern images are used to biometrically identify the animal.

37 Claims, 60 Drawing Sheets

(51) Int. Cl.
*G06K 9/00* (2006.01)
*A61B 5/1171* (2016.01)
*G06T 7/00* (2017.01)
*A01K 11/00* (2006.01)
*G06T 7/11* (2017.01)
*G06K 9/46* (2006.01)
*A61B 5/00* (2006.01)

(52) U.S. Cl.
CPC ............ *A01K 29/00* (2013.01); *A61B 5/0077* (2013.01); *A61B 5/1171* (2016.02); *A61B 5/6819* (2013.01); *A61B 5/702* (2013.01); *G06K 9/00885* (2013.01); *G06K 9/4604* (2013.01); *G06T 7/0012* (2013.01); *G06T 7/11* (2017.01); *A61B 5/0059* (2013.01); *A61B 5/726* (2013.01); *A61B 5/7257* (2013.01); *A61B 2503/40* (2013.01); *A61B 2562/0242* (2013.01); *G06K 9/00221* (2013.01)

(58) Field of Classification Search
CPC ...... A01K 1/06; A01K 1/0606; A01K 1/0613; A01K 1/062; A01K 1/064; A01K 15/04
See application file for complete search history.

(56) References Cited

U.S. PATENT DOCUMENTS

| | | | |
|---|---|---|---|
| 5,690,365 A | 11/1997 | Fascenelli, Jr. et al. | 283/67 |
| 5,799,617 A * | 9/1998 | Long et al. | A01K 15/00 119/712 |
| 6,003,473 A | 12/1999 | Printz | 119/859 |
| D458,421 S | 6/2002 | Wasserman et al. | D30/155 |
| 6,568,354 B1 | 5/2003 | Wasserman et al. | 119/859 |
| D491,323 S | 6/2004 | Wilcox | D30/155 |
| D494,326 S | 8/2004 | Long | D30/155 |
| 6,845,382 B2 | 1/2005 | Meadows | 707/104.1 |
| 7,230,539 B2 | 6/2007 | Klein | 340/573.1 |
| 2007/0079766 A1* | 4/2007 | Park | A01K 13/001 119/674 |
| 2011/0006172 A1* | 1/2011 | Sargent | A61D 3/00 248/156 |

FOREIGN PATENT DOCUMENTS

| | | |
|---|---|---|
| JP | 2003-346148 A | 12/2003 |
| JP | 2007-135501 A | 6/2007 |
| JP | 4190209 B2 | 12/2008 |
| KR | 10-2002-0066771 A | 8/2002 |
| KR | 10-0414606 B1 | 12/2003 |
| KR | 10-2004-0006822 A | 1/2004 |
| KR | 10-2004-008072 A | 1/2004 |
| KR | 20-0337597 Y1 | 1/2004 |
| KR | 10-0479937 B1 | 3/2005 |
| KR | 10-0485922 B1 | 4/2005 |

OTHER PUBLICATIONS

Written Opinion, dated Oct. 27, 2014, for International Application No. PCT/KR2014/004487.

International Preliminary Report on Patentability, dated Nov. 24, 2015, for International Application No. PCT/KR2014/004487.

\* cited by examiner

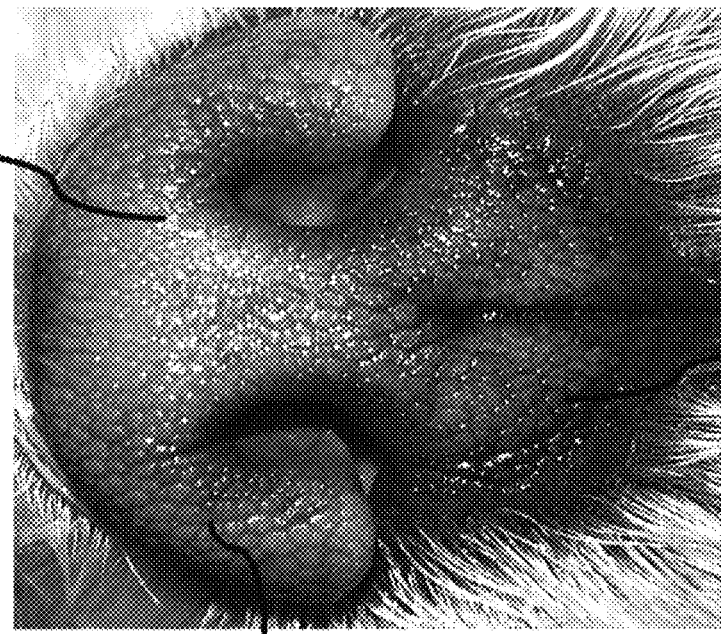
FIG. 4

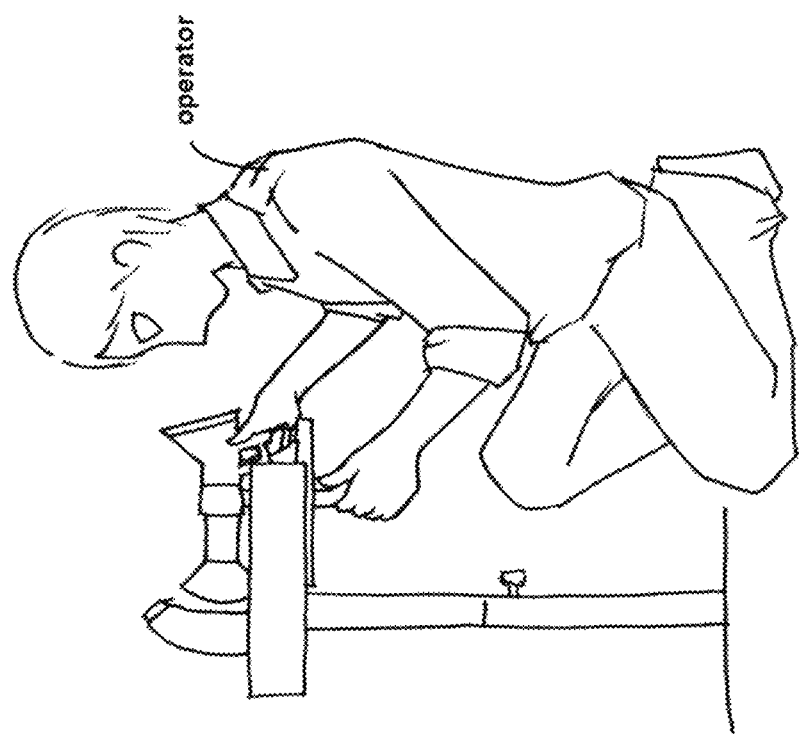
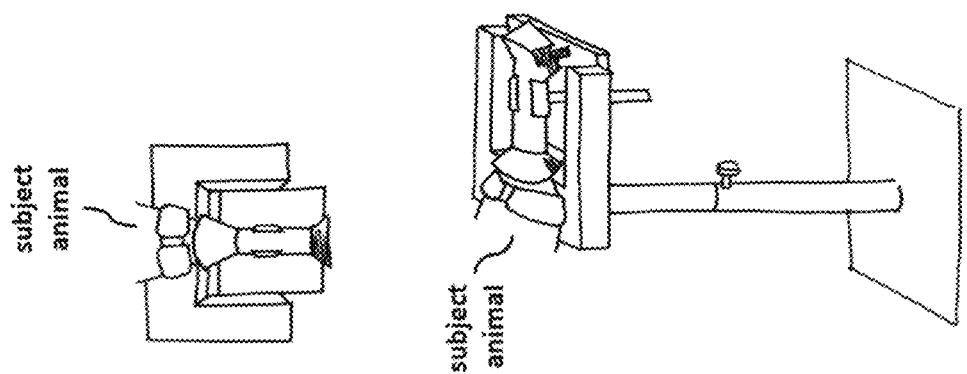
FIG. 6

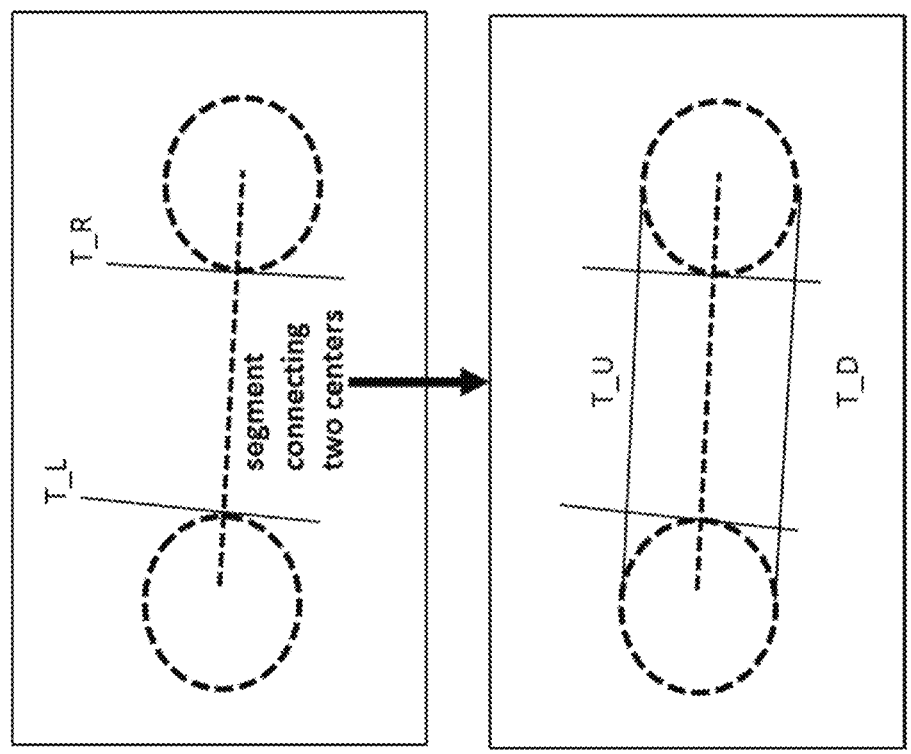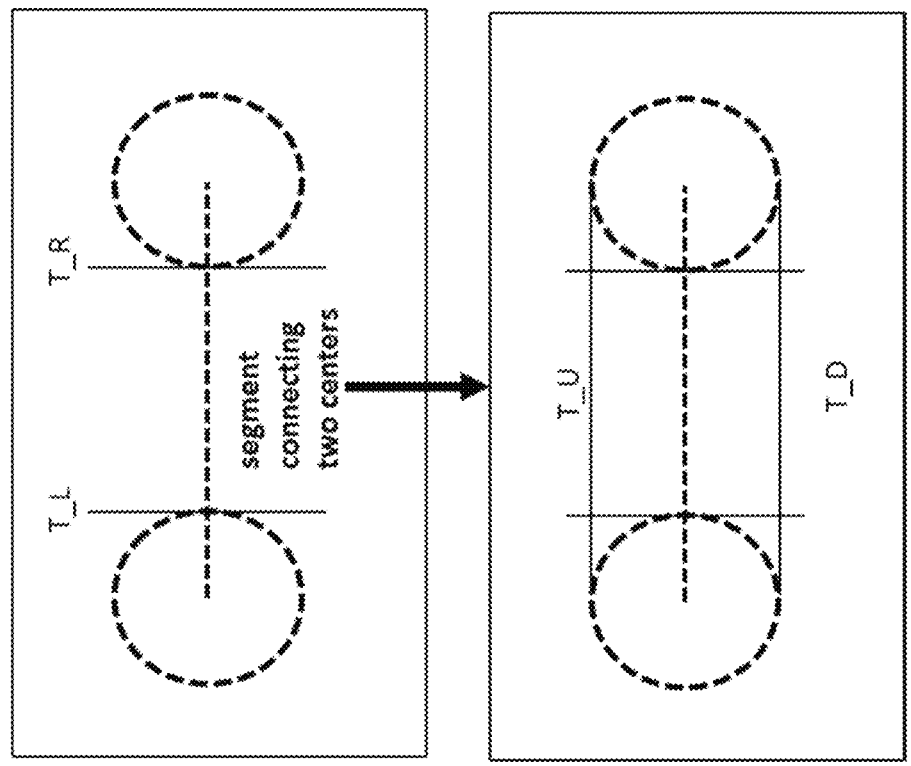
FIG. 44

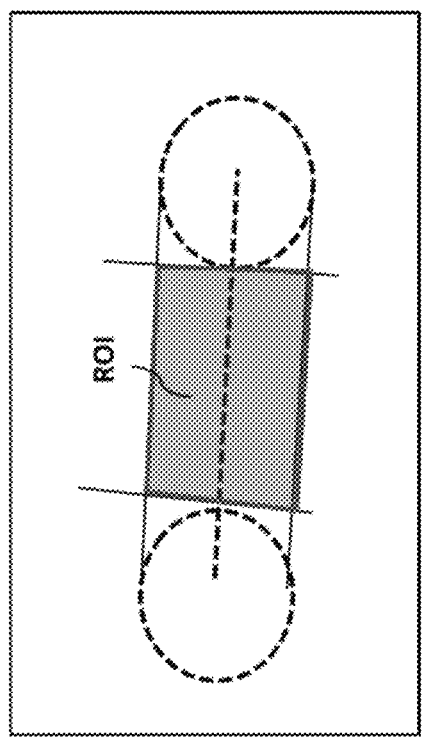
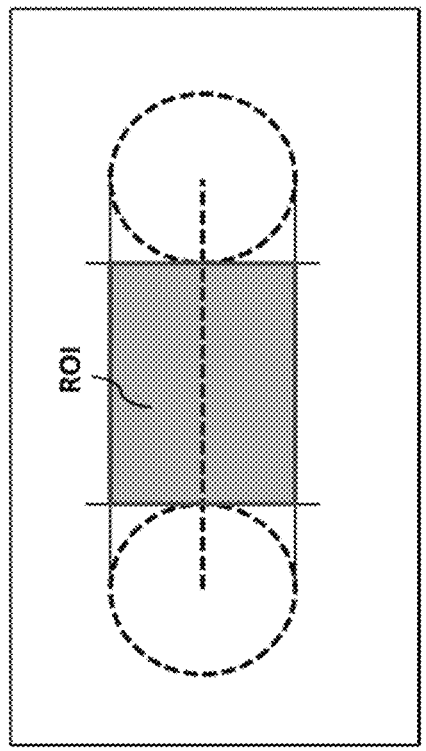
FIG. 45

DEVICE FOR RECOGNIZING ANIMAL'S IDENTITY BY USING ANIMAL NOSE PRINTS

CROSS REFERENCE TO RELATED APPLICATIONS

This application is a division of U.S. patent application Ser. No. 14/893,043, filed May 23, 2016, which was a U.S. National Phase entry from International Application No. PCT/KR2014/004487, filed May 20, 2014, and claimed priority to Korean Patent Application No. 10-2013-0057667, filed May 22, 2013, the disclosures of which are incorporated by reference in their entireties herein.

BACKGROUND

1. Field of the Invention

The present invention relates to an apparatus of an animal recognition using nose patterns, and particularly to an apparatus of an animal recognition comprising a body stabilizer unit to minimize movement of the subject animal for optimal nose pattern image acquisition, wherein the acquired nose pattern image is used to biometrically identify individual animals.

2. Description of Related Art

Animal identification has been around for thousands of years as indicated in the Code of Hammurabi dating back to about 1754 BC. At the time, the preferred method of marking a body part (branding) was used primarily to prevent the theft of valuable animal assets like horses. Nowadays, in addition to theft prevention and general proof of ownership, animal identification serves an important role in the production management and disease control of livestock, the management of endangered and protected species, as well as the essential inspection process of animal imports and exports. Globalization has increased the worldwide demand for animals for a variety of purposes, ranging from meat consumption to collecting exotic pets.

Accordingly, animals are being mass-bred and exported, but this has resulted in the spread of epidemics like the mad cow disease, which had previously been limited to specific farms or regions. Therefore, each and every state including the UN has sought to employ an effective and reliable animal tracking and identification system to manage the risks involved in the domestic and international production, distribution, and transportation of animals. More recently, various studies are under progress in an attempt to improve the traditional methods and systems by incorporating new developments in information technology.

Conventional methods of animal (livestock) management include: ear notching, primarily for pigs; plastic and bar-coded ear tagging, primarily for cows and sheep; number designation on neck chains for cows; freeze branding numbers or letters using metal cooled with liquid nitrogen, dry ice, or alcohol; paint branding; and tattooing. These procedures require needless or painful modifications or attachments to the animal's body, putting animals and the necessary professional handlers in potential harm's way. Even when executed without complications, these external markers or labels can be difficult to identify in the dark, or become damaged by the physical activities of the animal or by human acts of vandalism.

The alternatives to the above methods largely fall under two categories: electronic and biometric identification. Electronic identification requires the use of an electronic ear tag, injectable transponder, or a ruminal blouse to contain and be scanned for the desired information. However, unintentional damage to or intentional tampering of the microchip or antenna, as well as the unavailability of an appropriate scanning device can make identification impossible. Also, some studies have found that the material surrounding the microchip and antenna unit can cause tumors or tissue necrosis in the animals, providing significant reasons for concern among owners of companion and livestock animals.

The second alternative, on the other hand, is more promising. Biometric identification relies on the intrinsic characteristics unique to individuals without the necessity of invasive procedures and, unlike the traditional methods or microchip identification, the biometric data of an animal cannot be doctored. Current ongoing studies are seeking to make progress in animal iris and retina imaging, DNA analysis, and nose pattern imaging. However, the first three have not been developed enough yet to be practically applicable in the field.

As such, some limited efforts were made in the late 20th century, when the uniqueness of individual nose patterns on certain livestock became widely accepted, to obtain and compare nose patterns on individual cows or sheep in the same way fingerprints were initially collected: by cleaning the surface of the nose followed by obtaining ink impressions. However, this method is rather primitive and has consistently presented many issues in terms of practicality and accuracy; depending on the inexperience of the administrator there were unwanted ink bleeds or distortions on the print due to uneven application of pressure, often resulting in disparate prints of the same nose even when performed by a single individual. Also, a healthy animal nose is meant to maintain moisture through natural nasal irrigation or deliberate licking, which means each ink transfer is a laborious process.

Korean Laid-open Patent Publication No. 10-2004-0008072 presents the technical configuration of portable information terminal for controlling cattle, while Korean Laid-open Patent Publication No. 10-2004-0006822 discusses a method of remote bovine identification and health monitoring using previously scanned nose pattern data via the internet or a network. However, due to their reliance on the traditional ink impression method before scanning the resulting ink print to obtain the nose pattern image, the limitations in accuracy and the potential for aberration arising from human error during the process are prevalent. Moreover, the above methods cater only to bovine subjects and thus are inapplicable to animals with differently sized, shaped and patterned noses.

Korean Laid-open Patent Publication No. 10-2002-00066771 presents the technical configuration of a system of canine identification using nose pattern data through a communication network, but it does not specify the method of obtaining such data.

On the other hand, U.S. patent application Ser. No. 10/770,120 does disclose a technical construction of obtaining the nose pattern images of canine pets. The pattern data are collected by either macro shooting with a specialized camera to compensate for the difficulty in focus adjustments while manually holding the subject animal's muzzle, or by getting an impression of the nose—similar to the traditional method—using some pliable plastic coated with ink or a paper or card comprising two different layers of chemicals in place of ink.

With the macro shooting approach, size and spacing distortion in the nose pattern image can occur; and, as mentioned in the said patent as a point of concern, it is difficult for an average person operating a conventional digital camera or camcorder to make precise focus adjustments. Another method described in the above patent uses a polaroid camera where the focus is set by converging two irradiating beams, but it is highly likely that during the process the light will agitate and cause the canine subject to resist the restraint or move and impede the photography. Moreover, out in the field it is difficult to predict each subject animal's sensitivity or reaction to deliberate lighting and often smaller dogs are quite intimidated by the camera itself, both adding to the difficulty. Then there is also the problem of getting unwanted light reflections off of the moisture normally present on the nose skin when direct illumination is used during image capture.

The latter approach using contact impression is identical in its practice as well as limitations to the traditional inking method. In addition, a dog's tendency to actively keep their noses wet through licking when the moisture is deliberately wiped off means a hurried effort is required to obtain a clean impression, while the size and shape specification of the equipment limits the appropriate subjects to canine breeds.

Another prior invention related to the present one is the Japanese Laid-open Patent Publication 2003-346148, which prescribes that a glass frame or some other transparent material be pressed against a cow's nose to obtain the image with a digital camera for analysis. However, this approach is also similar to the traditional ink impression method wherein a transparent frame has merely replaced the decal paper, and presents the same distortion issues that result from direct contact with the nose as well as its limitation to bovine subjects.

Thus follows that there is a demand for a streamlined animal identification system that does not require professional operators, can overcome the aforementioned encumbrances, and can be easily and economically applied to small farm or livestock environments, animal registration systems, and even import and export inspections.

SUMMARY

An object of the present invention is the acquisition and recognition of animal nose patterns without making direct physical contact with the nose.

Another object of the present invention is the acquisition of nose pattern images fit for recognition by utilizing a body stabilizer unit that minimizes obstructive movements in a subject animal that behaves uncooperatively out of fear or aggression toward the image acquisition equipment or the operator, and maintains the ideal frontal capturing angle on the subject's nose.

Yet another object of the present invention is the acquisition of good quality nose pattern images with the use of a body stabilizer unit designed to accommodate animals of different sizes and species.

Yet another object of the present invention is the acquisition of high quality nose pattern images by utilizing indirect illumination of appropriate wavelength regions applied through a light conduit subunit, light diffuser subunit, and spacer onto the subject's nose to prevent unwanted light reflections that may come off the layer of moisture on the nose surface of subject animals.

Yet another object of the present invention is the acquisition of high quality nose pattern images through the use of an image capture unit that is modifiable to accommodate subject animals of different species.

Yet another object of the present invention is to enable non-professional users to acquire nose pattern images fit for recognition with ease using the image acquisition unit.

Yet another object of the present invention is to make possible the identification of any animal with a discernible nose pattern, regardless of species- or breed-specific pattern types.

Yet another object of the present invention is to make identification possible regardless of the presence of extraneous physiological or environmental phenomena, such as moisture, hair, or dust of the subject animal's nose surface.

Yet another object of the present invention is to make identification possible despite reasonable variations in the image capturing angle.

Yet another object of the present invention is to generate a universal nose code irrelevant species or breed for use in identification.

Yet another object of the present invention is to use the most appropriate method of verification or identification for particular species or breeds.

Yet another object of the present invention is to increase the accuracy rate of recognition for each species of subject animals by comparing and matching previously stored nose pattern images to those newly obtained using the proper body stabilizer unit, image acquisition unit and image recognition unit.

A technical solution of the present invention is to provide an animal recognition apparatus comprising a body stabilizer unit, image acquisition unit, and image recognition unit.

Another technical solution of the present invention is to provide an animal recognition method comprising the following steps: selection of the appropriate body stabilizer for the species or breed of the subject animal, stabilization of the subject animal's body using the selected body stabilizer unit; acquisition of the nose pattern image by the image acquisition unit; storing of the acquired nose pattern image; generation of a nose pattern code from the acquired image; enrollment of the generated nose pattern code; and verification or identification of the subject animal by matching the newly obtained nose pattern code with previously enrolled nose codes.

Yet another technical solution of the present invention is to provide an animal recognition method comprising the following steps: acquisition of a nose pattern image using the body stabilizer unit and image acquisition unit; setting a region of interest (ROI) in the acquired nose pattern image, raw or processed; generation of a nose pattern code from the ROI or standardized ROI; enrollment of the newly generated nose pattern code; and verification or identification by determining the distance between the newly generated nose pattern code and previously enrolled nose codes.

Advantageous Effects

The present invention has an advantageous effect in the fast and accurate recognition of animals through the acquisition of nose patterns without making direct physical contact with the nose.

Another effect of the present invention is the acquisition of nose pattern images fit for recognition by utilizing a body stabilizer unit that minimizes obstructive movements in a subject animal that behaves uncooperatively out of fear or aggression toward the image acquisition equipment or the operator, and maintains the ideal frontal capturing angle on the subject's nose.

Yet another effect of the present invention is the acquisition of good quality nose pattern images with the use of a body stabilizer unit designed to accommodate animals of different sizes and species.

Yet another effect of the present invention is the acquisition of high quality nose pattern images by utilizing indirect illumination of appropriate wavelength regions applied through a light conduit subunit, light diffuser subunit, and spacer onto the subject's nose to prevent unwanted light reflections that may come off the layer of moisture on the nose surface of subject animals.

Yet another effect of the present invention is the acquisition of high quality nose pattern images through the use of an image capture unit that is modifiable to accommodate subject animals of different species.

Yet another effect of the present invention is to enable non-professional users to acquire nose pattern images fit for recognition with ease using the image acquisition unit.

Yet another effect of the present invention is to make possible the identification of any animal with a discernible nose pattern, regardless of species- or breed-specific pattern types.

Yet another effect of the present invention is to make identification possible regardless of the presence of extraneous physiological or environmental phenomena, such as moisture, hair, or dust of the subject animal's nose surface.

Yet another effect of the present invention is to make identification possible despite reasonable variations in the image capturing angle.

Yet another effect of the present invention is to generate a universal nose code irrelevant species or breed for use in identification.

Yet another effect of the present invention is the use of the most appropriate method of verification or identification for the particular species or breed.

Yet another effect of the present invention is to increase the accuracy rate of recognition for each species of subject animals by comparing and matching previously stored nose pattern images to those newly obtained using the proper body stabilizer unit, image acquisition unit and image recognition unit.

BRIEF DESCRIPTION OF THE DRAWINGS

FIG. 4 is a photograph of obstructive light reflections from the moisture naturally present on the surface of the nose of the subject animals.

FIG. 6 is a presentation of the animal recognition apparatus in FIG. 5 shown from different angles.

FIG. 44 is a diagram illustrating the method of obtaining the region on the opposite side of each nostril, which is located in the exterior of the approximated curves (circle/ellipse).

FIG. 45 is a diagram illustrating the method of selecting the rectangular area between the approximation curves (circle/ellipse) as the region of interest.

DETAILED DESCRIPTION OF THE INVENTION

Figure 1:
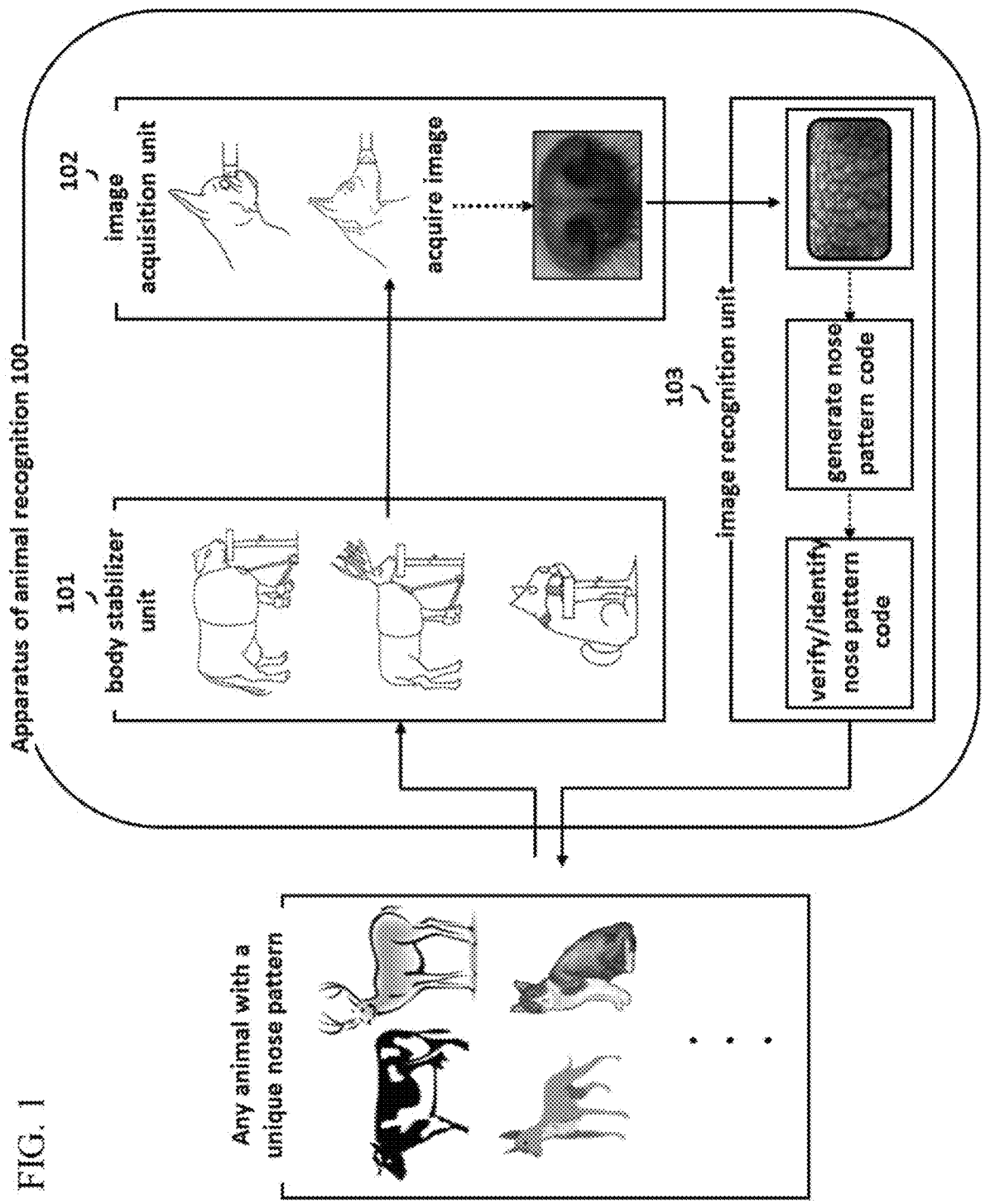
FIG. 1 is a schematic diagram of the embodiment of the animal recognition apparatus described in the present invention.

The following section describes the configuration and operation of the present invention, wherein the accompanying diagrams merely provide examples of one or more possible embodiments and do not limit the technical concept or its core components and applications. Therefore, for those with the skill and knowledge in the field of the present invention should be able to apply various changes and modifications to the presently described embodiment of an animal recognition apparatus without deviating from the core concept.

In explaining the components of the present invention, such terms as A, B, (a), (b) and the like can used. These are simply intended to distinguish one component from another, and not a reflection of the specific nature, order, or sequence of said components. When a component is described to be "connected to," "included in," or "configuring" another, they may be directly connected or coupled, but it should be understood that some other component could also be "connected to," "included in," or "configuring" each of the said components.

Also, for ease of understanding, when one component is shown in multiple figures it will be given a different reference numeral each time to correspond to the rest of the diagram.

Furthermore, the present invention seeks to distinguish between the terms Verification, Identification, and Recognition. Specifically, Verification refers to one-to-one (1:1) matching, Identification or Searching refers to one-to-many (1:n) matching, and Recognition encompasses both the Verification and Identification processes.

Several representative species—the cow, deer, dog and cat—with nose patterns have been selected here to illustrate the utilization of the present invention; and for whenever the method or apparatus is universally applicable, a single species is shown in the example for sufficient understanding. The implication is that the application of the present invention pertains not only to the specifically mentioned animals, but any and all species with distinct nose patterns.

In the present invention, nose pattern relates to how the beads and grooves form geometric patterns on the nose surface, and it should be noted that the size and intricacy of the patterning can vary even within the same species.

The present invention, as outlined in FIG. 1, describes an animal recognition method and apparatus for animals with unique nose patterns (subject animals) through the acquisition of identifiable nose pattern images by utilizing a body stabilizer unit to minimize movement and resistance in the subjects; an image acquisition unit to capture said images; and an image recognition unit that generates processed nose pattern images via noise reduction and image quality reinforcement techniques, and from it, nose pattern codes for enrollment and identification.

The image acquisition unit 102 may include the image analysis unit to be described later; or, the image analysis unit may be included in the image recognition unit 103. In other words, various configurations and modifications are entirely possible to suit the user's request or the designer's purpose.

Figure 2:
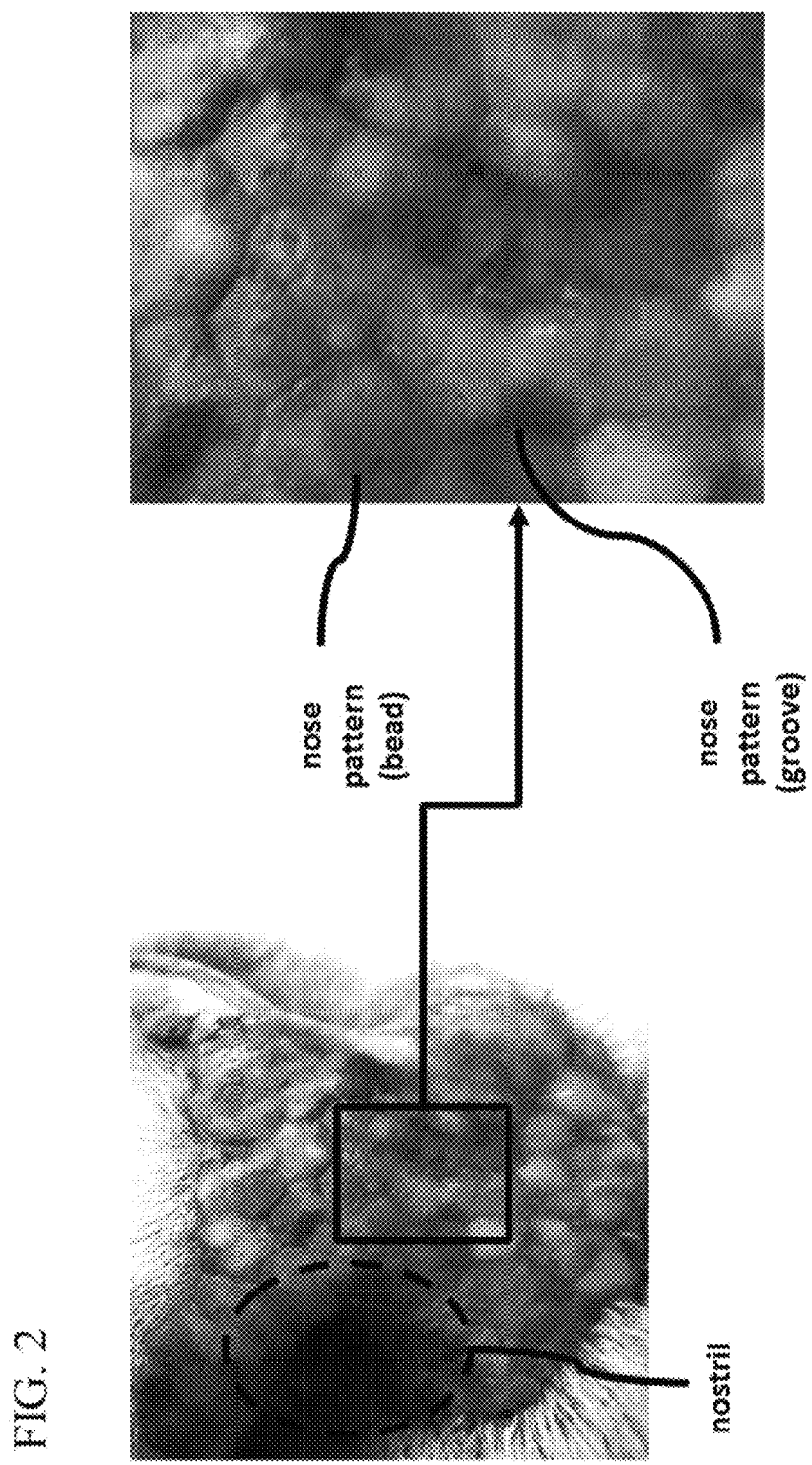
FIG. 2 is a photograph of the nose pattern of a specific animal species (deer) to demonstrate an example of the subject of the present invention.
Figure 3:
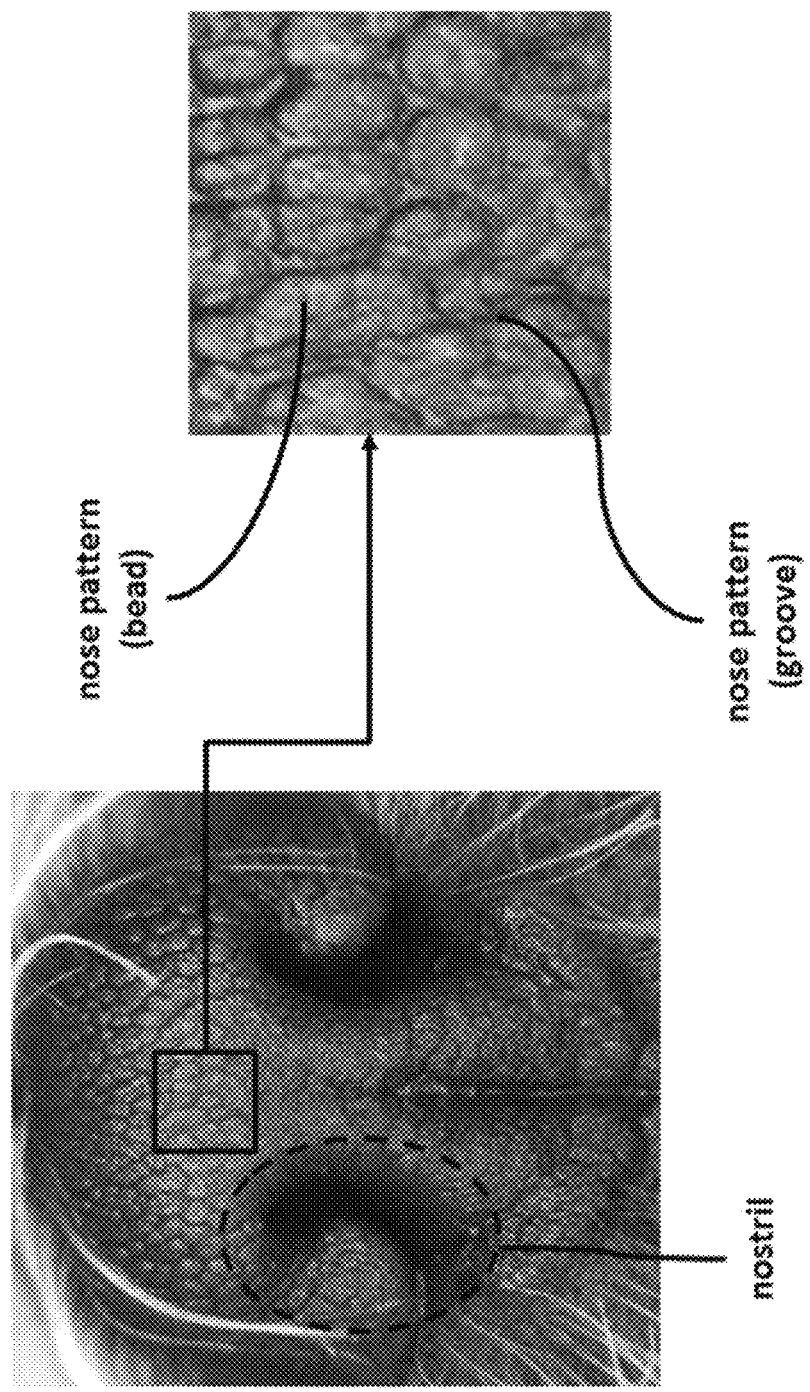
FIG. 3 is a photograph of the nose pattern of a specific animal species (dog) to demonstrate another example of the subject of the present invention.

A significant number of species of animals are known to have unique nose patterns. FIG. 2 and FIG. 3 show two examples of nose patterns, as taken using a model of the image acquisition unit. In the deer nose pattern in FIG. 2 the key features are the nostrils and the beading and grooving patterns, where beads are areas of raised nose skin and grooves are the narrow valleys surrounding each bead. FIG. 3 shows the nose pattern on a dog where, while the specific size and shapes differ, a similar beading and grooving phenomenon can be found.

In the case of cows, deer and other larger animals, the beads tend also to be relatively larger, while in smaller species like cats and dogs the beads tend to be proportionately smaller. In fact, even in the same species, the size of the nose area as generally dependent on the body size can affect the size of the beading patterns; and so it is necessary that the recognition apparatus and method take into consideration the patterning variations in different species and breeds.

Next, it is imperative to address the physiological characteristics of the nose of subject animals. As shown in FIG. 4, a healthy nose maintains a layer of moisture on the surface, which aggressively reflects light in photos taken under natural settings. This also adversely affects the results of any method that relies on contact imprinting, such as with paper or glass, as the moisture can often cause blurring and image distortions. As for image capturing, there is also ample possibility that the moisture would reflect light or absorb the infrared range. Thus, the moisture presents an unavoidable problem that needs to be addressed and solved.

The size and shape of the animal's face and body, as relating to the species and breed, also matter as the shape and length of the head and muzzle affect the capture and body stabilizer units.

The temperament of the subject animal is a factor as well, as it can vary from one individual to another even in the same species or breed. While some subjects are naturally tame and cooperative, others are more timid or aggressive especially towards the various (capturing, stabilizing, or illumination) apparatuses and human operators, making the work out in the field difficult or unsafe, especially for a non-professional user. Therefore, an effective method and apparatus must not aggravate the subject animals.

The technical configuration of the animal recognition apparatus is as follows: body stabilizer unit, image acquisition unit, and image recognition unit. The body stabilizer unit refers to the set of devices that prevent disruptive movements from the subject animal; the image acquisition unit refers to the software and hardware described in the present invention necessary to acquire the nose pattern images of a variety of animals; and the image recognition unit refers to the software and hardware needed for nose pattern image recognition.

Figure 5:
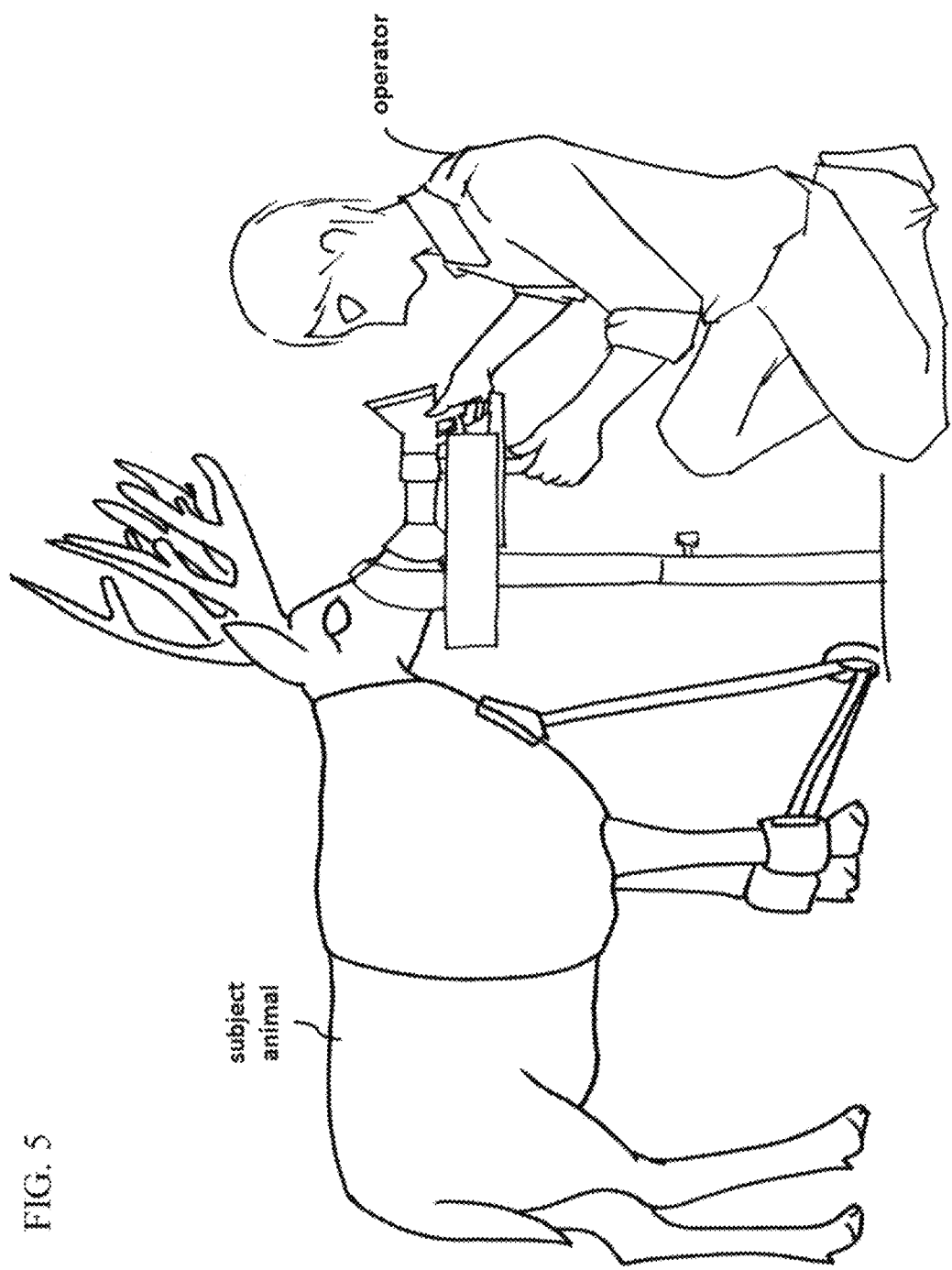
FIG. 5 is a diagram illustrating the operation of the animal recognition apparatus in the present invention.
Figure 7:
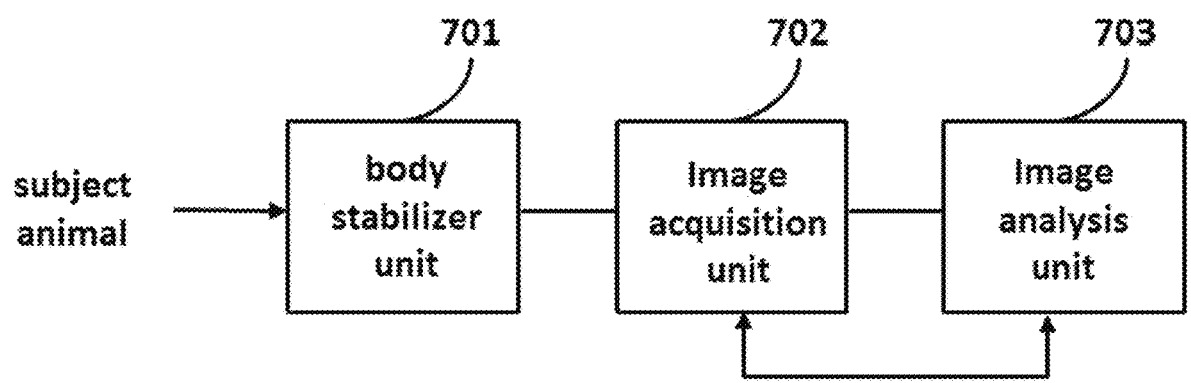
FIG. 7 is a block diagram illustrating a configuration of the animal recognition apparatus in the present invention in which each of the parts, the body stabilizer unit, the image acquisition unit, and the image recognition unit are all separate.
Figure 8:
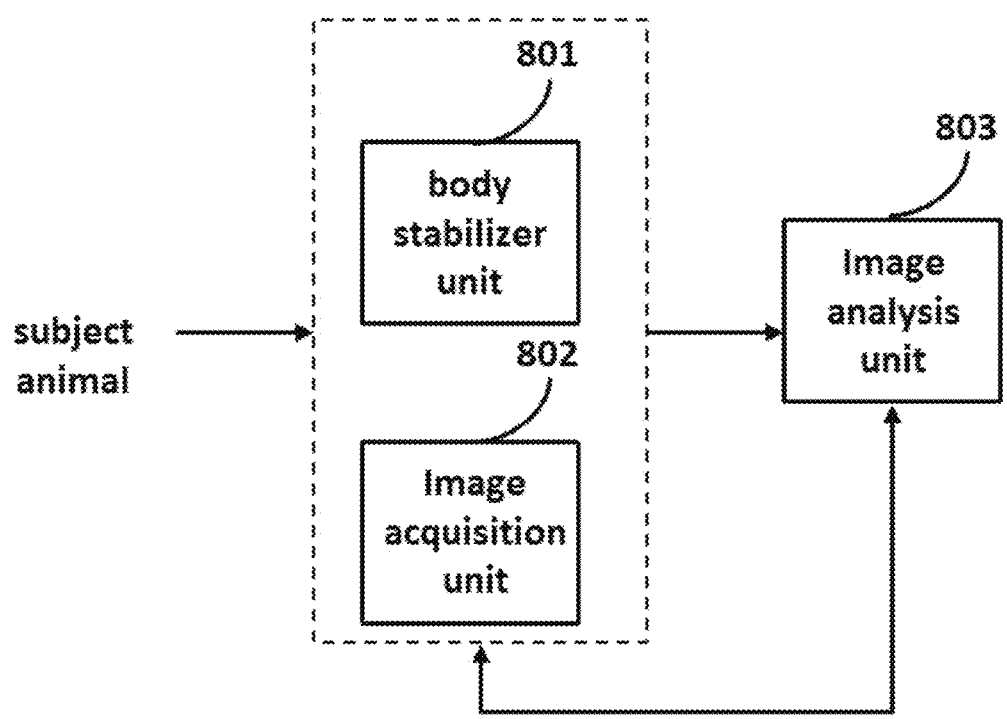
FIG. 8 is a block diagram illustrating a configuration of the animal recognition apparatus in the present invention in which the body stabilizer unit and the image acquisition unit are separate from the image recognition unit.
Figure 9:
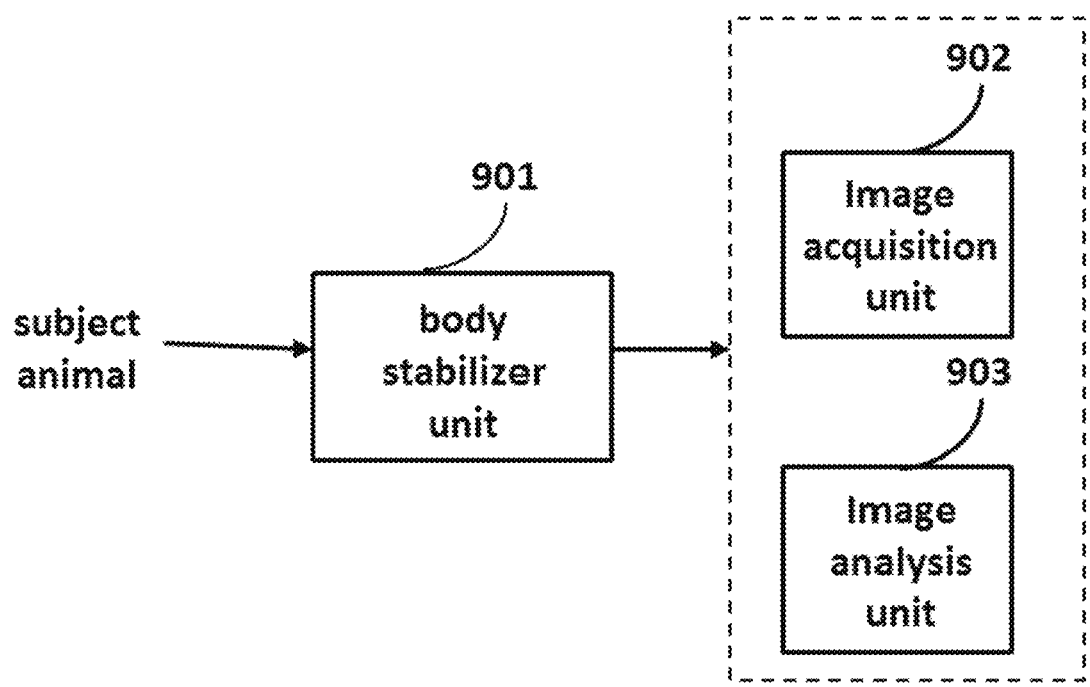
FIG. 9 is a block diagram illustrating a configuration of the animal recognition apparatus in the present invention in which the image acquisition unit and the image recognition unit are separate from the body stabilizer unit.
Figure 10:
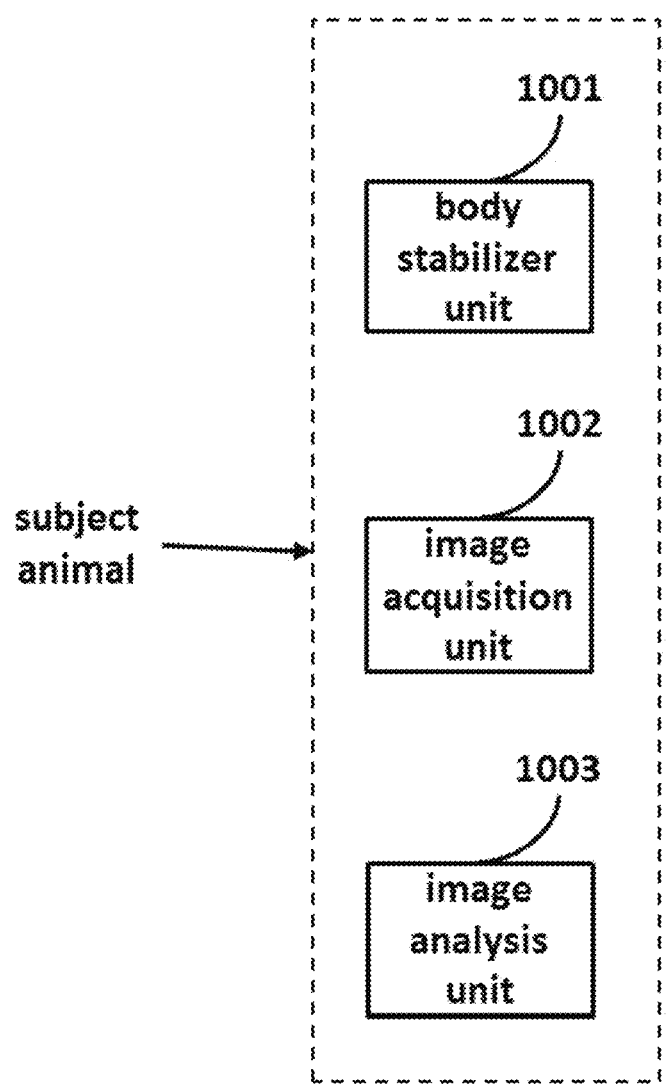
FIG. 10 is a block diagram illustrating a configuration of the animal recognition apparatus in the present invention in which the body stabilizer unit, the image acquisition unit, and the image recognition unit are all connected.

FIGS. 5 and 6 illustrate a practical application and operation of the overall animal recognition apparatus in the present invention, whereas the block diagrams in FIGS. 7, 8, and 9 show the connective combinations among the body stabilizer, image acquisition, and image recognition units. As previously mentioned, the animal recognition apparatus may be configured with a certain level of flexibility depending on the given animal or setting, where all three component units could be connected, or just two, or all three are set up separately.

Figure 11:
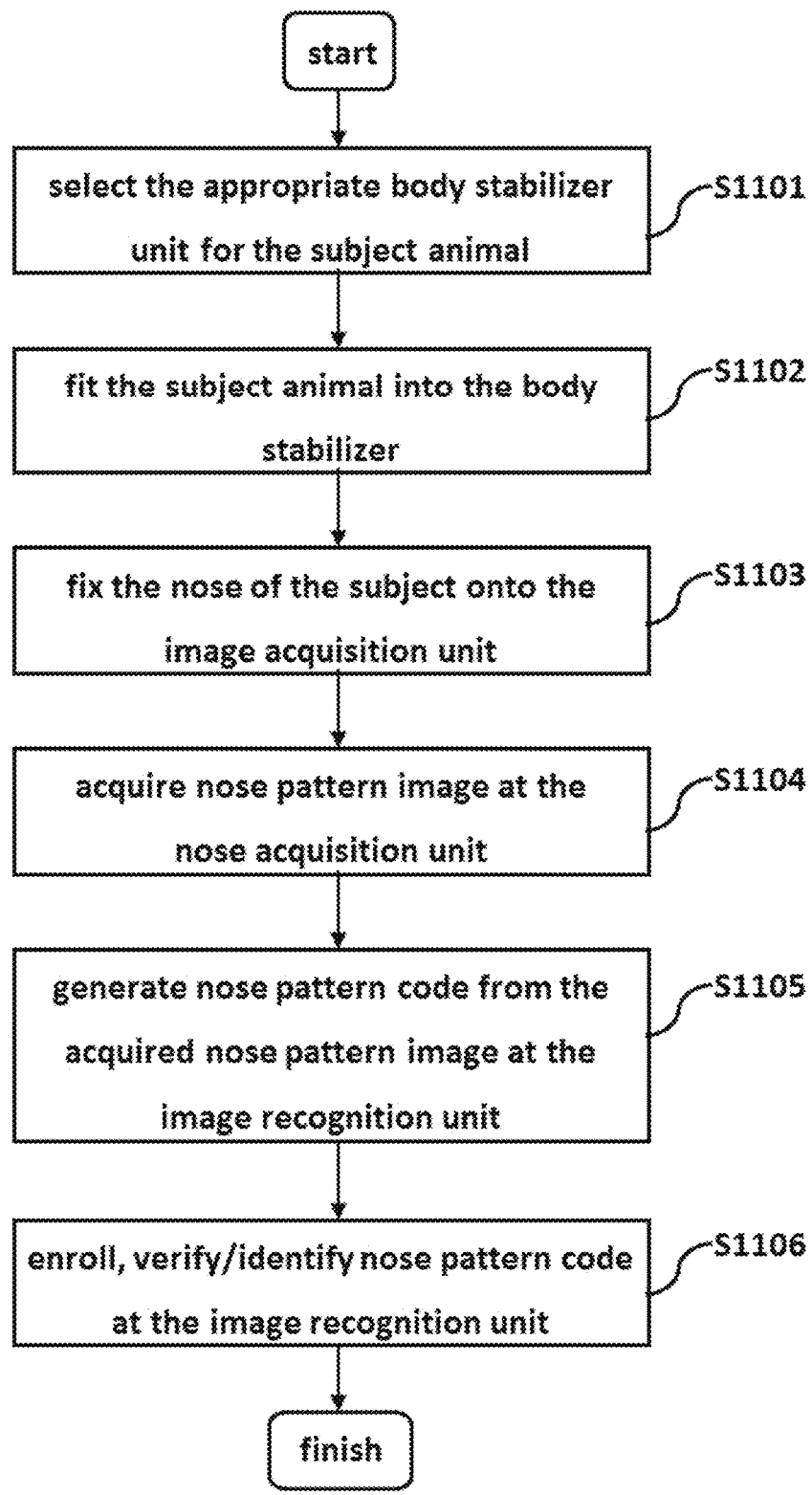
FIG. 11 is a flowchart illustrating the method of operating the animal recognition apparatus in the present invention.

The flowchart in FIG. 11 summarizes the method of animal recognition in the present invention, starting with S1101 selecting and S1102 fitting the animal into the appropriate body stabilizer unit; S1103 fixing the nose of the subject onto the image acquisition unit and S1104 acquiring the nose pattern image; S1105 at the image recognition unit, generating a nose pattern code using the raw or processed nose pattern image, and S1106 enrolling and identifying the individual using the nose pattern code. However, this is not to say that this sequence of events cannot be modified; those knowledgeable in the field of the present invention may choose to change the order of the steps or run more than one in parallel without departing from the core concept.

The purpose of the body stabilizer unit is to temporarily control the movement or resistance of the subject animal in reaction to the illumination or the operator, such as head turning or aggressive behavior, during the nose pattern image acquisition process to yield the best quality image. This is a safety measure against the animal accidentally harming itself or the human operators, which would incur added difficulties as well as cost. Moreover, an ideal nose pattern image is one taken from head-on and this is difficult to obtain with a highly uncooperative subject animal without the help of a body stabilizer.

Figure 12:
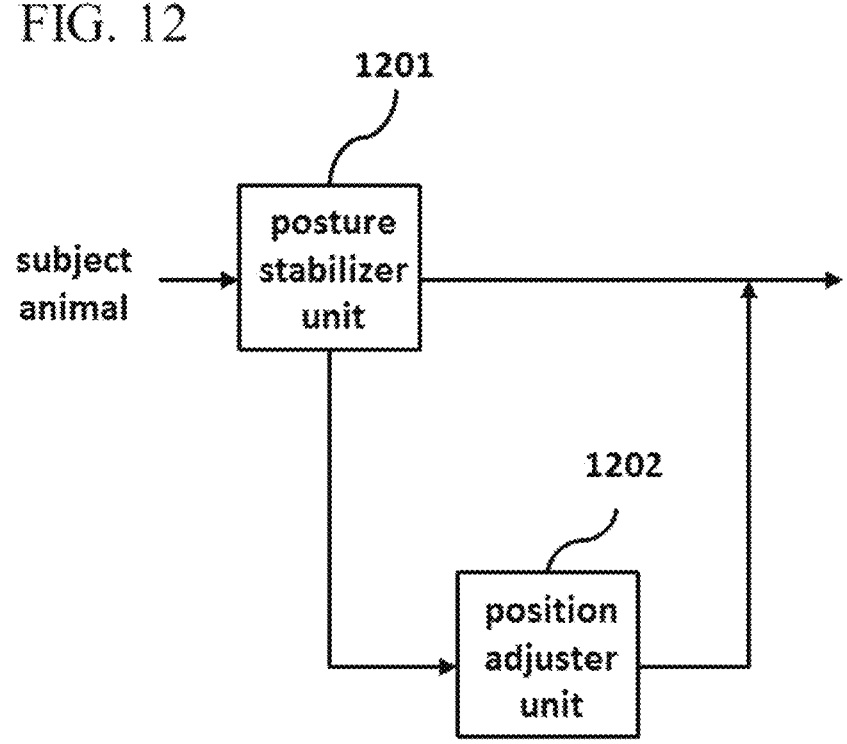
FIG. 12 is a block diagram schematically showing how to use the body stabilizer unit.
Figure 13:
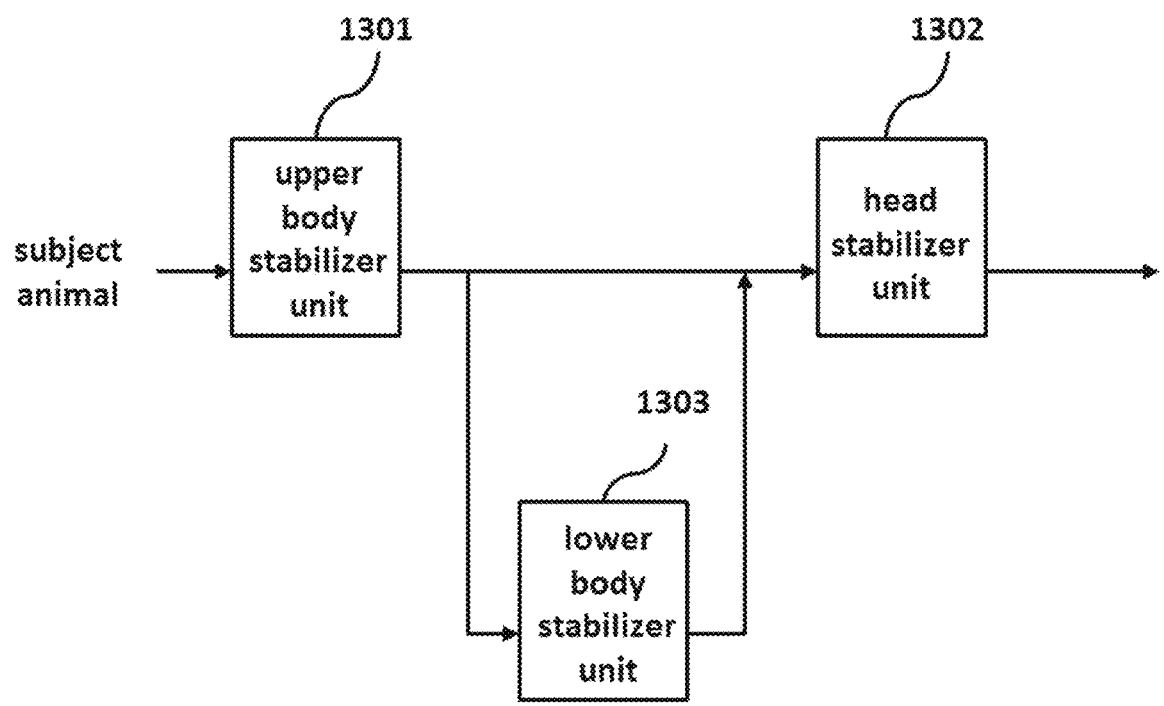
FIG. 13 is a block diagram schematically showing how to use the posture stabilizer unit.
Figure 14:
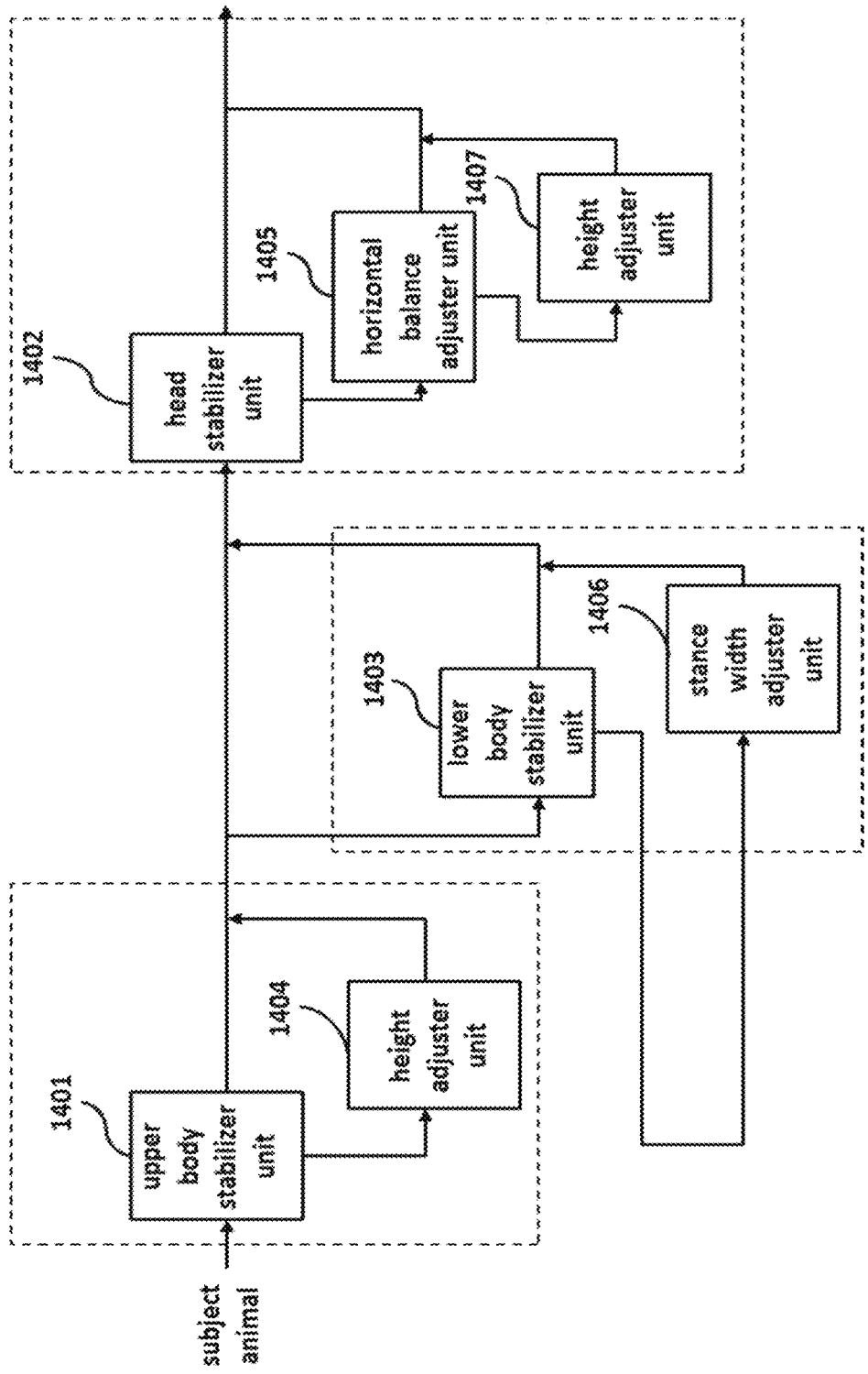
FIG. 14 is a block diagram schematically showing how to use the position adjuster unit.

Thus, the four primary functions of the body stabilizer unit are as follows: minimize the motion of the subject animal during the image acquisition process, act as a safety measure to protect the operator and apparatus, protect the subject animal from self-harm, and hold the nose in place for the best angle of image capture. As shown in FIG. 12, the body stabilizer unit comprises the posture stabilizer unit 1201, and also the position adjuster unit 1202 to accommodate the subject's stance width. FIG. 13 shows a more detailed breakdown of the posture stabilizer unit.

Although it is easy to assume that the only body part that needs to be properly restrained to obtain a good nose image is the head, the subject animal can and often will resist with the whole body and thereby cause blurry images. This problem may be mitigated by stabilizing the neck and shoulder area (upper body), as well as the back, front, and hind legs (lower body). Vets commonly forgo the usage of anesthesia during procedures whenever possible by applying pressure on the nape or shoulder of the patient animals; the body stabilizer is meant to simulate this method by allowing the subject animal to rest its head on the chin support while holding it in position with the head stabilizer unit 1302 and applying appropriate pressure using the upper body stabilizer unit 1301. Further movement in the lower body, especially in the case of larger animals whose powerful legs may pose a danger to the operators and equipment, may additionally be held in check by the lower body stabilizer unit 1303.

The configuration of the position adjuster unit is modifiable in accordance with the posture stabilizer unit settings, as the operator sees fit for the subject animal. Possible additions are the height adjuster unit 1404 to the upper body stabilizer unit 1401; stance width adjuster unit 1406 to the lower body stabilizer unit 1403; and the horizontal balance adjuster unit 1405 and the height adjuster unit 1407 to the head stabilizer unit 1402.

Figure 15:
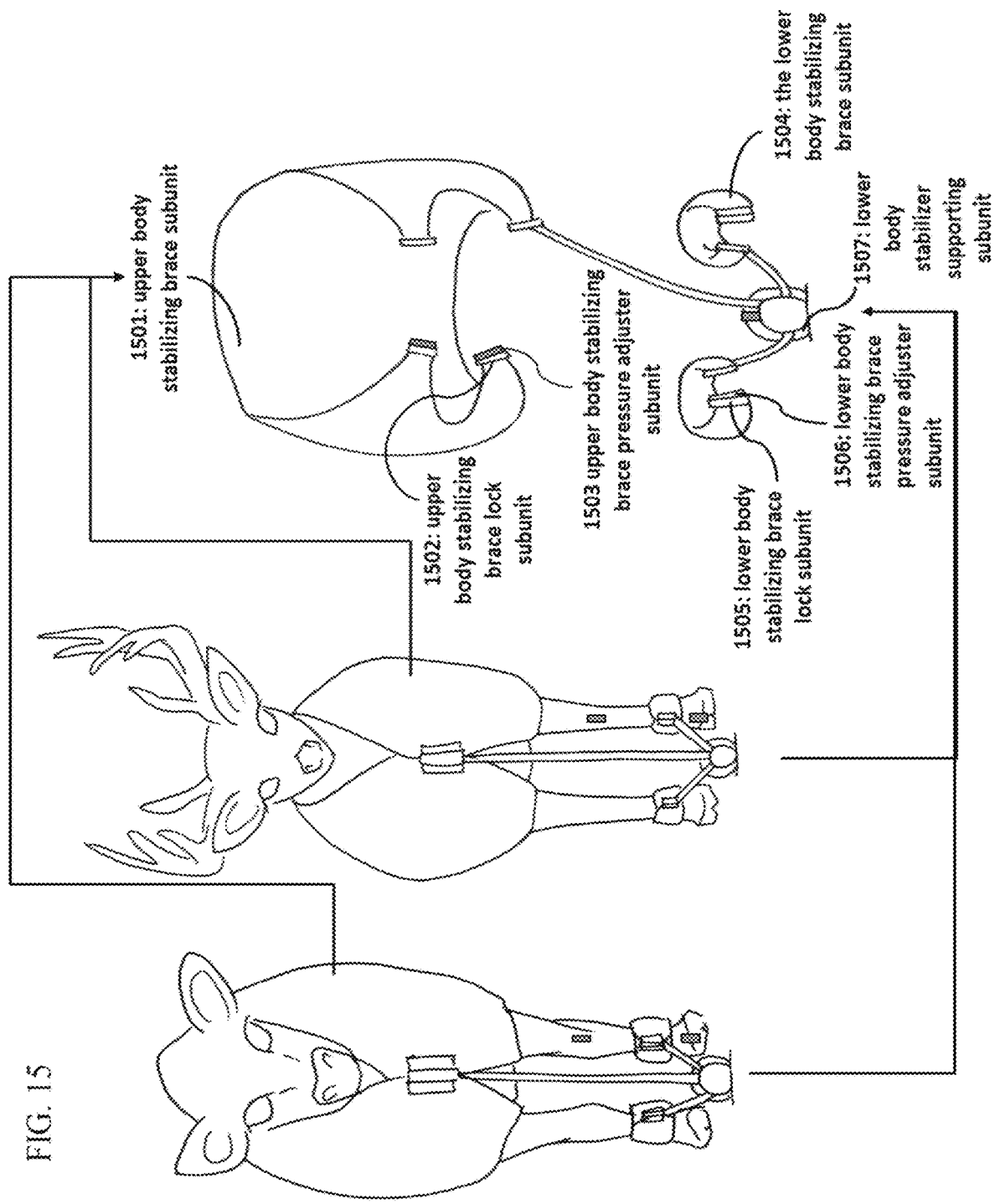
FIG. 15 is a diagram illustrating the application of the upper and lower body stabilizer units on two specific species (cow and deer).
Figure 16:
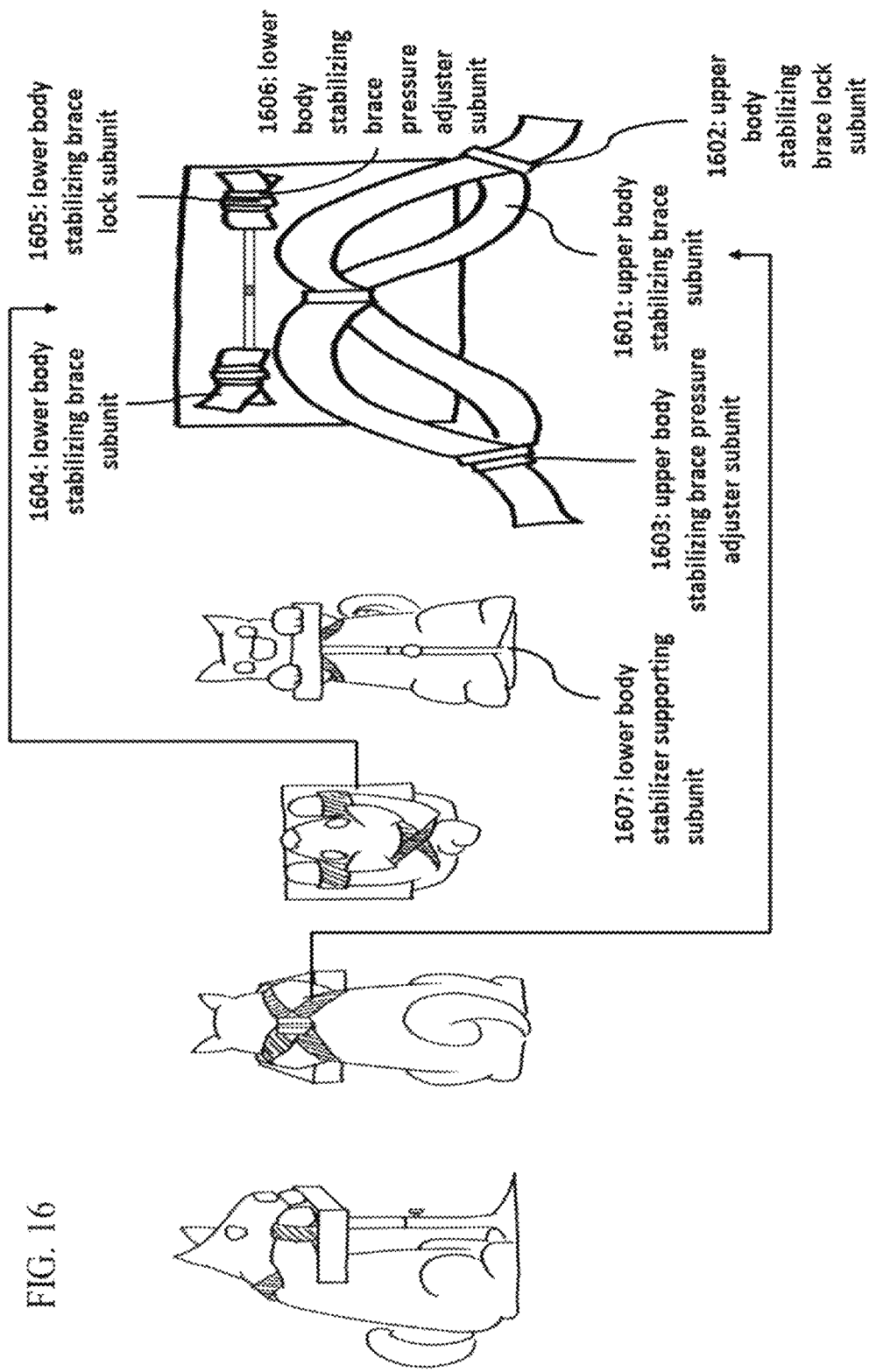
FIG. 16 is a diagram illustrating the application of the upper and lower body stabilizer units on two other specific species (dog and cat).

FIGS. 15 and 16 each show an example of the posture stabilizer unit with upper and lower body stabilizer units as appropriate for larger animals as cows and deer, and for smaller animals as dogs and cats, respectively. Depending on the species, the upper and lower body stabilizers may be set up in various combinations—each independently, in conjunction, or connected at certain parts.

In both FIGS. 15 and 16, the upper body stabilizer unit comprises the upper body stabilizing brace subunit 1501, 1601 and the upper body stabilizing brace lock subunit 1502, 1602; the upper body stabilizing brace pressure adjuster subunit 1503, 1603 is optional. The upper body stabilizing brace subunit 1501, 1601 may be made into a cover type, with durable synthetic fabrics, or with length-adjustable belts or cables. The upper body stabilizing brace lock subunit 1502, 1602 prevents the brace subunit from coming undone during the procedure, and may be manual or electronic. The upper body stabilizing brace pressure adjuster subunit 1503, 1603 allows the upper body stabilizing brace subunit to apply pressure on the subject animal by, for example, inflating the brace with some gas or liquid with the use of a pressure injector paired with a pressure monitor subunit.

Likewise, in both FIGS. 15 and 16, the lower body stabilizer unit comprises the lower body stabilizing brace subunit 1504, 1604 and the lower body stabilizing brace lock subunit 1505, 1605; the lower body stabilizing brace pressure adjuster subunit 1506, 1606, as well as the lower body stabilizer supporting subunit 1507, 1607 are optional. The lower body stabilizing brace subunit 1504, 1604 may be made into a cover type, with durable synthetic fabrics, or with length-adjustable belts or cables. The lower body stabilizing brace lock subunit 1505, 1605 prevents the brace subunit from coming undone during the procedure, and may be manual or electronic. The lower body stabilizing brace pressure adjuster subunit 1506, 1606 allows the lower body stabilizing brace subunit to apply pressure on the subject animal by, for example, inflating the brace with some gas or liquid with the use of a pressure injector pair with a pressure monitor subunit. The lower body stabilizer supporting subunit 1507, 1607 fastens the lower body stabilizer unit to the ground or at a certain distance from the equipment, and may be made up the lower body supporting subunit and the lower body supporter connector subunit. The lower body supporting subunit and the lower body supporter connector subunit may take many forms to suit the subject animal, and may be made of steel or other metals, as well as durable synthetic fibers, rubber, or fabric.

Figure 17:
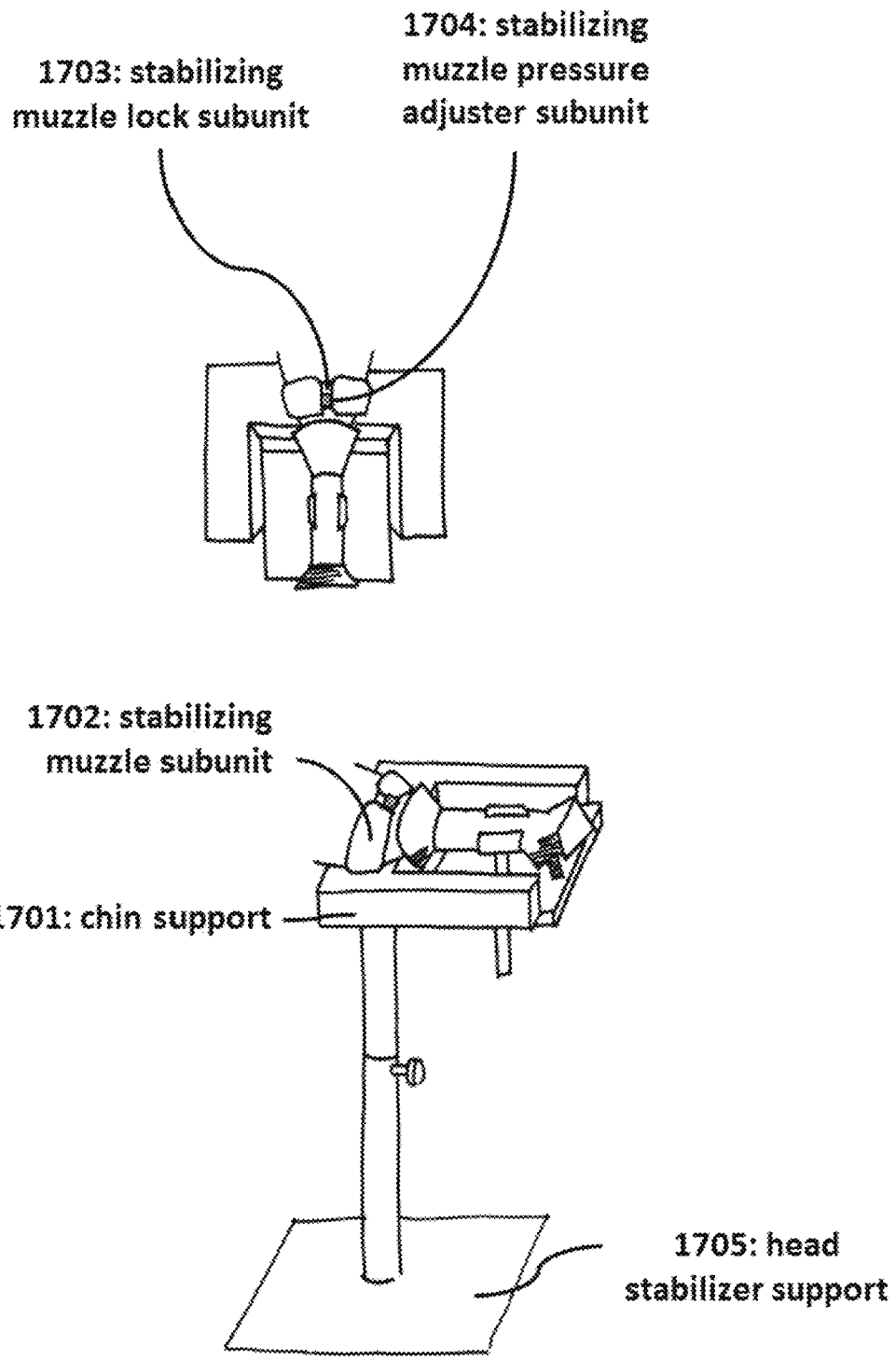
FIG. 17 is a diagram illustrating the configuration of the head stabilizer unit.

The head stabilizer unit in FIG. 17 comprises the chin support 1701, and the stabilizing muzzle subunit 1702 that holds the subject's nose in the correct position. The chin support 1701 may be made of various materials as wood, plastic, rubber, or metal, and should withstand the weight of the subject's head while providing a comfortable headrest and room for additional supporting attachments. The stabilizing muzzle subunit 1702 will be used when the head movement cannot be controlled with the chin support alone, and may be made into a cover type with durable synthetic fabrics, or with length-adjustable belts or cables, to span the muzzle area. The stabilizing muzzle lock subunit 1703 prevents the brace subunit from coming undone during the procedure, and may be manual or electronic. The stabilizing muzzle pressure adjuster subunit 1704 allows the stabilizing muzzle subunit to apply pressure on the subject animal's muzzle by, for example, inflating the brace with some gas or liquid with the use of a pressure injector paired with a pressure monitor subunit. The head stabilizer unit may also have a head stabilizer support 1705 that fastens the head stabilizer unit to the ground or at a certain distance from the equipment while supporting the weight of the subject animal's head, and may be made into various shapes using durable materials as wood, stone, or metal.

Figure 18:
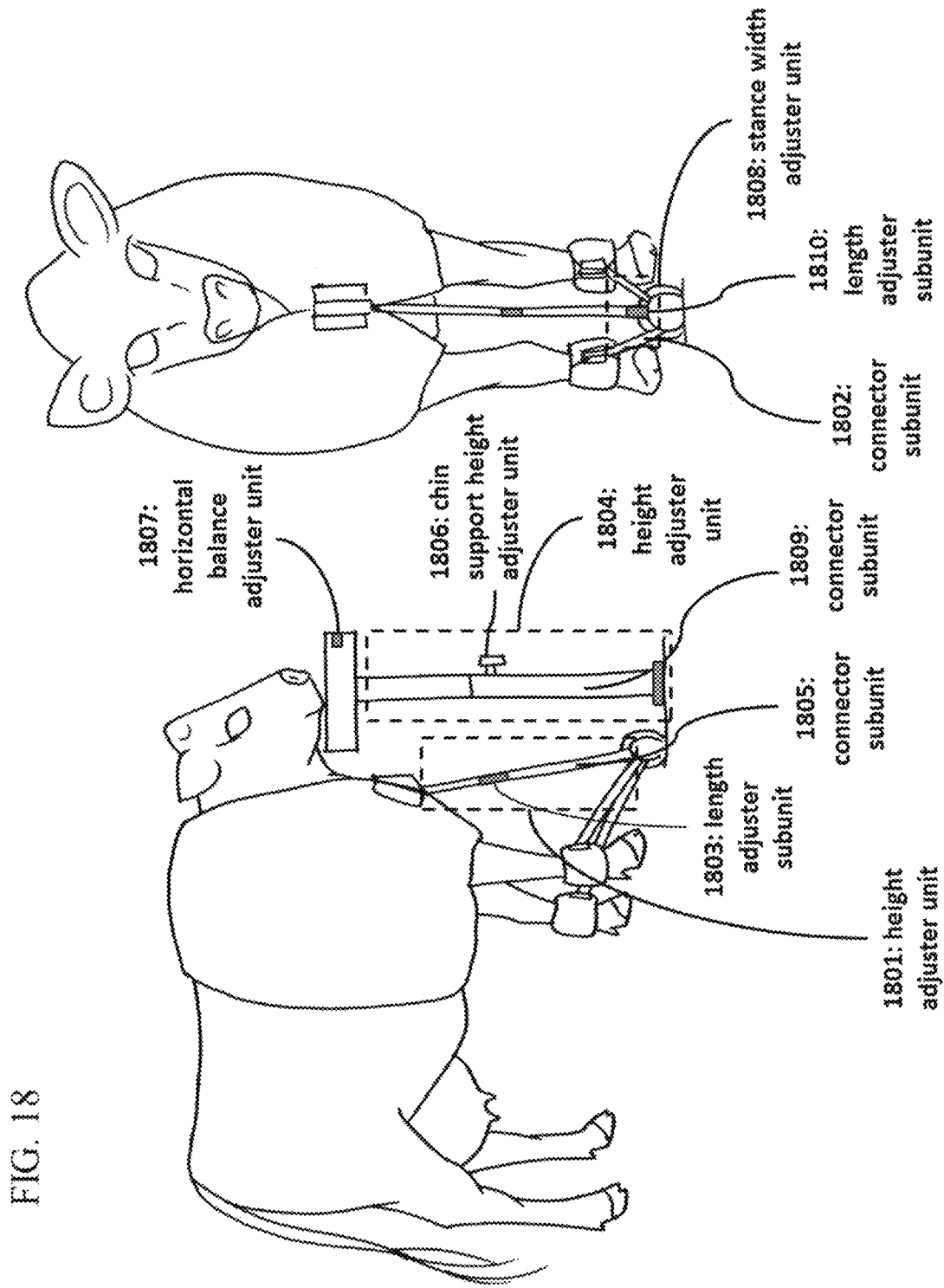
FIG. 18 is a diagram illustrating the implementation of the appropriate posture stabilizer unit and position adjuster unit on a specific species (cow).
Figure 19:
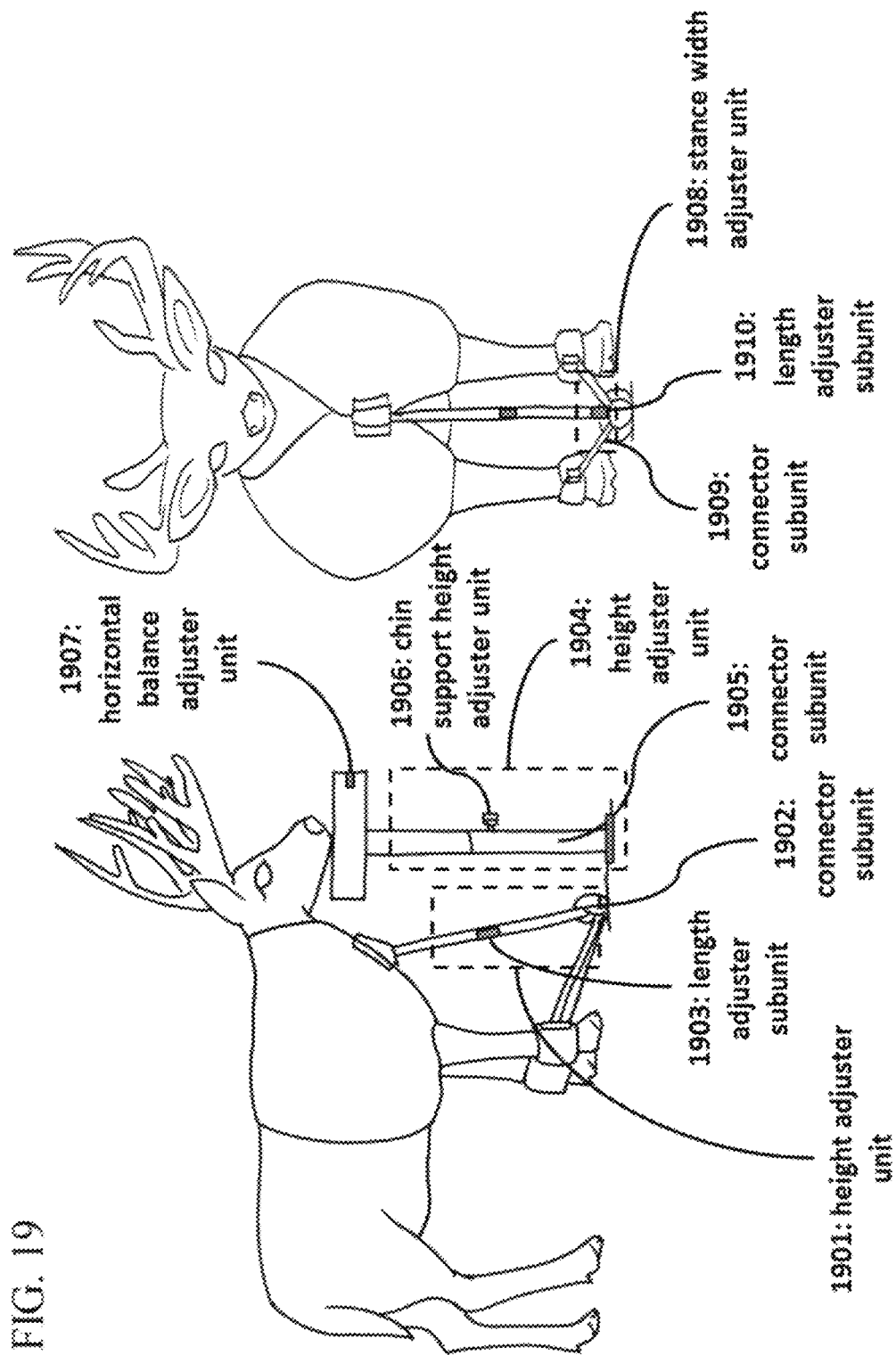
FIG. 19 is a diagram illustrating the implementation of the appropriate posture stabilizer unit and position adjuster unit on another species (deer).

The position adjuster unit adjusts the settings of the posture stabilizer unit as per each animal's physical characteristics in order to produce the most comfortable position for the subject, and comprises the height adjuster unit, horizontal balance adjuster unit, and stance width adjuster unit. The examples in FIGS. 18 and 19 show the subject animal (cow and deer, respectively) fitted into the upper and lower body stabilizer units where the height adjuster units 1801, 1804, 1901, 1904 are set to accommodate the subject's height. The height adjuster 1801, 1901 connects the upper and lower body stabilizer units and may comprise the connector subunit 1802, 1902 made with belts or cables, and the length adjuster subunit 1803, 1903 that adjusts the length of the connector subunit. The height adjuster unit 1804, 1904 for the head stabilizer unit may also comprise the connector subunit 1805, 1905 connecting the chin support to the ground and the chin support height adjuster unit 1806, 1906. The horizontal balance adjuster unit 1807, 1907, placed inside or outside the chin support and comprising a horizontal balance sensor with a display monitor, positions the chin support under the subject animal's head to directly face the image acquisition unit. The horizontal balance sensor may comprise gravity, gyro, or pressure sensors. The stance width adjuster unit 1808, 1908 may be used when the lower body is fastened in the lower body stabilizer unit, and may comprise connector subunit 1809, 1909 of belts or cables and a length adjuster subunit 1810, 1910 that connects both sides of the lower body.

Figure 20:
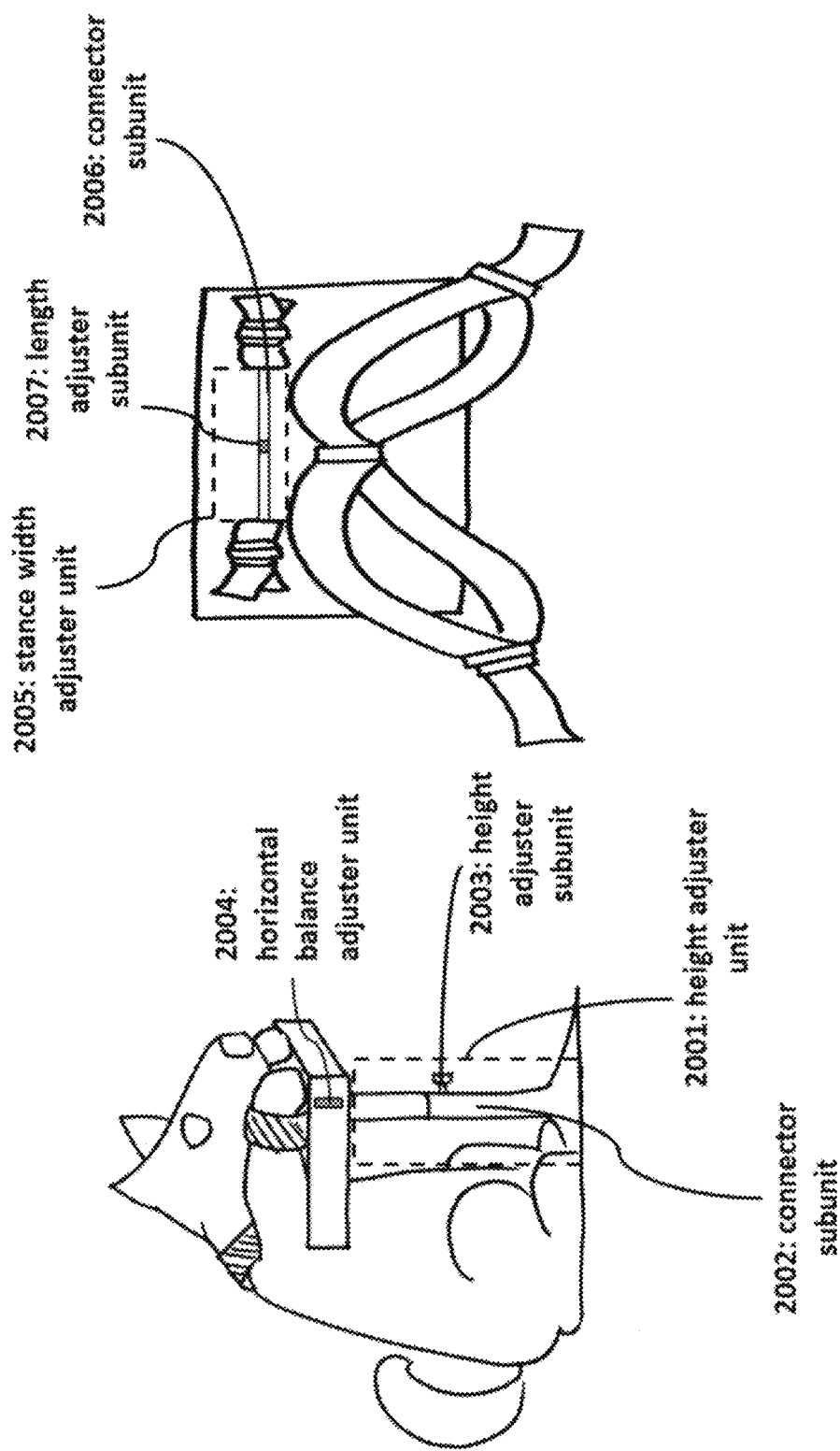
FIG. 20 is a diagram illustrating the implementation of the appropriate posture stabilizer unit and position adjuster unit on two small species (dog and cat).

As shown in FIG. 20, for certain species of animals like cats or dogs, it may be appropriate to combine the upper and lower body stabilizer units with a height adjuster unit 2001, placed in front or on top of the head stabilizer unit, that positions the chin support to fit the height of the subject animal and reach its head. The height adjuster unit 2001 that adjusts the height of the head stabilizer unit may comprise a connector subunit 2002 that connects the chin support to the ground and a height adjuster subunit 2003 that adjusts the height of the connector subunit. The horizontal balance adjuster unit 2004, placed inside or outside the chin support and comprising a horizontal balance sensor with a display monitor, positions the chin support under the subject animal's head to directly face the image acquisition unit. The horizontal balance sensor may comprise gravity, gyro, or pressure sensors. The stance width adjuster unit 2005 may be used when the lower body is fastened in the lower body stabilizer unit, and may comprise a connector subunit 2006 of belts or cables and a length adjuster subunit 2007 that connects both sides of the lower body.

The sequence of operation for the body stabilizer unit is as follows: S2101 select the appropriate body stabilizer unit for the subject animal by taking into consideration the overall size, leg length, feet size, head size, and the relative location of the nose; S2102 fit the subject animal into the upper body stabilizer unit; S2103 fasten the upper body by utilizing the upper body stabilizing brace subunit and upper body stabilizing brace pressure adjuster subunit to fit the shoulder width; S2104 fit the subject animal into the lower body stabilizer; S2105 fasten the lower body by utilizing the lower body stabilizing brace subunit and lower body stabilizing brace pressure adjuster subunit to fit the ankles or legs; S2106 set the stance width adjuster, and also the height adjuster to fit the subject's height if necessary to connect the upper and lower body stabilizer units; S2107 fasten the head by utilizing the head stabilizer unit, making sure to set the height adjuster unit to the correct height and the horizontal balance adjuster unit to have the nose facing the image acquisition unit head-on. This sequence of events may be modified, by those knowledgeable in the field of the present invention, without departing from the core concept.

The purpose of the image acquisition unit is the capture and acquisition of nose pattern images. This can seem conceptually innocuous but the execution of it is nothing but, due to the morphological diversity of the nose and nose patterns, as well as the physiological nature of the rhinarium that yields unwanted light reflections. Thus, the six primary functions of the image acquisition unit are as follows: acquire good quality nose images usable by the image recognition unit without relying on the traditional methods that mandate direct contact; acquire good quality nose images from a wide variety of species; not be affected by a subject animal's particular size, shape, or physiology; employ a special kind of illumination to avoid issues with light reflections from the wet nose; and enable non-professional users to achieve the above five with ease.

Figure 22:
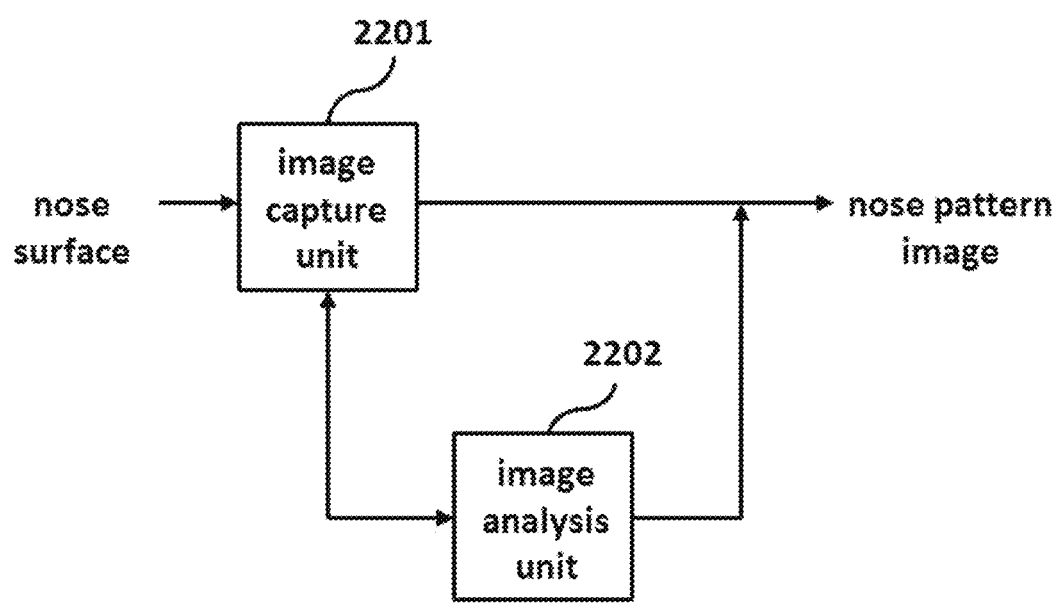
FIG. 22 is a block diagram illustrating the configuration of the image acquisition unit.
Figure 23:
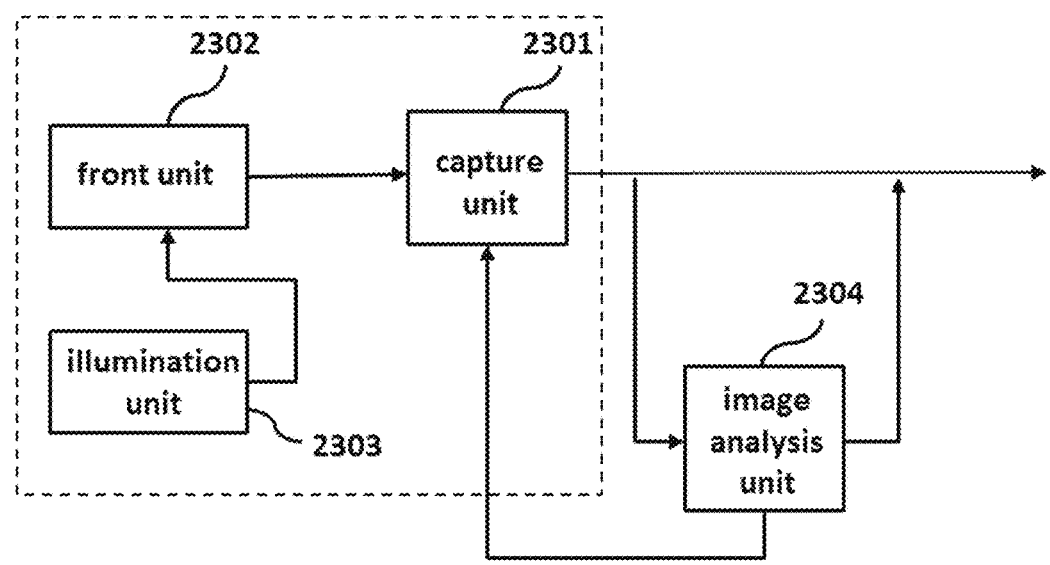
FIG. 23 is a block diagram schematically illustrating the image capture unit and the image analysis unit within the image acquisition unit.

As shown in FIG. 22, the image acquisition unit comprises the image capture unit 2201 that photographically captures nose pattern images, and also possibly the image analysis unit 2202 that analyzes the captured images and processes certain signals and information. The image capture unit comprises the capture unit 2301, the front unit 2302 that adjusts the field of view (FOV) and capture distance for each subject while blocking out the ambient light for a more controlled environment, and additionally the illumination unit 2303 that provides indirect illumination to overcome the light reflection issue (FIG. 23). Within the context of the present invention, the "acquisition" of nose pattern images refers to the entirety of the process of capturing and storing of nose pattern images. In other words, "acquiring" nose pattern images includes capturing photographic images by the image sensor in the image capture unit and storing the captured images in the buffer for further actions, including but not limited to image processing, best image selection, etc.

Figure 24:
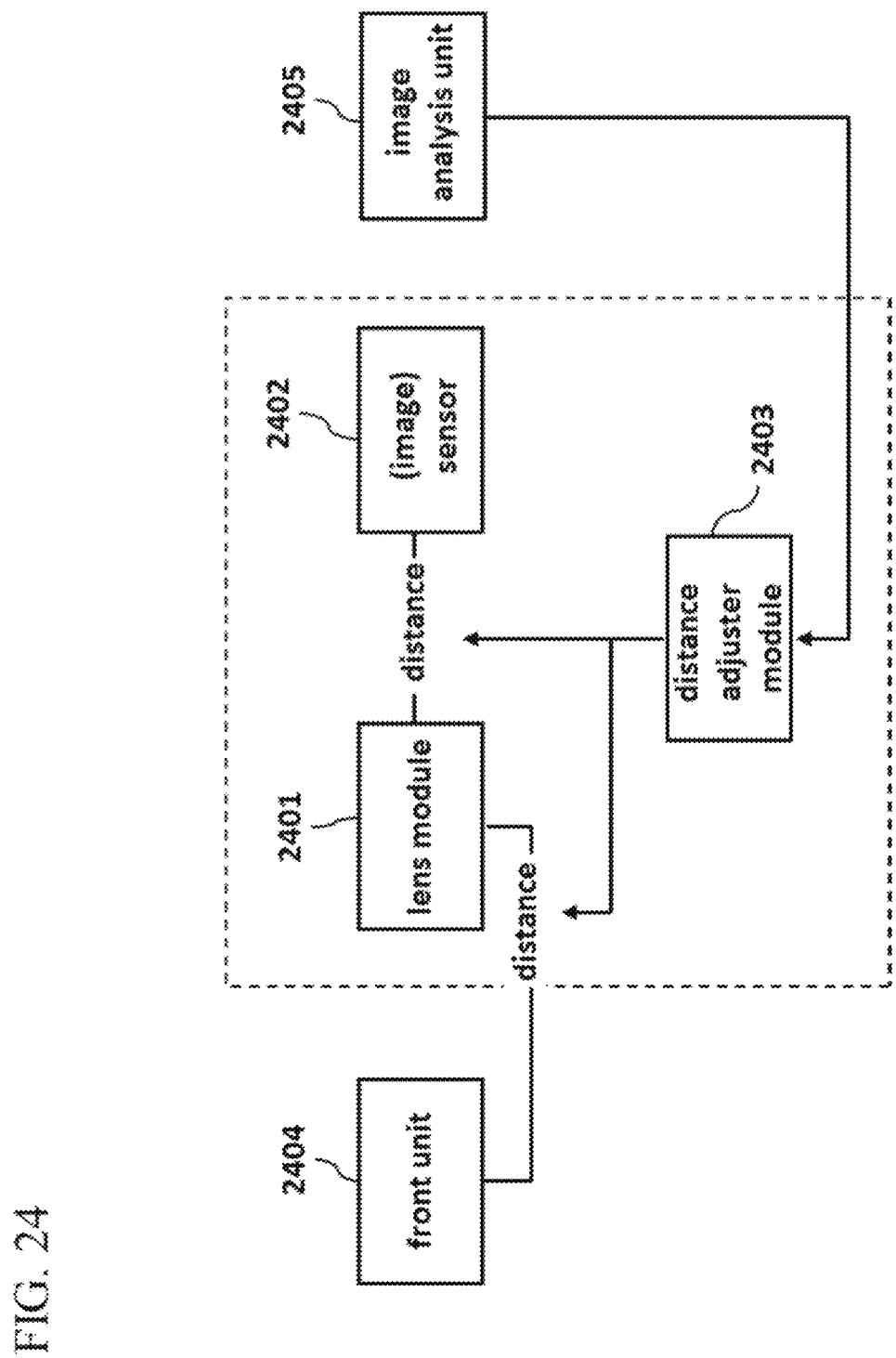
FIG. 24 is a block diagram illustrating the configuration of the image capture unit that moves the lens module and sensor according to the distance adjustment principle of the distance adjuster module.
Figure 25:
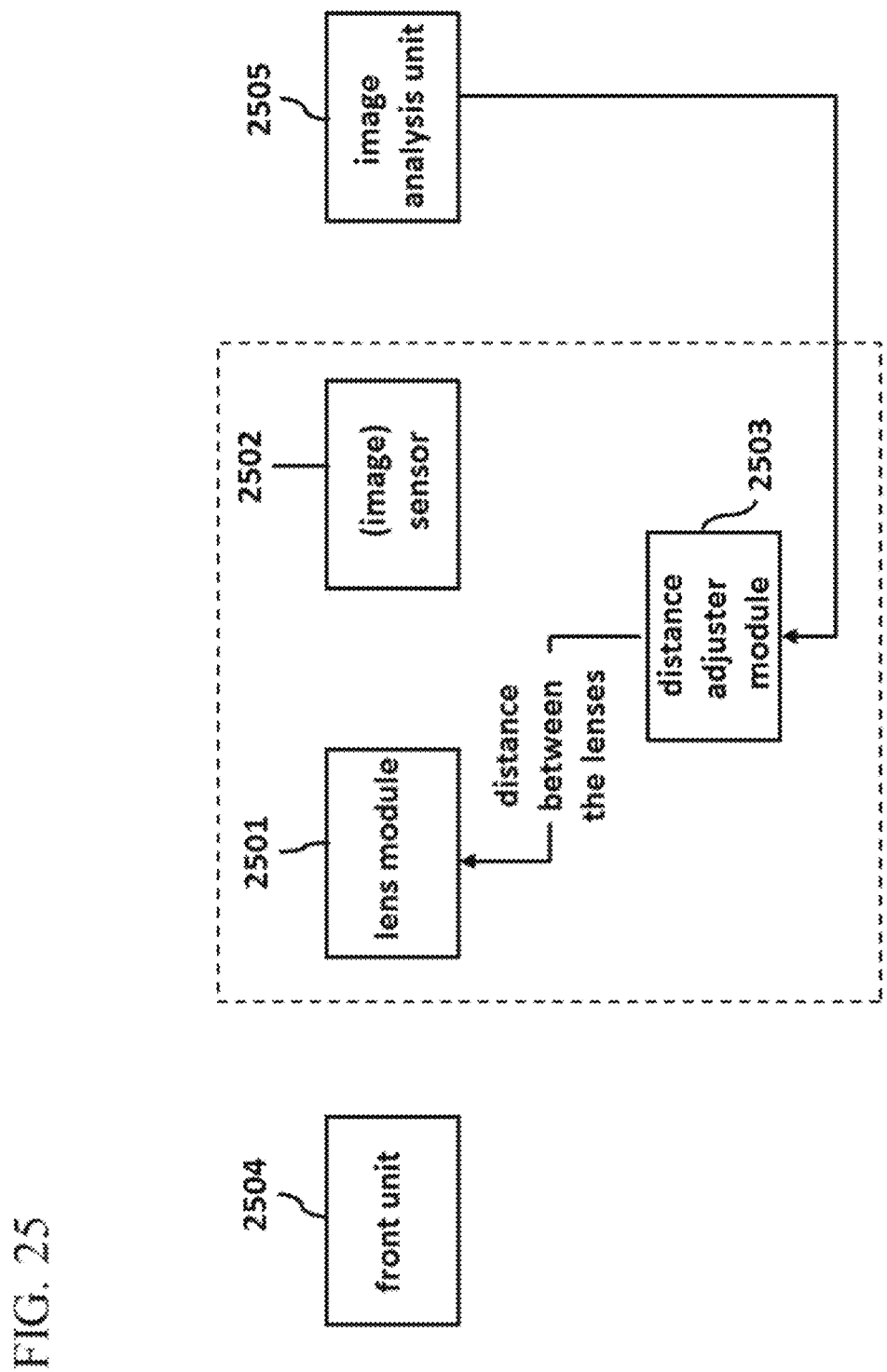
FIG. 25 is a block diagram illustrating the configuration of the image capture unit that adjusts the distance between the lenses in the lens module according to the distance adjustment principle of the distance adjuster module.
Figure 26:
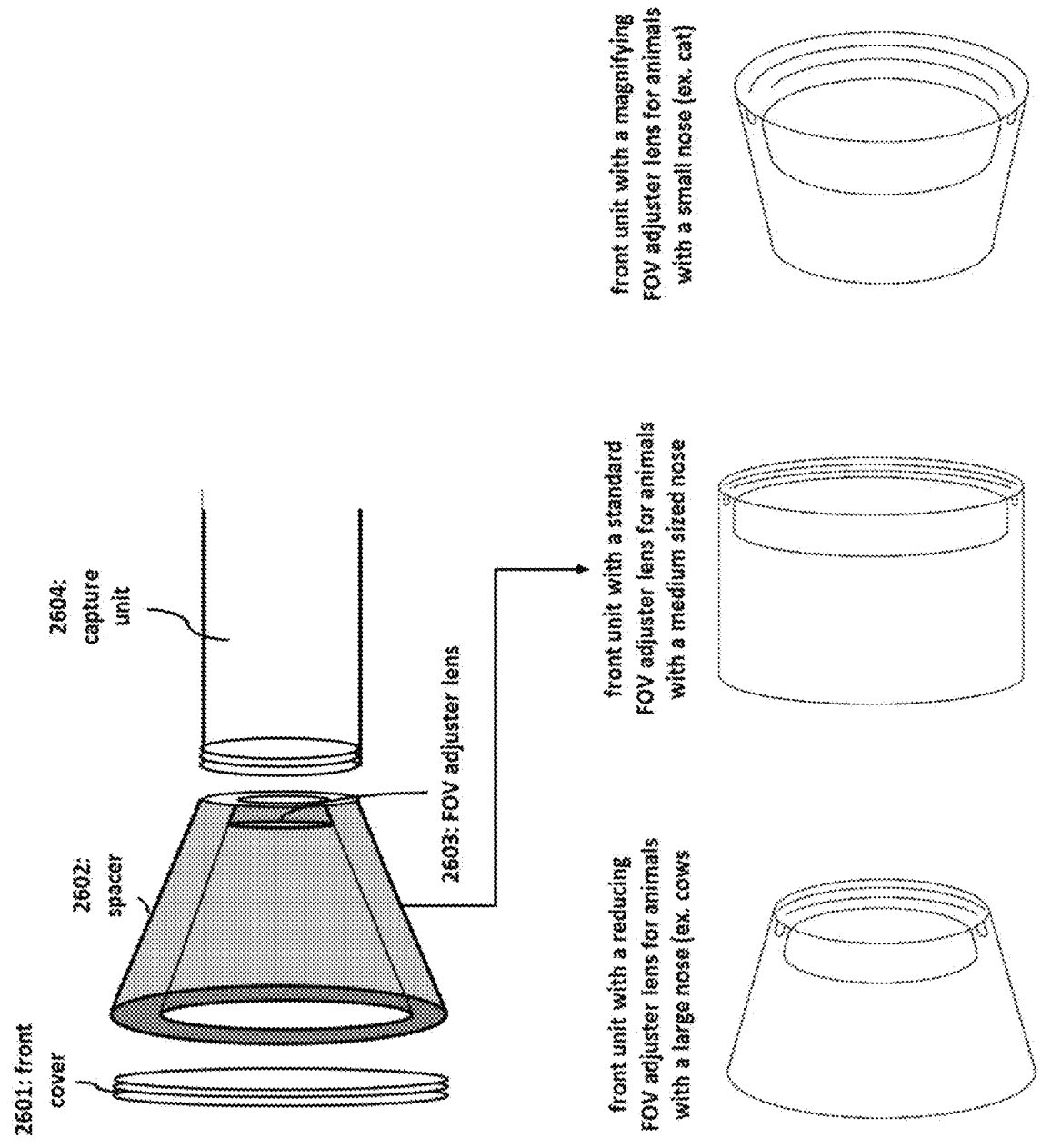
FIG. 26 is a diagram illustrating the configuration of the front unit of the image capture unit.

The image capture unit, as illustrated in FIG. 24, may comprise the lens module 2401 with two or more lenses; an image sensor 2402 (CMOS or CCD); and the distance adjuster module 2403 that controls the FOV and focus by moving the lens module and sensor, thereby manipulating the distances between the lenses and between the lens module and the sensor within the front unit 2404. The distance adjuster module 2401 moves the lens module or a plurality of lenses, and comprises a small motor and rack gear that the converts motor's circular motion to linear motion. Also, a guide rail that allows the lens module 2401 and sensor 2402, in linear periodic motion by the rack gear, to move between predetermined positions may also be installed. Alternatively, the image capture unit may also comprise the lens module 2501 and sensor 2502 in fixed positions, with the distance adjuster module 2503 only controlling the distances between the lenses within the lens module (FIG. 25).

The front unit may comprise a front cover 2601 that surrounds and/or comes in contact with the skin around the nose when the nose enters the front unit; a FOV adjuster lens 2603; a spacer 2602 that adjusts the distance between the subject's nose and the FOV adjuster lens 2603. The front cover 2601 and spacer 2602 may come in variable shapes or sizes to accommodate different species or breeds. The front cover 2601 should be of a color that is best suited for blocking out ambient light, most likely black or other dark hues, and made of materials that do not agitate the subject animals, such as synthetic fibers, rubber, textile, or plastic. The front cover also may be imbued with a calming scent for the subject animals, and made to be detachable for easy substitution when dealing with subjects of different physical requirements during the same session.

The standard FOV adjuster lens 2603 is modeled after the nose size of a typical (medium sized) dog; a reducing lens is used instead for larger noses, and a magnifying lens for smaller noses. The standard lens refers to a single or a set of lenses that allows the framing of a typical dog nose, and the reducing and magnifying lenses are made in relation to the standard.

The spacer 2602 consists of the exterior that the blocks the light coming from the outside, and the interior that surrounds the nose of the subject animal, and possibly also houses an illumination unit. The length of the spacer, which determines the distance between the FOV adjuster lens and the subject's nose, may be optimized using field trial results. It also may be efficient to have pre-designed, detachable front units with spacers and FOV adjuster lenses set to fit particular species or nose sizes based on experimental results.

Figure 27:
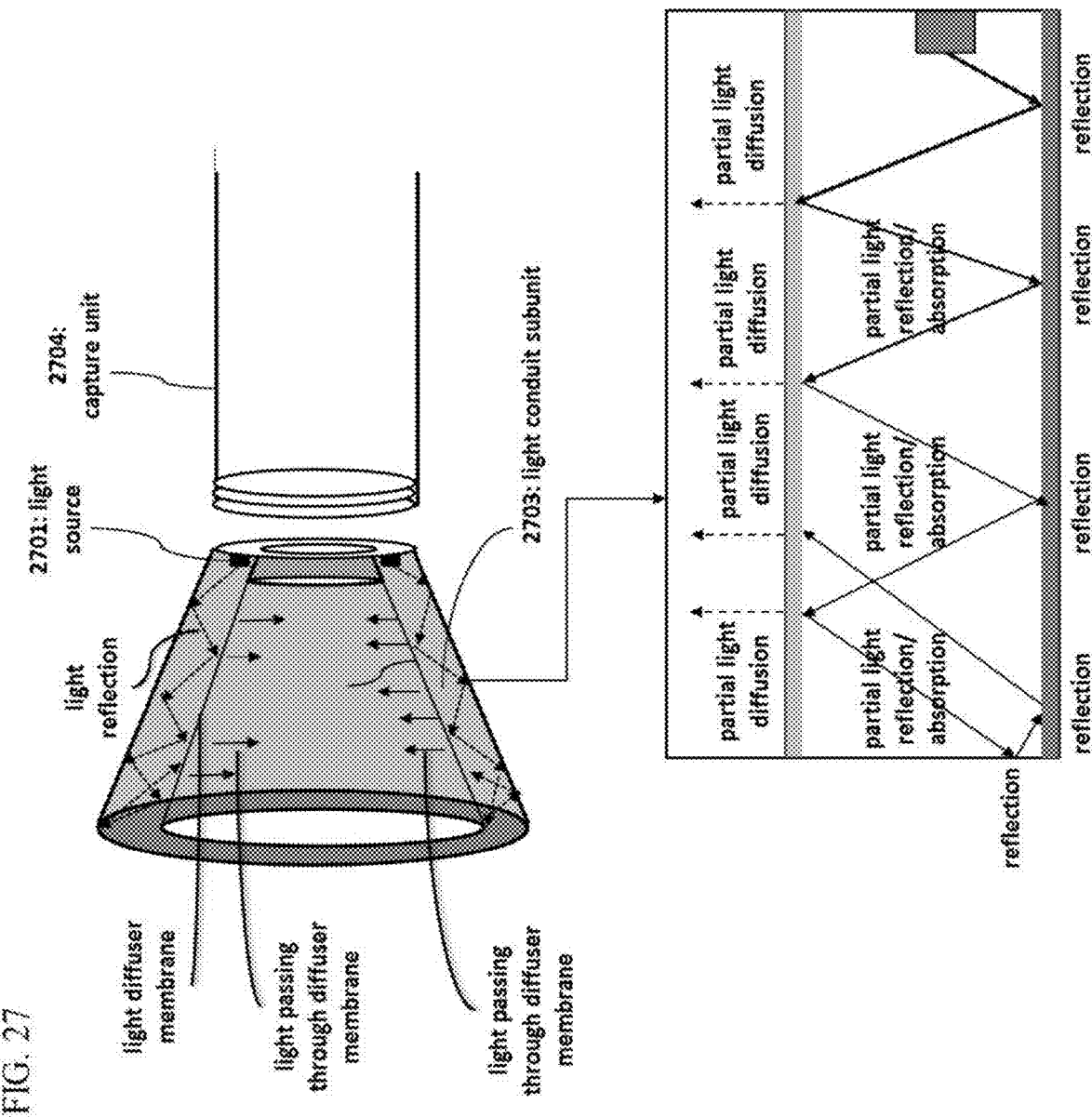
FIG. 27 is a diagram illustrating the configuration of the illumination unit.

The illumination unit in FIG. 27 seeks to eliminate the issues that arise from the reflection and absorption of light by the moisture on the nose surface by incorporating a light source 2701 of a specific wavelength region (that poses no threat to the health of the subject animal) in indirect illumination, wherein the light travels through a light conduit subunit 2703 and light diffuser subunit 2702. The light source 2701, light diffuser subunit 2702, and light conduit subunit 2703 may vary to suit different species of subject animals. The light source 2701 should have adjustable luminosity, avoid the infrared region that can be absorbed by the moisture and the UV region that can cause tissue damage, and be optimized to suit the particular characteristics of a species. Any type of light source consistent with the above description would suffice.

The light diffuser subunit 2702 partially absorbs and reflects light from the light source through the diffuser surface to indirectly illuminate the whole nose surface inserted into the front unit. The amount of light that eventually passes through the diffuser may be controlled with the type of material used, such as Hanji (traditional Korean paper handmade from mulberry trees), translucent tracing paper, or a special type of glass, and similar material may also be used to line the interior of the light conduit subunit 2703.

Figure 28:
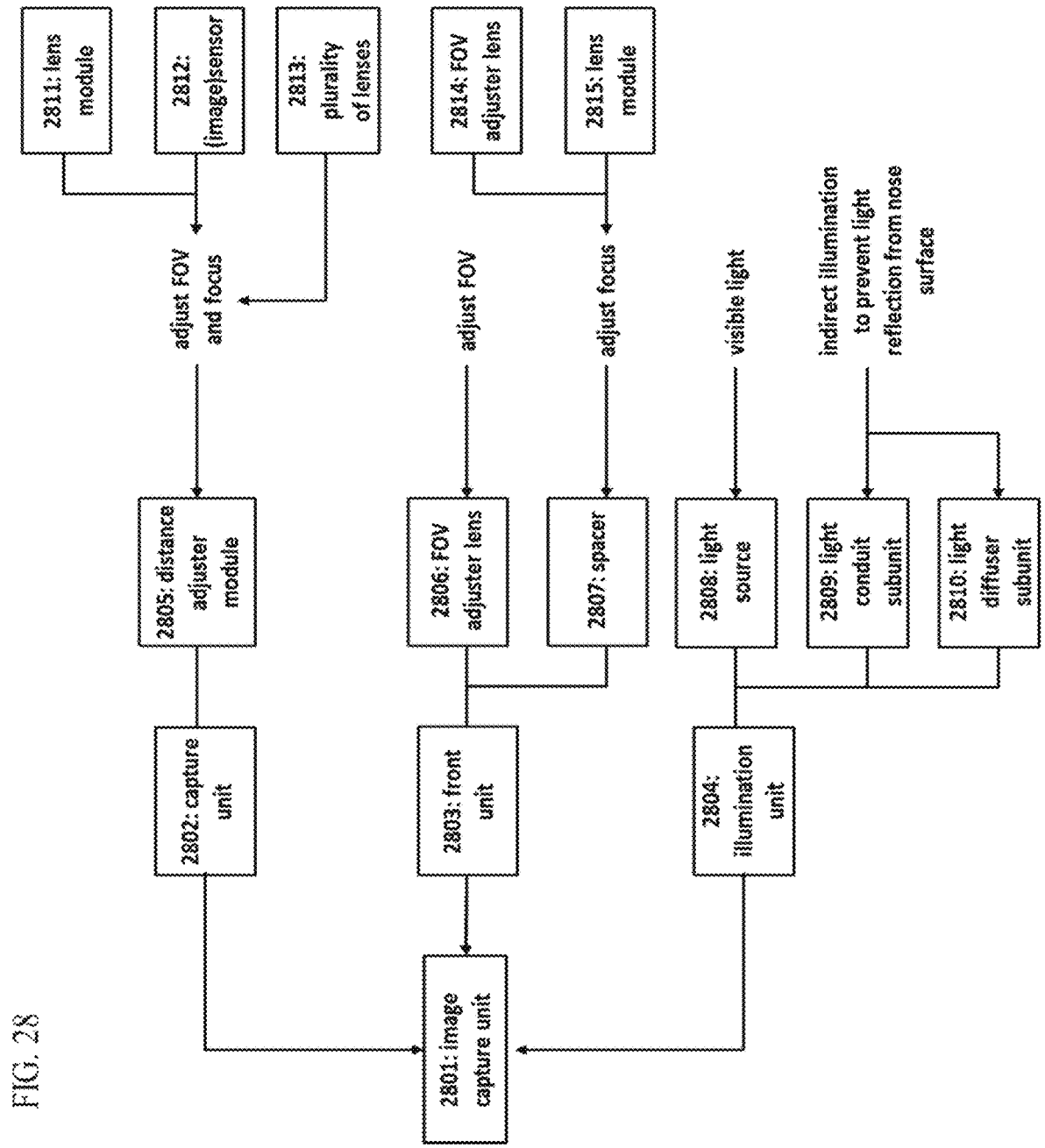
FIG. 28 is a block diagram illustrating the method of obtaining nose pattern images that are usable by the image recognition unit through the image capture unit.

In general, to obtain a high quality image, correctly setting the depth of field is important; for that purpose it is typical to adjust the aperture, FOV, focus, and the distance to the subject. The image capture unit 2801 employs a variety of ways to obtain good quality images. Within the capture unit 2802, the FOV and focus are controlled by the distance adjuster module 2805 either by moving the lens module 2811A or sensor 2812, or by moving the plurality of lenses 2813 within the lens module while the lens module 2811B and sensor 2812 stay fixed. The front unit 2803 adjusts the FOV with the FOV adjuster lens 2806, and the focus by changing distance between the FOV lens 2806 and lens module 2815 via variable spacer 2807 length. The illumination unit 2804 employs a light source 2808 of a wavelength region optimal for nose images and the light conduit subunit 2809 and light diffuser subunit 2810 for indirect illumination, which is essential to producing good quality images without obstructive reflections (FIG. 28).

Figure 29:
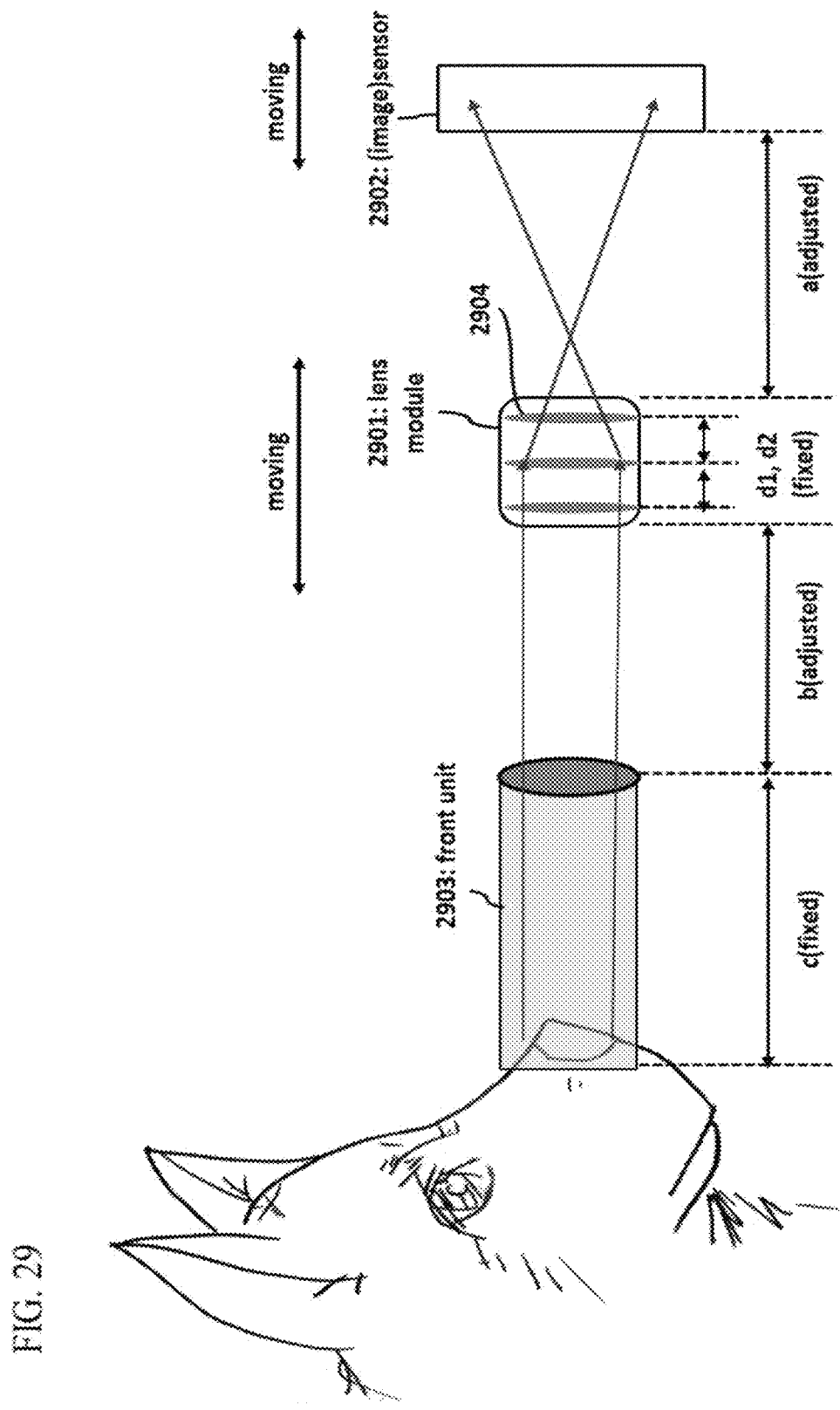
FIG. 29 is a diagram illustrating the method of adjusting the field of view and focus by moving the lens module or sensor in the image capture unit.

There are two different ways the capture unit adjusts the FOV and focus. The first method, as shown in FIG. 29, involves moving the lens module 2901 or the sensor 2902, independently or concurrently, along a linear axis using the distance adjuster module. The change in the position of the lens module 2901 or sensor 2902 changes the distance (a) between the two, and the distance (b) between the lens module 2901 and the FOV adjuster lens within the front unit 2903, thereby changing the FOV and focus. The length of the spacer 2903 is preset for the particular subject animal, and the distances (d1, d2) between the lenses 2904 in the lens module are also fixed. The values of a and b could also be set in advance for specific species so that non-professional users could easily carry out the capture process.

Figure 30:
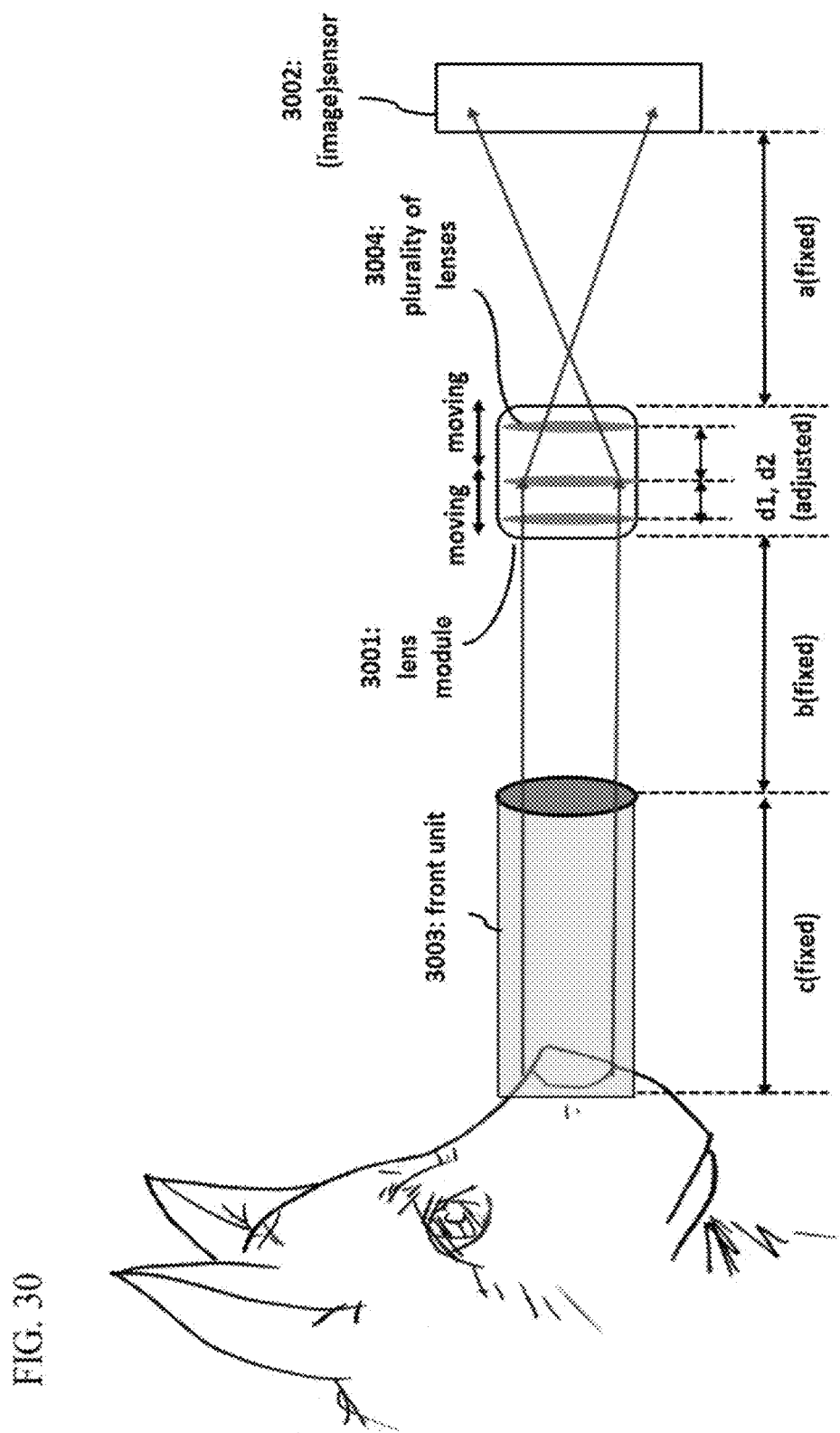
FIG. 30 is a diagram illustrating the method of adjusting the field of view and focus by moving the lenses within the lens module of the image capture unit.

The second method, as shown in FIG. 30, involves moving the lenses 3004 within the lens module along a linear axis, thereby changing the distances between the lenses (d1, d2), to change the FOV and focus. Meanwhile, the length (c) of the front unit 3003 is set in advance for the appropriate species and therefore a fixed value; and the distance (a) between the lens module 3001 and the sensor 3002, and the distance (b) between the lens module and the FOV adjuster lens in the front unit 3003 are also fixed. Moreover, the distance adjuster module may be configured to move with the lenses 3004 within the lens module so that only d1 and d2 values can be manipulated. Again, the values of a and b could also be set in advance for specific species so that non-professional users could easily carry out the capture process.

Figure 31:
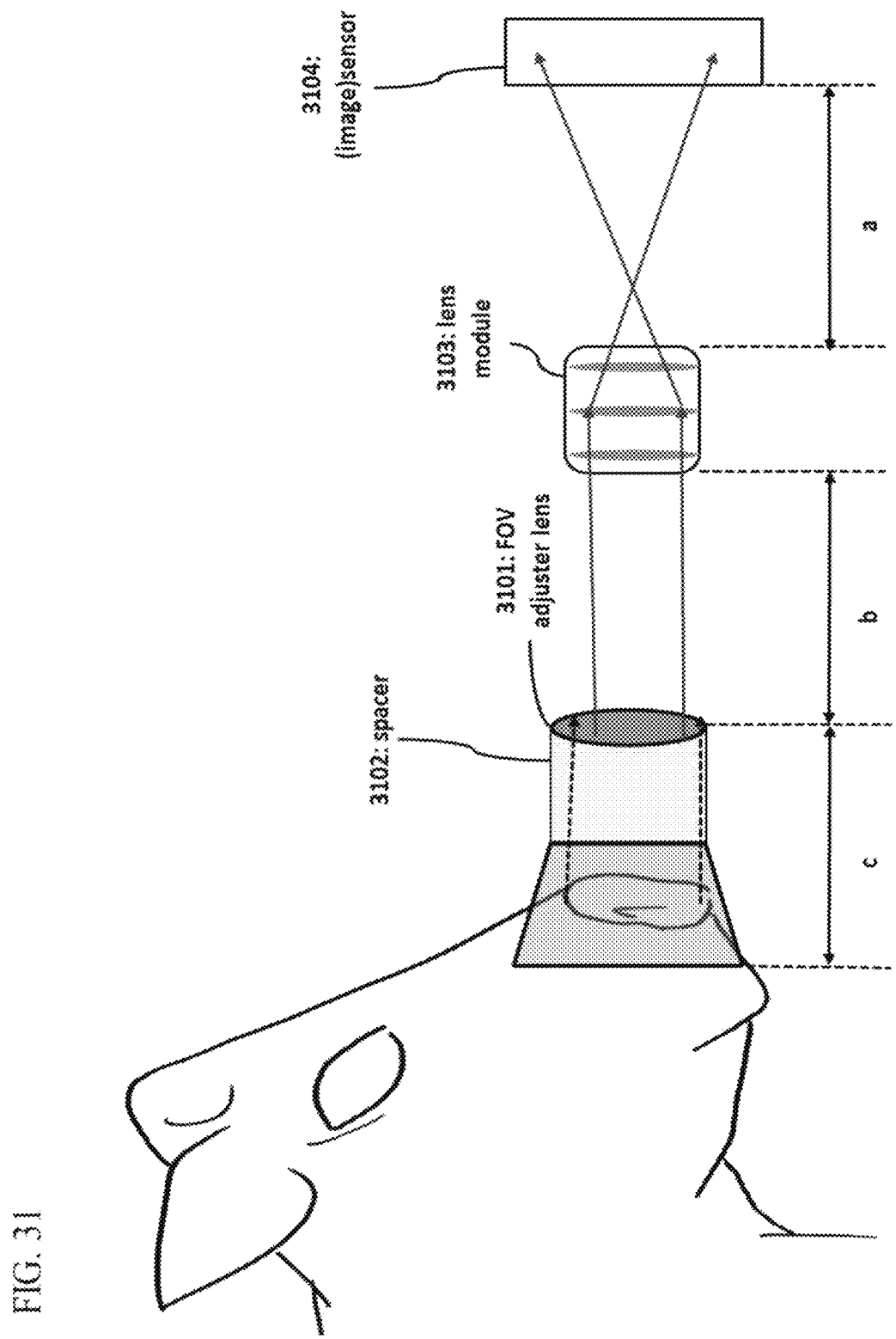
FIG. 31 is a diagram illustrating how to manipulate the field of view adjuster lens, the length of the spacer, and the type of front unit to fit the noses of larger subject animals (cow and deer).
Figure 32:
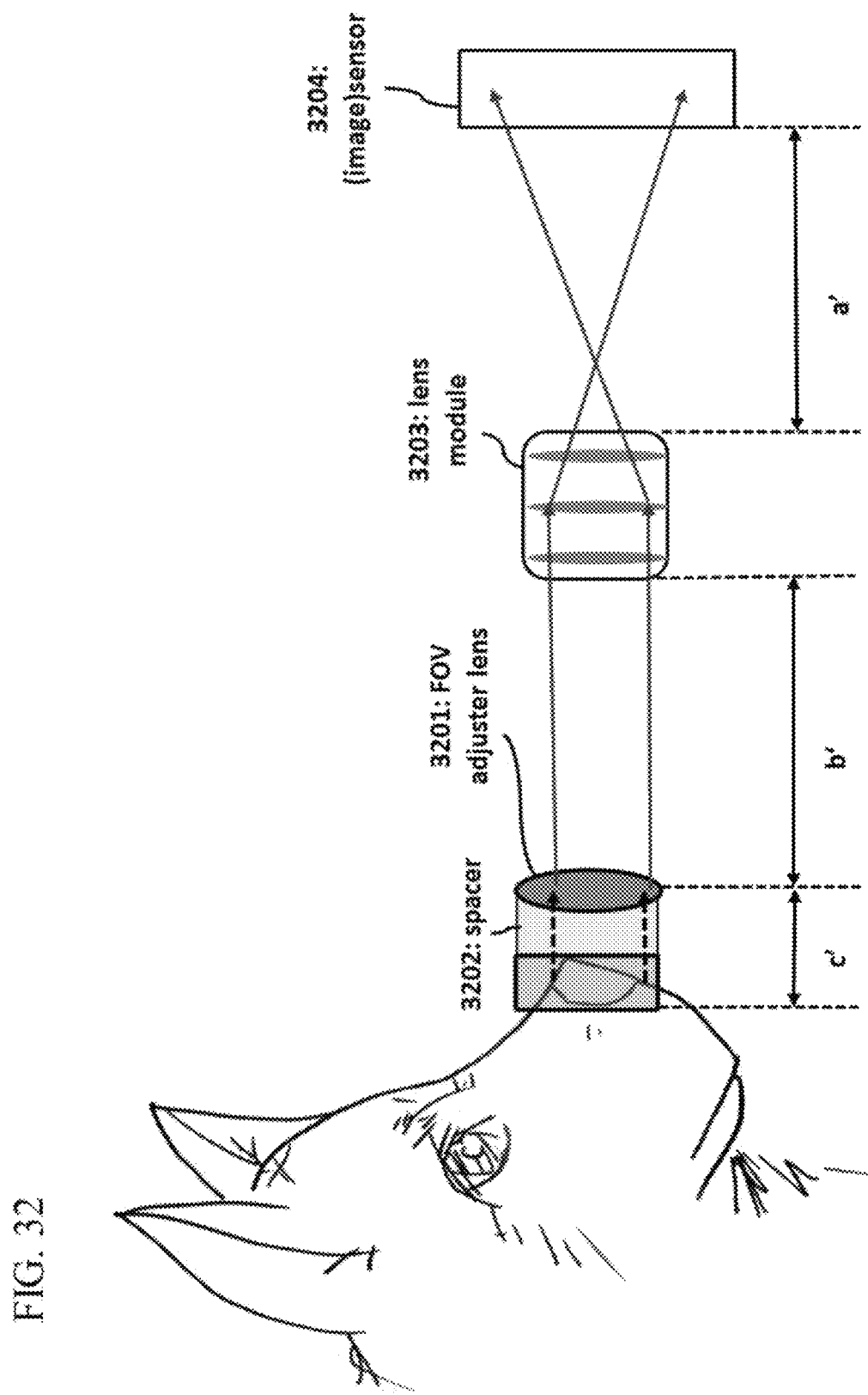
FIG. 32 is a diagram illustrating how to manipulate the field of view adjuster lens, the length of the spacer, and the type of front unit to fit the noses of medium-sized subject animals (dog).
Figure 33:
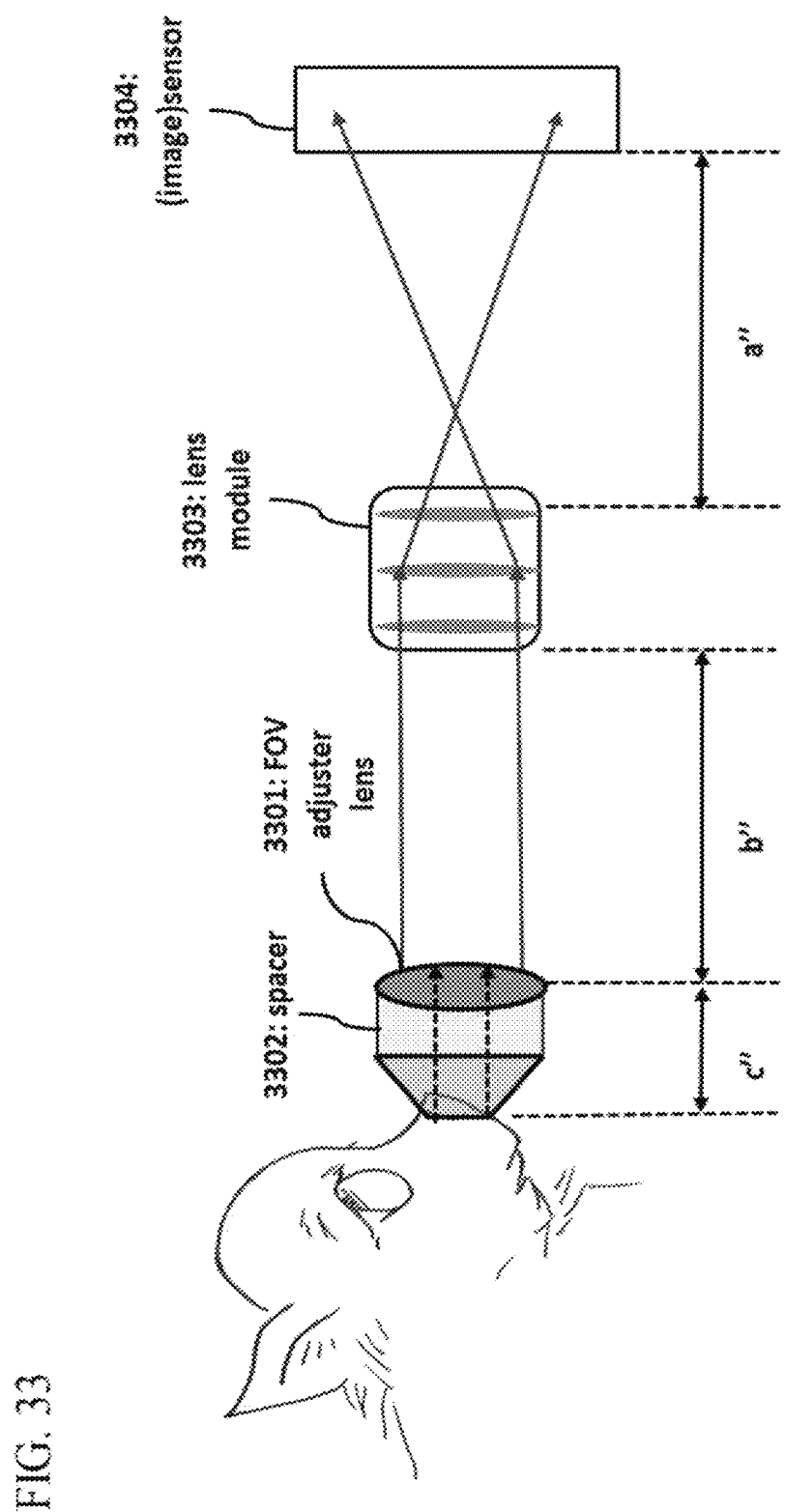
FIG. 33 is a diagram illustrating how to manipulate the field of view adjuster lens, the length of the spacer, and the type of front unit to fit the noses of smaller subject animals (cat or very small dog).

The front unit uses the FOV adjuster lens and the length of the spacer to manipulate the FOV and focus. FIGS. 31, 32, and 33 illustrate the how different combinations of the FOV adjuster lens and spacer length may be used to accommodate subject animals of different sizes. As mentioned previously, the standard FOV adjuster lens is modeled after the nose size of a typical (medium sized) dog; a reducing lens is used instead for larger noses, and a magnifying lens for smaller noses. The standard lens refers to a single or a set of lenses that allows the framing of a typical dog nose, and the reducing and magnifying lenses are made in relation to the standard. Also, the length of the spacer may be changed, depending on the nose size of the subject animal, to adjust the focus (distance).

For subject animals with a large nose surface area, like the cow in FIG. 31, using a standard lens calibrated for the size of a typical dog would not yield a large enough FOV to capture the whole nose and could negatively affect the recognition accuracy. Therefore, the FOV adjuster lens 3101 should be a reducing lens, and the spacer 3102 should be set in advance to a length appropriate to get the right focus on the subject animal. Also, since the length (c) of the spacer 3102 can change, the distance (a) between the lens module 3103 and the sensor 3104 and the distance (b) between the lens module and the FOV adjuster lens in the front unit 3101 may also change.

For subject animals with a medium-sized nose surface area, like the dog in FIG. 32, using a reducing lens would widen the FOV too much and yield images that do not show the level of detail in the nose pattern image necessary for accurate identification. Conversely, using a magnifying lens would reduce the FOV too much and not capture the whole nose, diminishing the amount of nose pattern data obtained.

Therefore, a standard FOV adjuster lens 3201 should be used for medium-sized noses, paired with an appropriately lengthened spacer 3202. Also, since the length (c') of the spacer can change, the distance (a') between the lens module 3203 and the sensor 3204 and the distance (b') between the lens module and the FOV adjuster lens in the front unit 3201 may also change.

For subject animals with a small nose surface area, like cats or the small dog in FIG. 33, using the standard lens would widen the FOV too much and yield images that do not show the level of detail in the nose pattern image necessary for accurate identification. Therefore, the FOV adjuster lens 3301 should be a magnifying lens, and the spacer 3302 should be set in advance to a length appropriate to get the right focus on the subject animal. Also, since the length (c") of the spacer can change, the distance (a") between the lens module 3303 and the sensor 3304 and the distance (b") between the lens module and the FOV adjuster lens in the front unit 3301 may also change.

Figure 34:
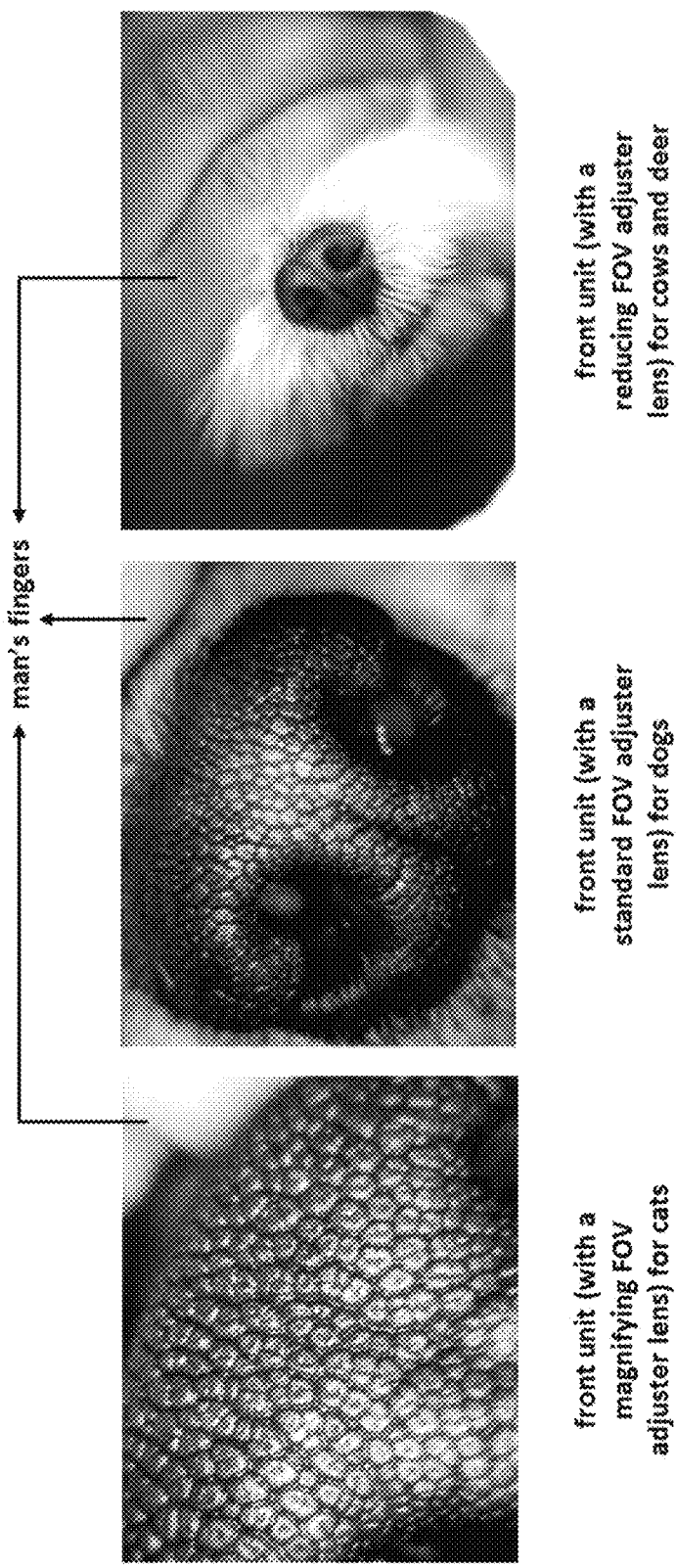
FIG. 34 is a set of photographs showing the results of using the three different types of the front unit.

FIG. 34 shows the results of using the different front unit settings on a dog, demonstrating the importance of choosing the right one; the first image was taken with the magnifying setting, the second with the standard, and the third with the reducing.

Figure 35:
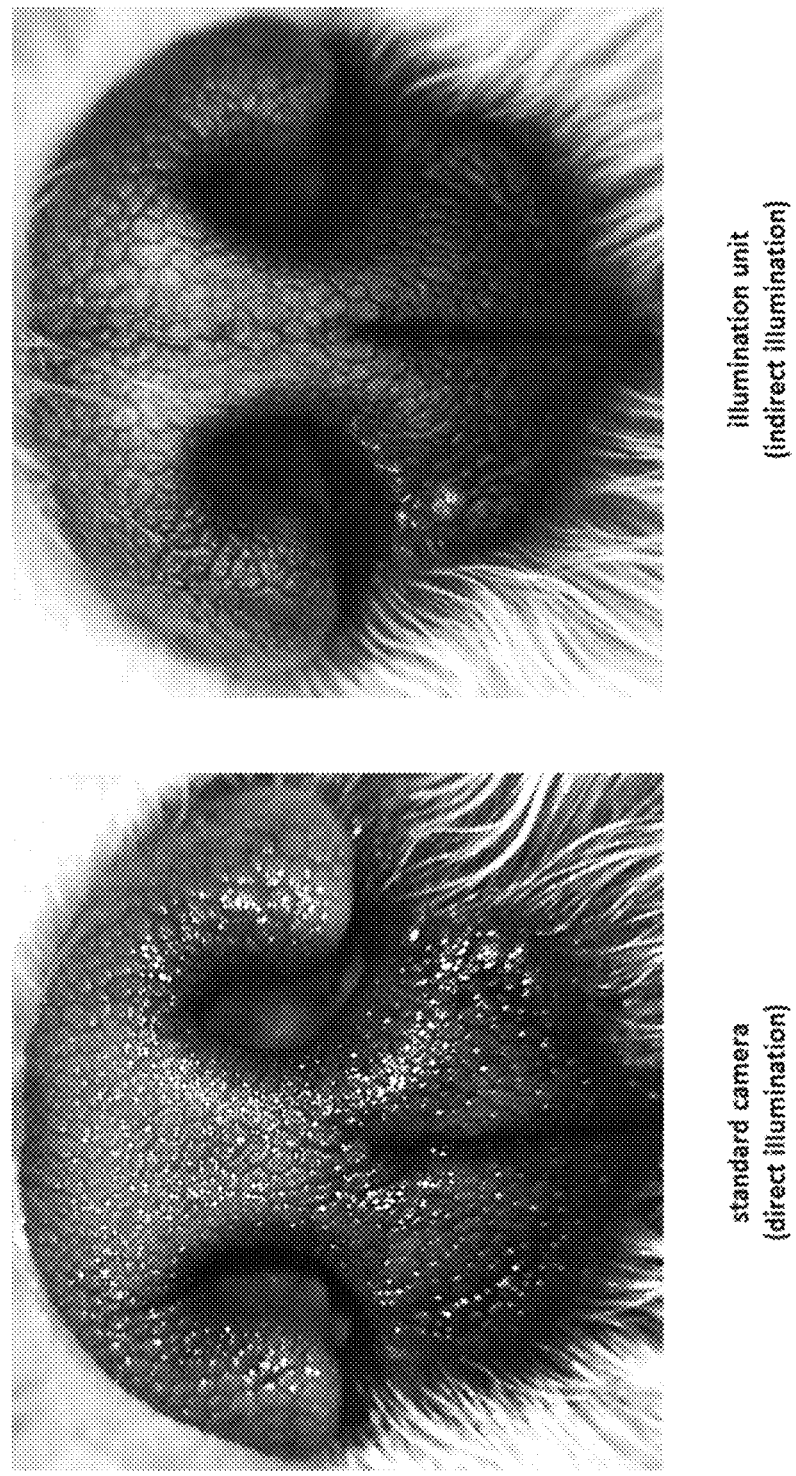
FIG. 35 is a pair of photographs comparing the results of using direct illumination of a conventional camera and the indirect illumination of the present invention to acquire the nose pattern image of the same individual.

The next step to improving the image quality is in the illumination. FIG. 35 shows a side-by-side comparison of the same dog nose image captured using the conventional direct illumination (camera flash) and the indirect illumination of the illumination unit.

The illumination unit controls the light reflections—which appear as white flecks on the left image, and are highly obstructive to accurate identification—from the moisture on the nose surface by achieving indirect illumination through the use of a special light source, light conduit subunit, and light diffuser subunit. The light source should avoid the infrared region that can be absorbed by the moisture and the UV region that can cause tissue damage, and be optimized to suit the particular characteristics of a species.

Also, FIG. 35 demonstrates that using the conventional camera flash does not help to contrast the nostril from the nose surface area, while indirect illumination results in clear boundary distinctions. This affects the ease with which the nostril boundary can be established, and thus indirectly illuminated images will generally increase the recognition accuracy.

Figure 36:
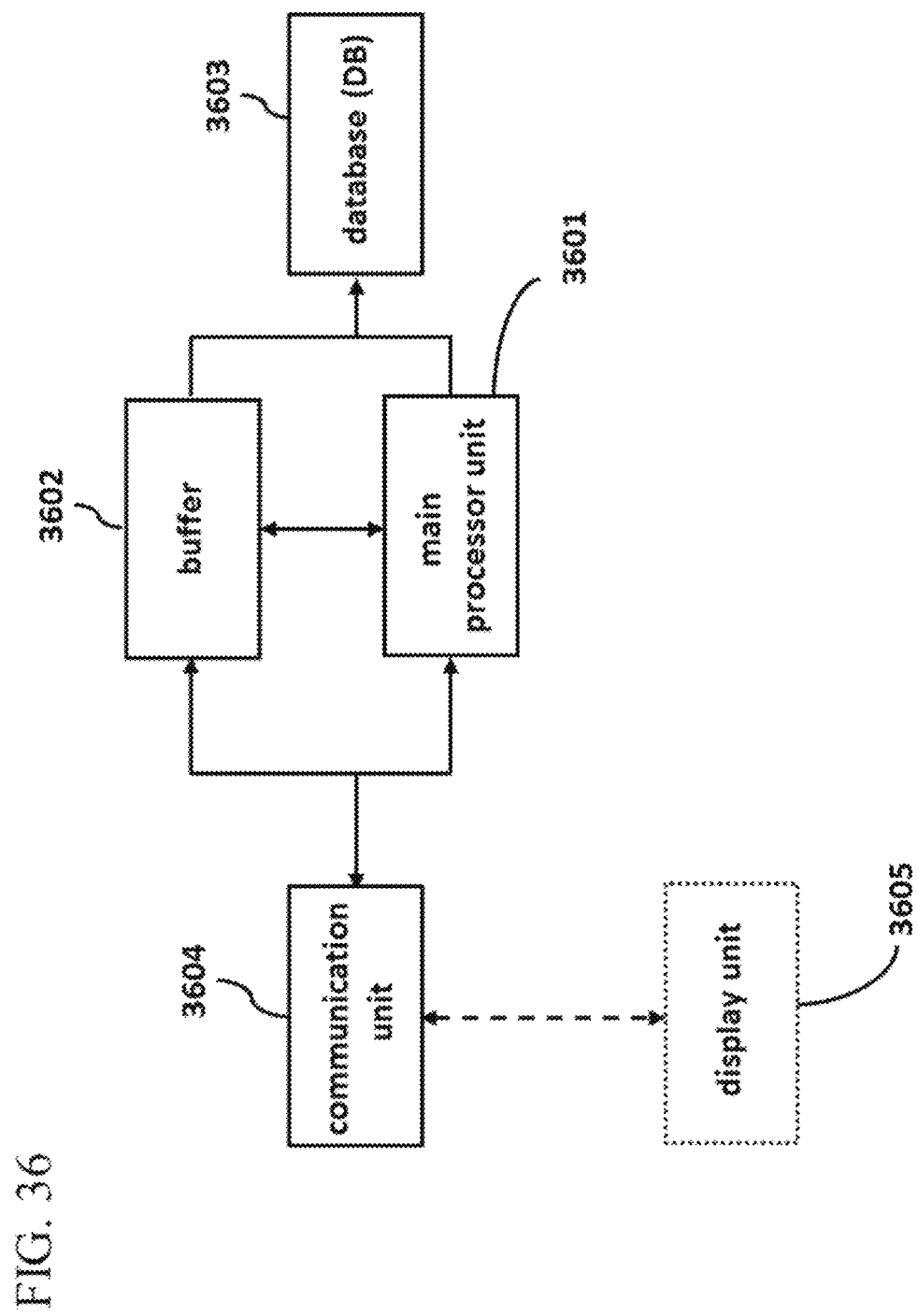
FIG. 36 is a block diagram schematically describing the image analysis unit of the present invention.

The image analysis unit analyzes the nose pattern images acquired by the image capture unit, manages various kinds of information and signals from the process, and may also be attached not only to the image acquisition unit but also the image recognition unit. As illustrated in the block diagram in FIG. 36, the image analysis unit may comprise the main processor unit 3601, the buffer 3602, the database (DB) 3603, and the communication unit 3604. Also a display unit 3605 may be added so that the operator may see the images captured by the image capture unit in real time, and select and acquire good quality images.

The main processor unit selects nose pattern images that are of sufficient quality to be used in the image recognition unit, out of all the images captured by the image capture unit. When multiple nose pattern images are obtained by the image capture unit, each image is given individual scores on specific variables, and images that pass the threshold set by the image analysis unit are selected. If none out of a particular batch meet the threshold, then that whole group is discarded and a request for a new batch is sent to the image capture unit. During this selection process, the images are evaluated on such criteria as, the amount of light reflection, sharpness, contrast ratio, ROI for capture, noise level, etc.; and only those images that pass the threshold for each variable are accepted. When more than one image out of a single batch pass the threshold the one with the highest total score (sum of individual scores) is selected, and this process may take place simultaneously as the image acquisition in the image analysis unit or the image recognition unit.

There are two types of variables: those that are not related to species-specific characteristics (A1-A3) and those that are (A4-A12). The former includes sharpness A1, contrast A2, and noise level A3; the latter includes ROI for capture A4, presence of light reflection A5, nostril location A6, sharpness of nostril image A7, contrast level of nostril image A8, noise level of nostril image A9, sharpness of the border between the nostril and ROI A10, contrast level at the border between the nostril and ROI A11, and noise level at the border between the nostril and ROI A12. Variables may be appropriately added to or subtracted from the above list depending on a subject animal species' particular characteristics (Table 1).

TABLE 1

Nose pattern image evaluation variables

| variables | Score |
|---|---|
| (A1) sharpness | a1 |
| (A2) contrast | a2 |
| (A3) noise level | a3 |
| (A4) ROI for capture | a4 |
| (A5) presence of light reflection | a5 |
| (A6) nostril location | a6 |
| (A7) sharpness of nostril image | a7 |
| (A8) contrast level of nostril image | a8 |
| (A9) noise level of nostril image | a9 |
| (A10) sharpness of the border between the nostril and ROI | a10 |
| (A11) contrast level at the border between the nostril and ROI | a11 |
| (A12) noise level at the border between the nostril and ROI | a12 |

When calculating the total score to select the best (highest scoring) image out of a batch that yields more than one image that pass the threshold, if the numerical value of sharpness is a1, and the weight factor of this is w1; contrast is a2, and w2; noise level is a3, and w3; ROI for capture is a4, and w4; presence of light reflection is a5, and w5; nostril location is a6, and w6; sharpness of nostril image is a7, and w7; contrast level of nostril image is a8, and w8; noise level of nostril image is a9, and w9; sharpness of the border between the nostril and ROI is a10, and w10; contrast level of the border between the nostril and ROI is a11, and w11; and noise level at the border between the nostril and ROI is a12, and w12; then the total score is the sum of the products of a1 and w1, a2 and w2, a3 and w3, a4 and w4, a5 and w5, a6 and w6, a7 and w7, a8 and w8, a9 and w9, a10 and w10, a11 and with and a12 and w12, is expressed using the following formula:

$$\text{Total Score} = w1*a1 + w2*a2 + w3*a3 + w4*a4 + w5*a5 + w6*a6 + w7*a7 + w8*a8 + w9*a9 + w10*a10 + w11*a11 + w12*a12$$

The above total score is the weighted sum of the individual scores, and therefore the degree of importance of a particular variable may be reflected by adjusting the weight value.

There are two ways the image acquisition unit can capture a batch of nose pattern images. When the image capture unit is not on standby in sleep mode, it is in automatic or manual capture mode. Automatic capture mode receives the threshold values for the species or breed from the DB, and compares them to the individual scores of the captured images at the main processor unit. On the other hand, in manual mode the user operates the image acquisition unit, visually makes an estimated evaluation of the individual scores of each variable and makes the capturing decision if these scores are deemed satisfactory. The sleep mode is a standby mode before entering the capture (recording) mode, and the capture mode is for the final nose pattern image acquisition. The image acquisition unit may transition from sleep mode to capture mode when the user presses a designated button on the display unit.

Figure 37:
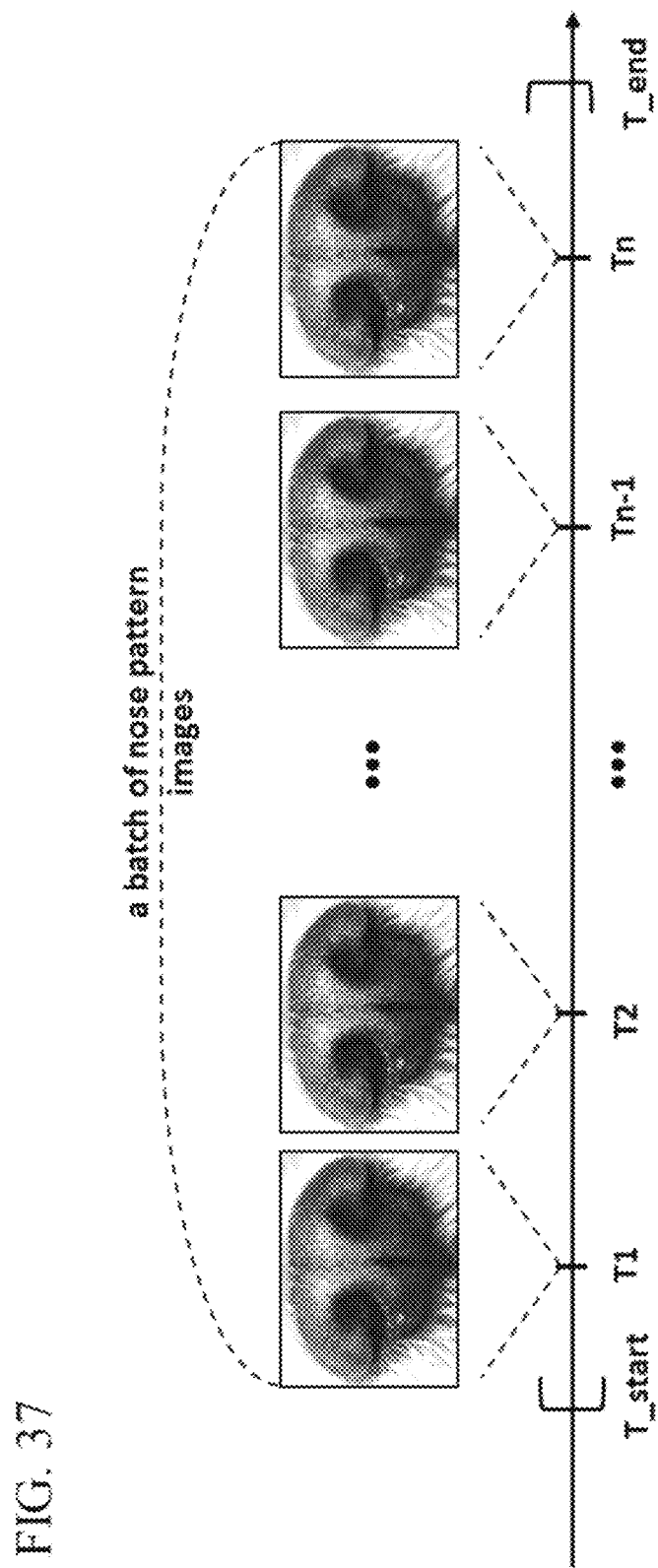
FIG. 37 is a diagram illustrating the method of nose pattern image acquisition during capture mode.

FIG. 37 illustrates the acquisition of a batch of nose pattern images in capture mode. Once in capture mode, the lens module or sensor in the capture unit moves into position according to the preset value. The transition from capture mode to sleep mode occurs when the best (threshold-passing) image is successfully selected by the main processor unit from among the batch saved to the buffer. If the time at the start of the recording is T_start and the end of the recording is T_end, then an n number of images are acquired during that time at a constant rate per second. The per second frame rate will vary depending on the resolution, and may also vary depending on the hardware configuration and the type of camera. The main processor unit may also alert the operator of the end of the capture process through a notification on the display unit.

The minimum hardware components of the main processor unit are the CPU, RAM, and nonvolatile memory (ROM, flash memory, etc.). The CPU performs all of the operations carried out by the image analysis unit. On the nonvolatile memory is mounted the resident program where the threshold values are stored, the individual scores of nose pattern images are evaluated, and the algorithm that enables the saving of the selected images and all related information to the buffer is stored. Also, when the computation for the selection of the best image is too complicated or when dealing with a very large number of images carried over from the image acquisition unit, nonvolatile memory may not be efficient for speedy processing, in which case RAM may be a useful addition to the main processor unit.

The buffer stores a variety of information that arise while the main processor unit is in the process of selecting threshold-passing images, and may consist of a flash memory or a DB. Since the DB on the buffer can be changed any time by the user, the DB of the buffer generated by the image analysis unit should preferably be stored in the flash memory. The parameter DB stores the threshold values and individual scores selected by the main processor unit in the image acquisition unit.

The communication unit relays information between the image capture unit and image analysis unit. The communication unit is tasked with the output of signals for positioning commands during capture and alerting the user of mode changes, and is thus basically equipped with a signal transmitter for outputting instruction signals. The signal transmitter may comprise one or more of the following: audible signal generator (for voice or other sounds), visual signal generator (for LED or flash), and vibration generator. Also, a display unit possibly comprising a mirror or LCD may be supplemented to enable a quick and easy review of the images obtained by the image capture unit.

The processes of the image analysis unit described thus far do not require a separate OS, but an appropriate one may be installed if there arises a need for the management of memory or other resources, time synchronization, or CPU time scheduling. Also, all of the above mentioned hardware can be mounted on a single chip for a one-chip solution (one-chip microprocessor).

Figure 38:
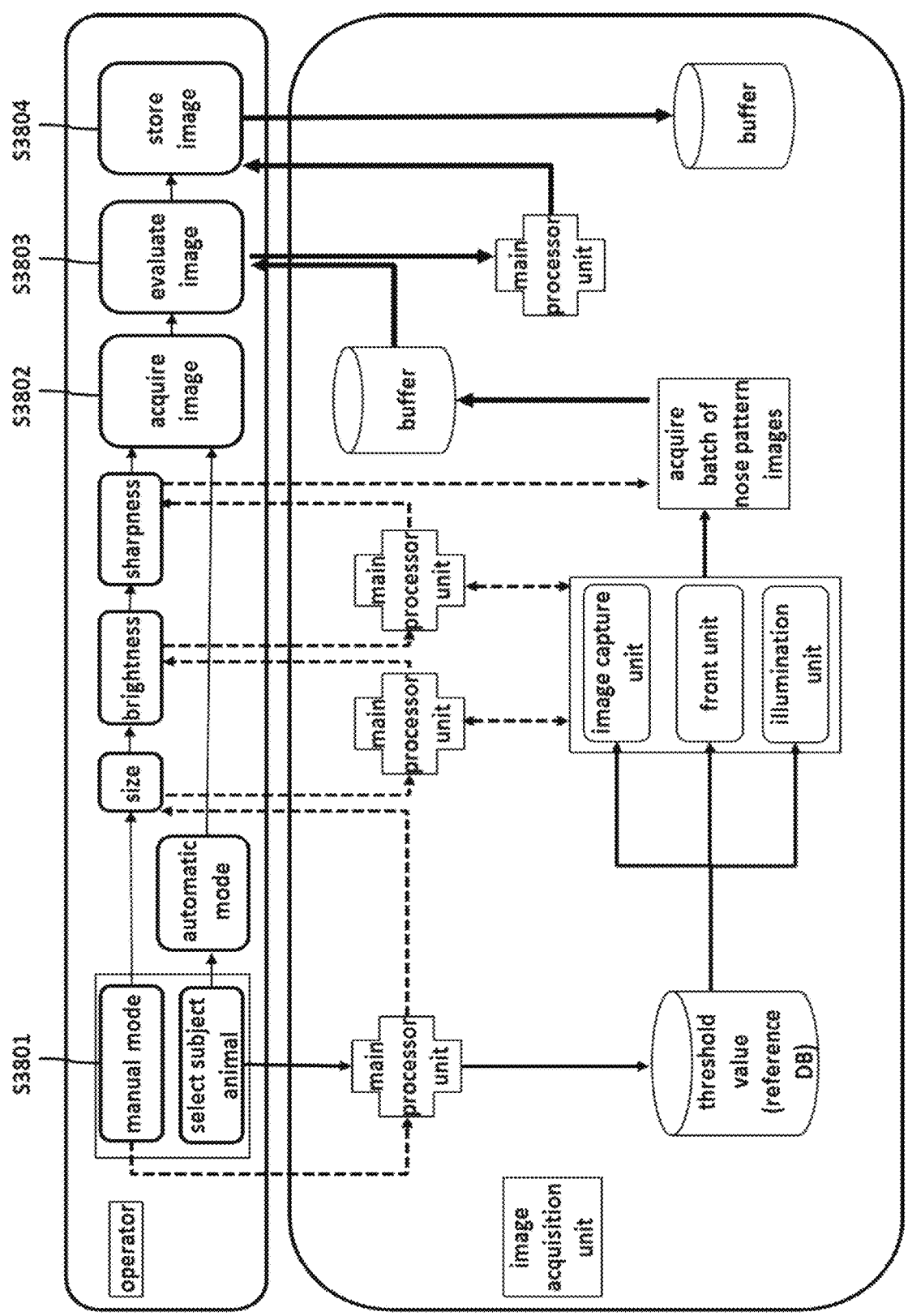
FIG. 38 is a flowchart illustrating the method of nose pattern image acquisition by the image acquisition unit.

An example of the image acquisition process is illustrated in FIG. 38; the order of events need not be limited as follows. S3801 the operator selects the species on the display unit to start the automatic mode, or chooses the manual mode; S3802 in automatic mode, once the species selection is made, pressing the capture button starts the acquisition of the batch of nose pattern images at n frames per second while the lens module is shifted about within the preset range of positions (adjusting values of a and b). In the automatic mode, the image capture unit, illumination unit and front unit are automatically adjusted to accommodate the subject animal based on the values stored in the parameter DB for FOV, focus, luminosity, etc. However, in manual mode, the operator visually evaluates the features and variables of the nose pattern images through the display unit, and selects the best image. S3803 The nose pattern images acquired from the sensor of the image capture unit are stored in the buffer, upon which the main processor unit calculates the individual scores and compares to the threshold values in the reference DB. S3804 Once the best image that passes all the thresholds is selected, it is stored in the buffer.

As previously mentioned, the image recognition unit generates processed nose pattern images and nose pattern codes for enrollment and identification. In order to successfully deal with a wide range of variances, the image recognition unit should be capable of the following: identify any individual animal with viable nose patterns, regardless of idiosyncratic characteristics; identify regardless of the extraneous physiological phenomena (such as moisture or hair, etc.); compensate for certain distortions that occur in images captured from different angles and perform accurate identification; create universal nose pattern codes for identification for any species or breed with viable nose patterns; and employ the best method of identification when performing matching within a known species or breed.

Figure 39:
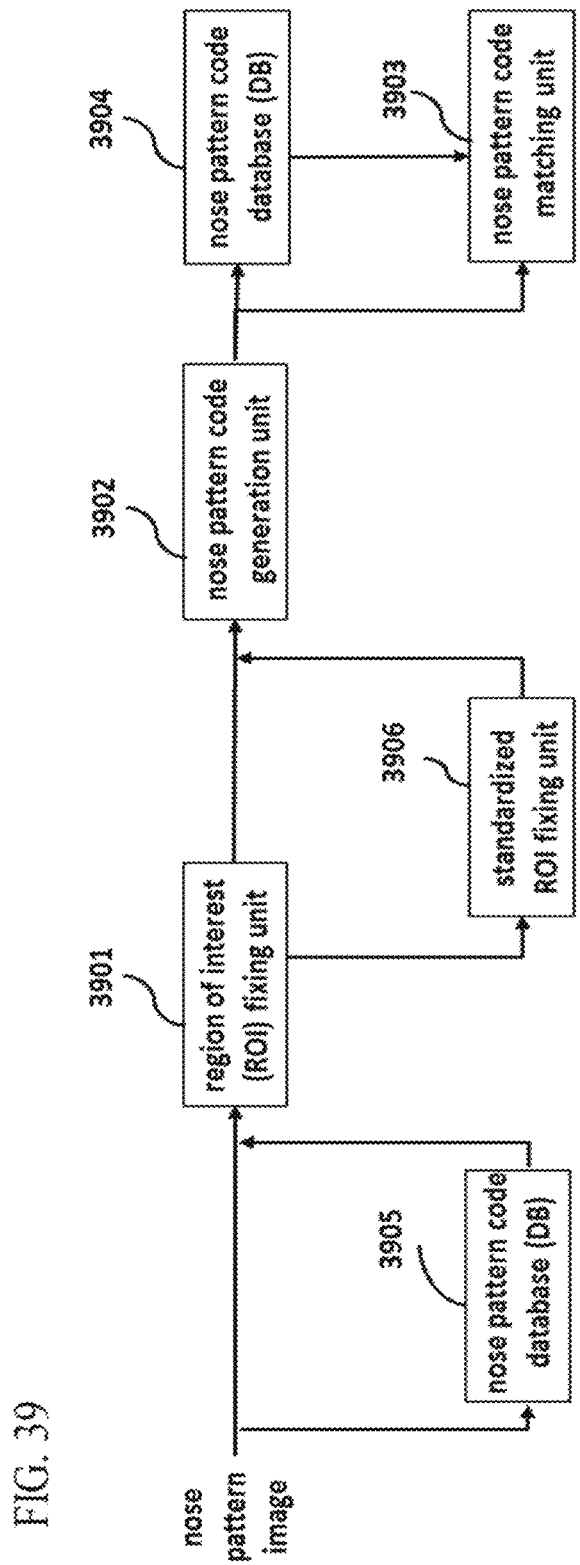
FIG. 39 is a block diagram schematically describing the image recognition unit of the present invention.

As shown in FIG. 39, the image recognition unit may comprise the region of interest (ROI) fixing unit 3901, the nose pattern code generation unit 3902 that generates the nose pattern code from the fixed ROI, the nose pattern code matching unit 3903, and the nose pattern code database (DB) 3904 where the generated nose pattern codes are stored during the enrollment and identification stage. Possible additions are the image processing unit 3905, which processes the nose pattern image, if necessary, before setting the ROI; and the standardized ROI fixing unit 3906, which standardizes the ROI before setting the ROI and generating the nose pattern code. Moreover, the aforementioned image analysis unit of the image acquisition unit may be configured into the image recognition unit.

Figure 40:
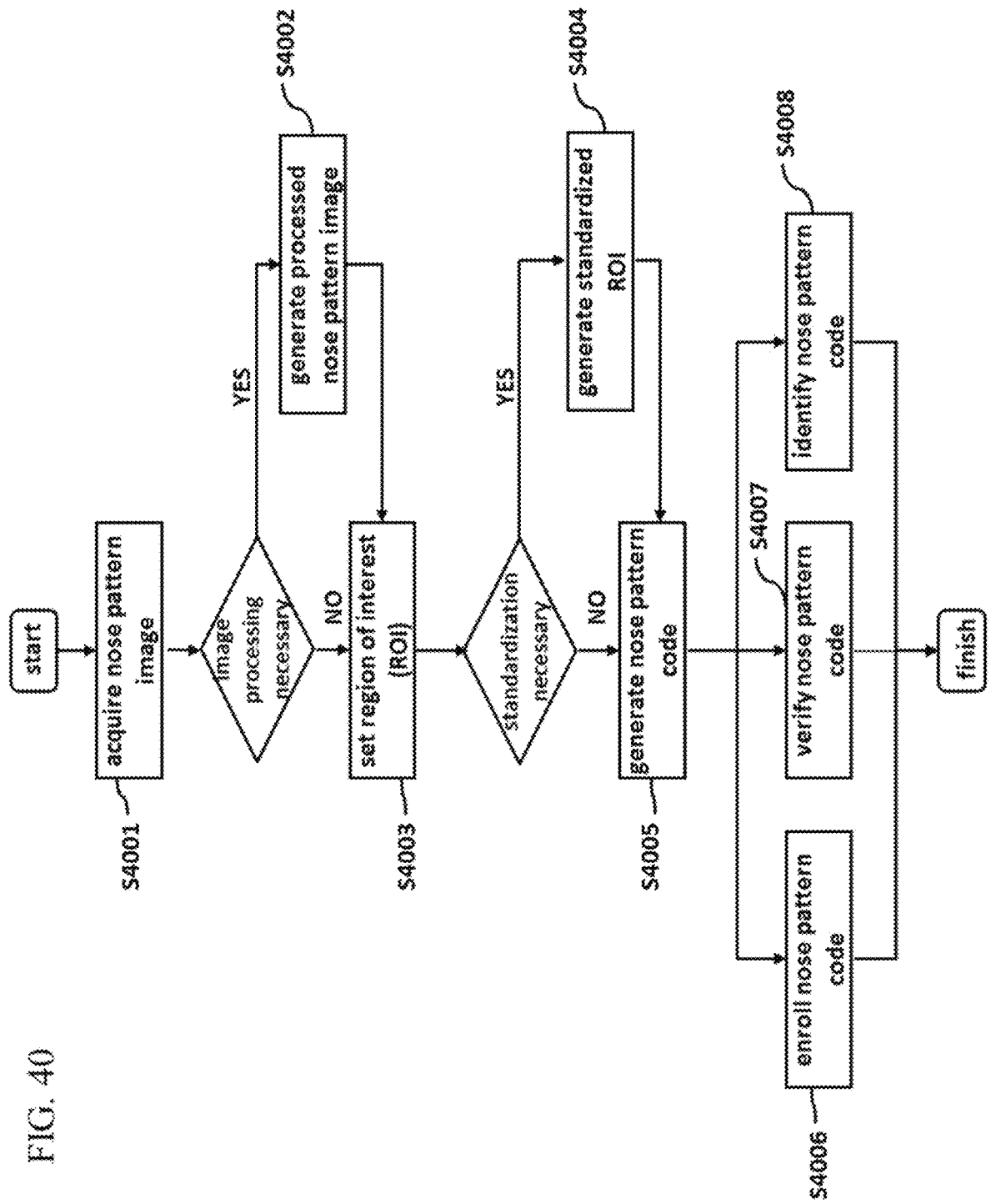
FIG. 40 is a flowchart illustrating the method of analyzing and recognizing nose pattern images.

FIG. 40 illustrates the method by which an animal nose pattern image is analyzed to be used for identification, the order of which may be modified to better suit the equipment or circumstances: S4001 acquisition of the subject animal's nose pattern image by utilizing the body stabilizer unit and image acquisition unit; S4003 setting the ROI on the (processed) nose pattern image; S4005 generating a nose pattern code from the fixed ROI; S4006 enrolling the generated nose pattern code; S4007 comparing the stored nose pattern code from the enrollment to the newly generated nose pattern code in one-to-one matching for verification; and S4008 running one-to-many matching for identification. Images acquired from S4001 that have been processed are called processed nose pattern images, and an additional step S4002 for storing them may be included. Also, the step S4004 that generates a standardized ROI from the ROI selected in S4003 may also need to occur.

The image processing unit processes the acquired nose pattern images in order to increase the identification rate, and stores the resulting image. Raw acquired images may present different levels of noise and blurring, and may require contrast adjustments to normalize the distribution of pixel values. The present invention uses the histogram equalization technique to normalize the distribution of pixel values of images. In order to adjust the distribution of pixel values, a distribution function is fixed and histogram equalization is applied to each nose pattern image to have the same fixed distribution function. Image filtering techniques may also be applied to take care of the noise and blurring issues, with Gaussian or median filters for noise level adjustment, and with a variety of low-pass filters in the frequency domain.

Moreover, sharpening techniques using derivatives can be used to accentuate the embossed nose patterns, and deconvolution techniques can be used to restore damaged images. In the present invention, except when necessary to distinguish between the raw nose pattern images and the processed nose pattern images, both will be commonly referred to as nose pattern images for the sake of simplicity.

Figure 41:
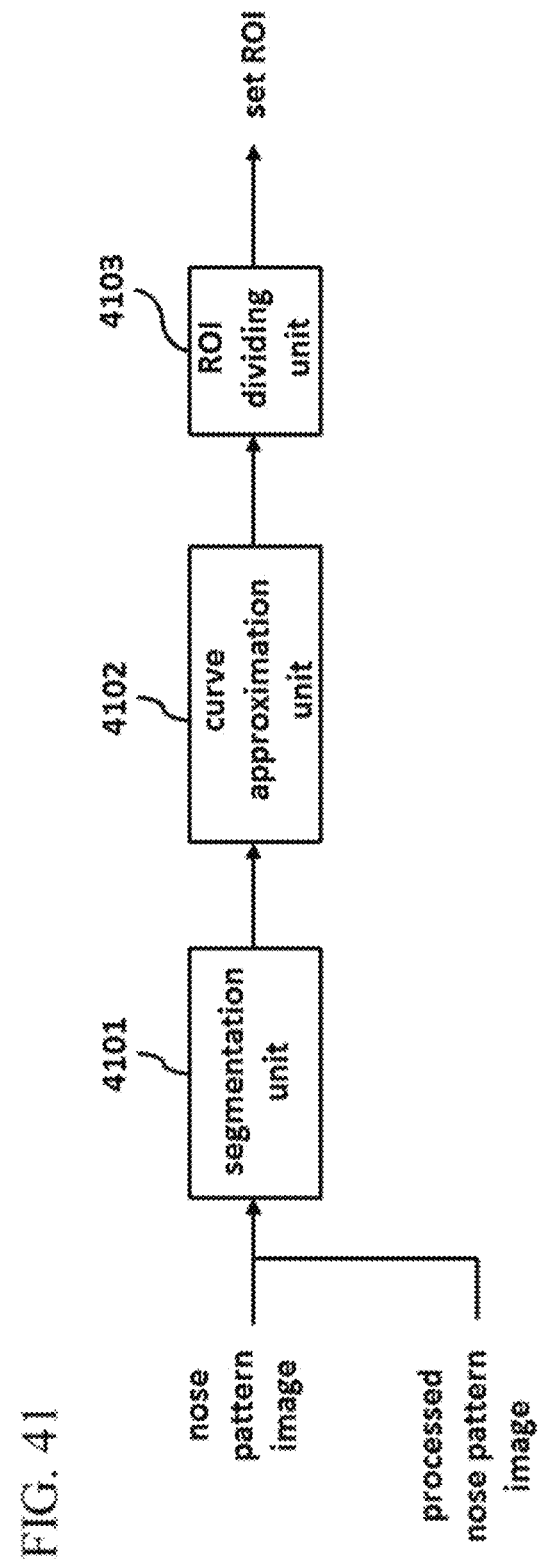
FIG. 41 is a block diagram schematically describing the region of interest fixing unit.

FIG. 41 is a schematic diagram briefly illustrating the ROI fixing unit as one embodiment of the present invention. The ROI fixing unit, as shown in FIG. 41, may comprise the segmentation unit 4101, the curve approximation unit 4102, and the ROI dividing unit 4103. The segmentation unit sets the boundaries of the nostrils, which become the basis for setting the ROI in the nose pattern image.

Figure 42:
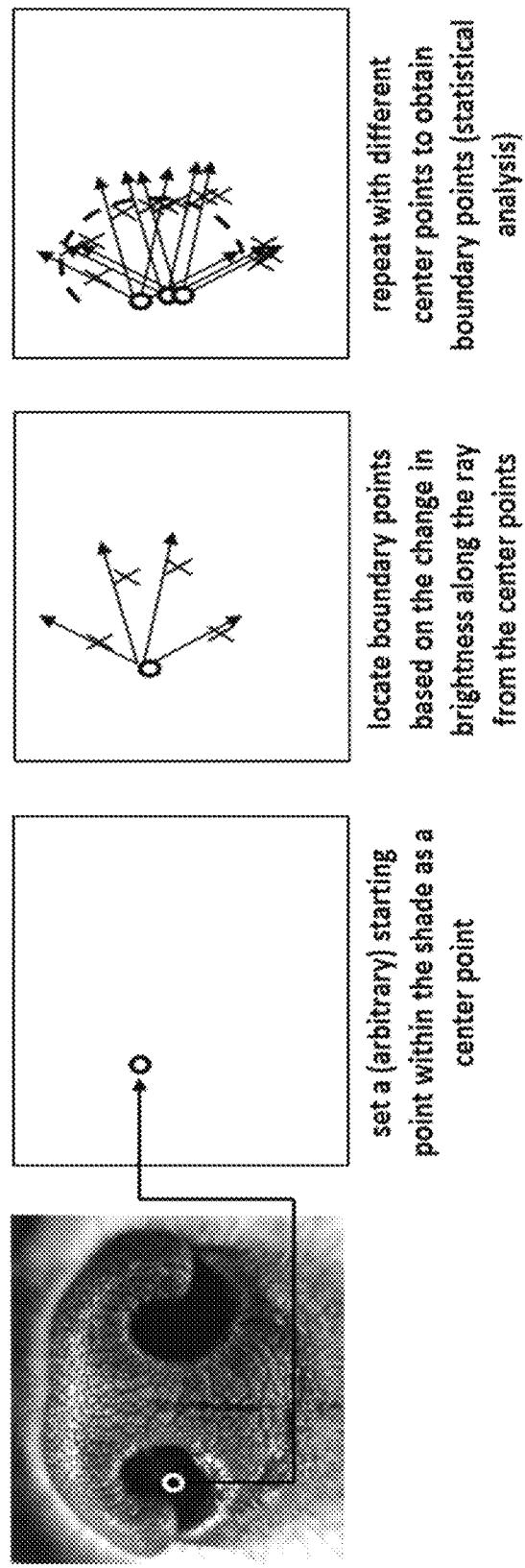
FIG. 42 is a diagram illustrating the method of finding the boundary of the nostril.

FIG. 42 is a schematic diagram illustrating how to find the nostril boundary as one embodiment of the present invention. FIG. 42 illustrates the nostril boundary setting process, where the nostrils appear as a shade due to the indirect illumination. The boundary of this shade is the basis for the nostril boundary, which may take the form of a circular or elliptical arc, etc. In order to extract the boundary points, starting with a point(s) within the shade as the center point(s), the boundary points are located based on the change in brightness along the ray from the fixed center points. Points along the rays extending in various directions that display a sharp change in brightness are marked as candidate points, and the correct boundary points are found among those candidate points based on the statistical analysis of nostril shape and location.

Using the above statistical analysis, not all of the boundary points of the nostril in various directions may be extracted resulting in that only parts of boundary points are extracted.

Sometimes, even with indirect illumination certain areas that are not part of the nostrils may appear to be inside of a similar shade, and therefore it is helpful to use multiple center points and statistical analysis utilizing the shape and location information of nostrils to prevent finding incorrect boundary points.

The curve approximation unit approximates the boundary curves of nostril boundaries using the boundary points found in the segmentation unit. In this approximation, the final approximation curve is the best curve fitting the boundary points found by various regression analyses, and it is usually a circular arc or elliptical arc.

Figure 43:
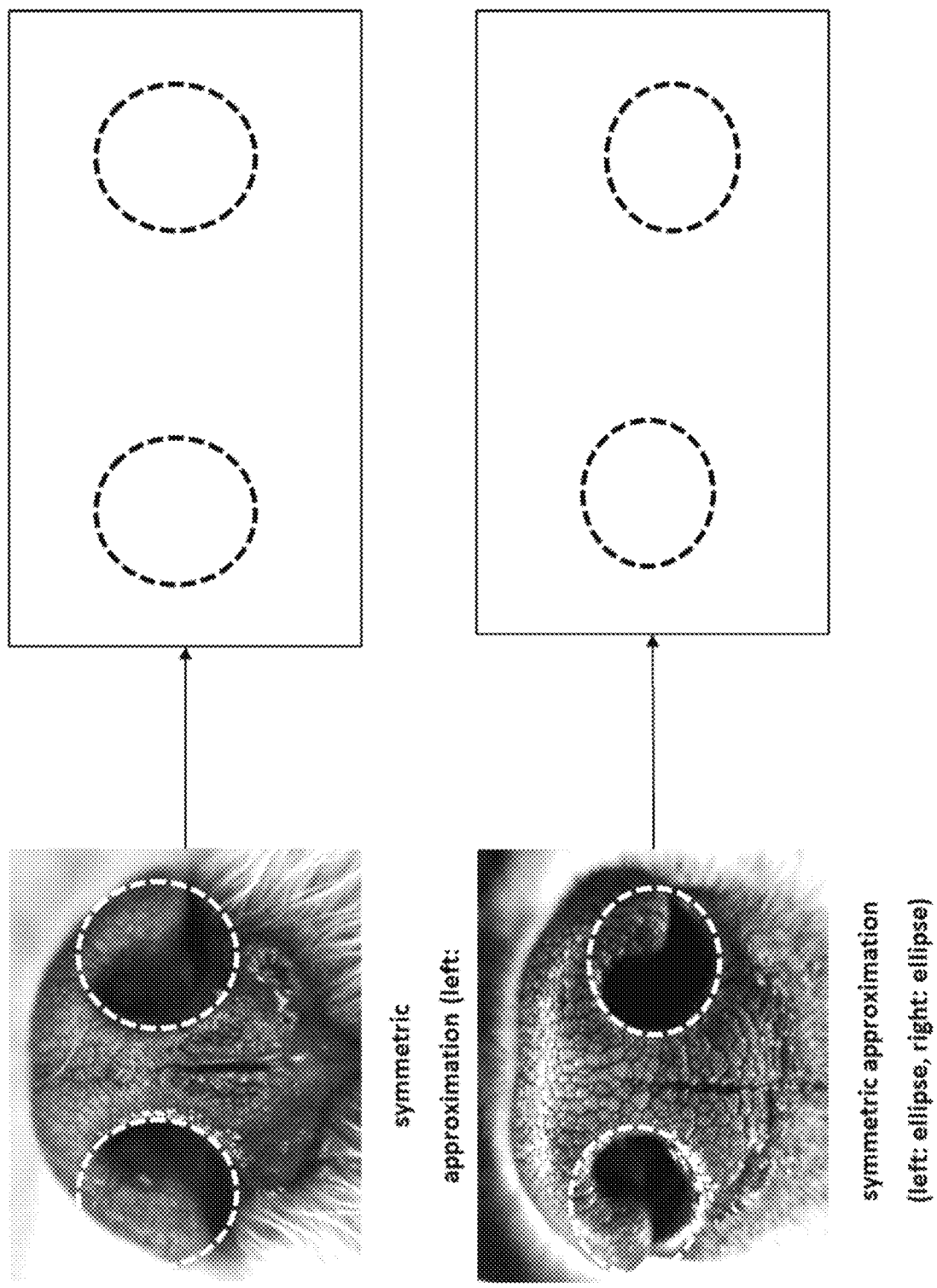
FIG. 43 is a pair of diagrams illustrating the method of approximating the boundary of the nostrils with curves (circle and ellipse, respectively).

FIG. 43 is a diagram illustrating how to approximate the nostril boundaries with circles or ellipses as one embodiment of the present invention. Although, as shown in FIG. 43, the left and right nostril boundaries can be regarded as symmetric curves when they are seen from the front of the nose, the two approximation curves can be asymmetric ellipses if the nose pattern image is taken from askew.

Also, since the curve approximation unit separately approximates the left and right nostril boundaries, the two approximation curves can have different shapes resulting in that one curve is a circle, and the other an ellipse. It is also possible that the two approximation curves are different in size although they are all either circles or ellipses.

The ROI dividing unit extracts a quadrilateral region of a nose pattern image between the two approximation curves obtained from the approximation unit. This process consists of two steps: a) the region between two approximation curves is identified and b) a quadrilateral region contained in the identified region is extracted.

(A) the First Step where the Region Between Two Approximation Curves is Identified:

FIG. 44 is a schematic diagram illustrating how to identify the region between the two approximation curves (circles or ellipses) as one embodiment of the present invention. As shown in FIG. 44, two points which are on the intersections between each approximation curve and the line segment connecting two centers of the approximation curves are located, and the two tangent lines which tangent at each located point to the approximation curve (the left tangent line is denoted by T_L, and the right tangent line by T_R) are found. These tangent lines may be perpendicular to the line segment connecting the two centers when the two approximation curves are symmetrical, and may not be perpendicular when they are not symmetrical.

The two connecting lines are then found: one line connecting two upper vertex points of the approximation curves and the other line connecting two lower vertex points (the upper line is denoted by T_U, and the lower line denoted by T_D). In this step, the two connecting lines are tangent lines which tangent to the both of the approximation curves when they are both circles and the two lines connect two upper vertex points or two lower vertex points when they are both ellipses.

(B) The Second Step where the Quadrilateral Region Between Two Approximation Curves is Extracted as the ROI:

FIG. 45 is a schematic diagram illustrating how to extract the quadrilateral region between the two approximation curves as one embodiment of the present invention. As shown in FIG. 45, the ROI is the quadrilateral region encompassed by four lines obtained in Step A. The shape and the size of the ROI may be varied depending on the relative position of the nose to the position of the image acquisition unit when the nose image is captured, and thus even the ROI from the same subject animal may be varied.

In the approximation curve unit, the two approximation curves may be obtained so that the line segment connecting the center points of the approximation curves passes the vertex points of the two approximation curves when they are both approximated by ellipses.

By assuming that two nostril boundary curves are symmetric when they are captured directly from the front, the line segment connecting the two center points of the two elliptical nostril boundary curves should pass the vertex point of each ellipse. Using this fact, the boundary curves can be approximated by ellipses so that the line segment connecting the center points of the ellipses passes the vertex points of the ellipses.

A detailed account of the standardized ROI fixing unit is given below.

Figure 46:
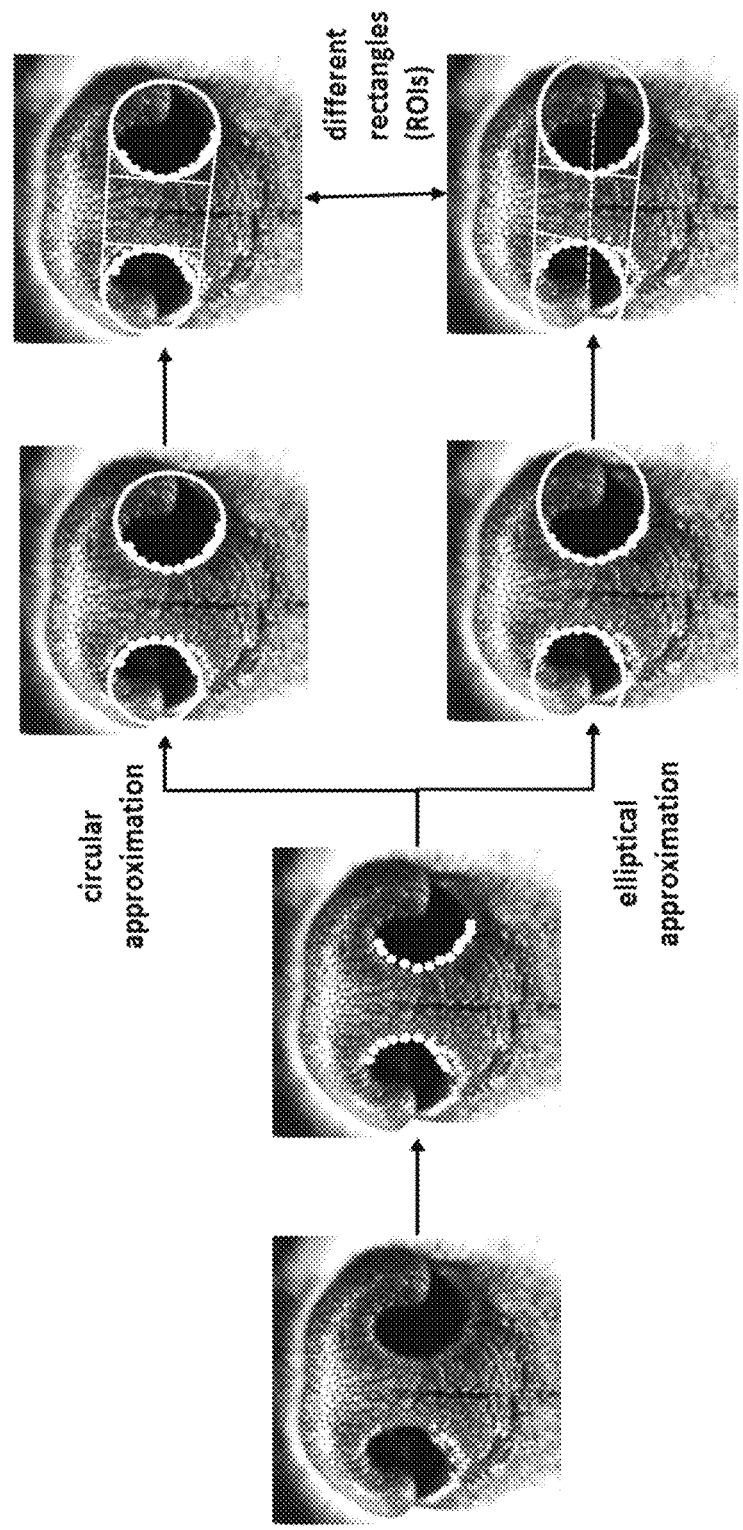
FIG. 46 is a diagram illustrating the differences in the region of interest resulting from using circular and elliptical approximation curves on the same nose pattern image.

The standardized ROI fixing unit takes care of the transformation process of the ROI acquired by the ROI fixing unit into the standardized ROI when it is necessary. FIG. 46 is a diagram illustrating how the ROI from the same nose pattern image may be varied depending on the approximation curves of the nostril boundaries. As shown in FIG. 46, the quadrilateral ROI from even the same nose pattern image may be varied when different approximation curves are used, and the above quadrilateral ROI from even the same subject animal may also be varied depending on the relative position of the nose to the image acquisition unit during capture.

To increase the identification rate, it is necessary to transform the given ROI into the standardized shape independent of the relative position of the nose and the approximation curve shapes. The standardized ROI fixing unit takes care of the transformation process of the ROI into the standard rectangular shape based on Equation (2).

Figure 47:
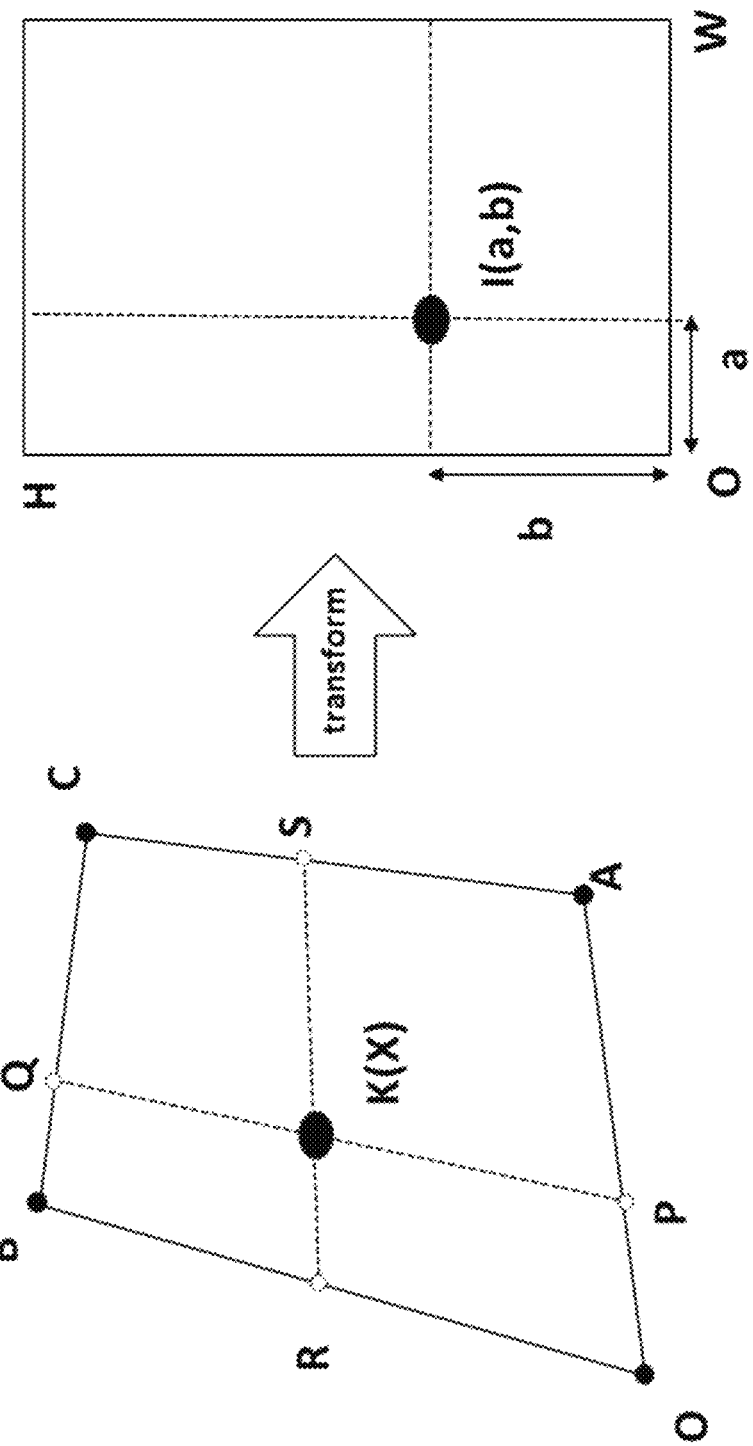
FIG. 47 is a diagram illustrating the process of generating a standardized region of interest from a previously fixed region of interest.

FIG. 47 is a diagram illustrating the transformation process of the previously determined ROI into a standardized ROI as one embodiment of the present invention. As shown in FIG. 47, a quadrilateral ROI with four vertices O, A, B, C is transformed into a rectangular area of width W and height H by Equation 2.

$$P = O + \frac{a}{W}(A - O), Q = B + \frac{a}{W}(C - B), \qquad \text{(Equation 2)}$$

$$R = O + \frac{b}{H}(B - O), S = A + \frac{b}{H}(C - A)$$

$$X = P + \frac{b}{H}(Q - P) = R + \frac{a}{W}(S - R)$$

In this transformation, the coordinates of the corresponding point X in the ROI may not be integral values in contrast to the point in the standardized ROI which has integral coordinates a and b. In this case, the brightness value K(X) of point X can be interpolated from the nearby pixel values and the intensity of the point (a, b) is defined by Equation 3.

$$I(a,b)=K(X) \qquad \text{(Equation 3)}$$

By the above transformation, various shapes of the quadrilateral ROI can be transformed into a rectangular shape.

In the present invention, except when necessary to distinguish between the ROI and the standardized ROI, both will be commonly referred to as ROIs for the sake of simplicity. A detailed account of the nose pattern code generation unit is given below.

Figure 48:
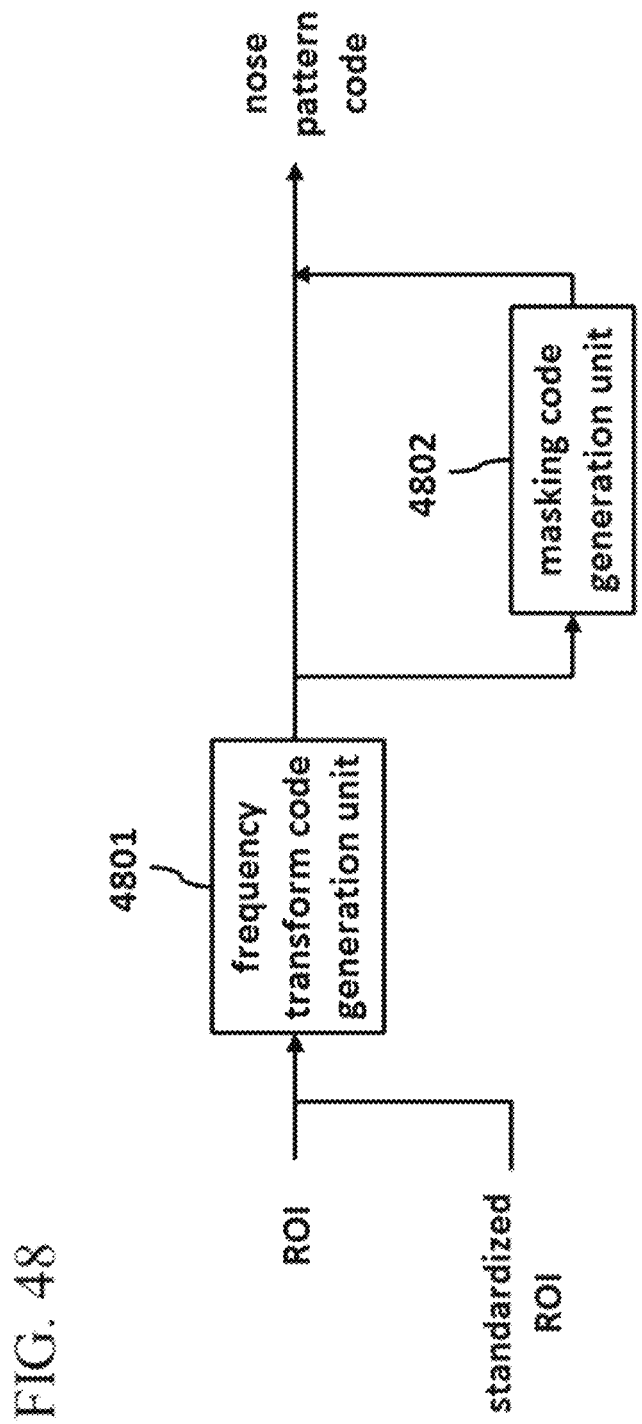
FIG. 48 is a simplified block diagram describing the nose pattern code generation unit.

FIG. 48 is a simplified block diagram describing the nose pattern code generation unit as one embodiment of the present invention. As shown in FIG. 48, the nose pattern code generation unit may comprise the frequency transform code generation unit 4801 and the masking code generation unit 4802.

A nose pattern code consists of a frequency transform code and a masking code which are generated by the frequency transform code generation unit and the masking code generation unit, respectively. A detailed account of the nose pattern code generation method is given below.

Figure 49:
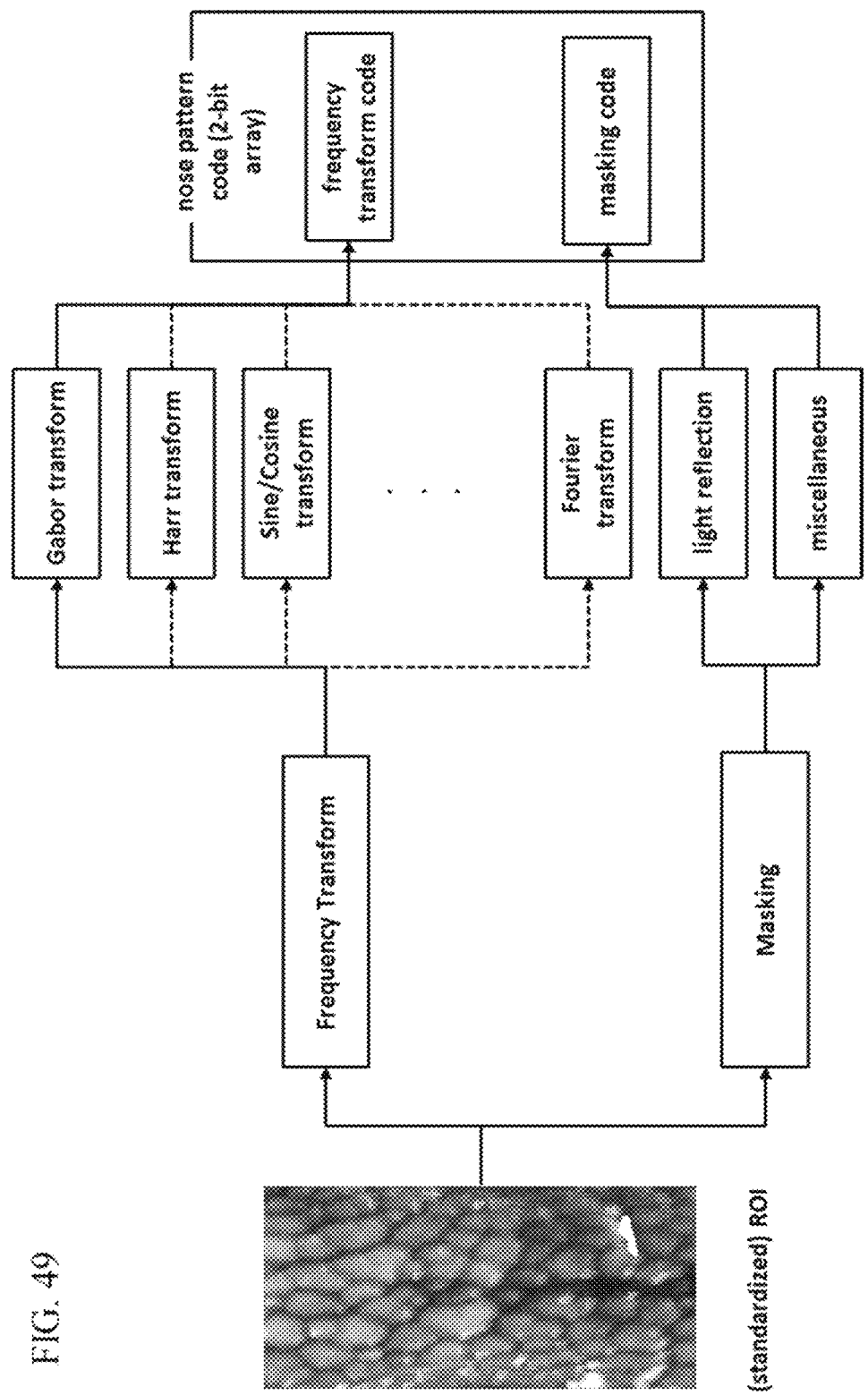
FIG. 49 is a block diagram illustrating the process of generating nose pattern codes from the region of interest.

FIG. 49 is a block diagram illustrating the process of generating nose pattern codes from the ROI. As shown in FIG. 49, a nose pattern code consists of the frequency transform code generated in the frequency transform code generation unit and the masking code generated in the masking code generation unit using the ROI. The nose pattern code is a 2-bit array and its component value is determined by predetermined frequency transform methods and parameters of the transforms.

The predetermined frequency transform methods may include several frequency methods including Gabor transform, Haar transform, Gabor Cosine transform, Gabor Sine transform, Sine transform, Cosine transform, and various wavelet transforms.

In the present invention, different frequencies for real and imaginary parts of Gabor transform may be used. Also, either of the real part of Gabor transform (Gabor Cosine transform) or the imaginary part of Gabor transform (Gabor Sine transform) may be used alone. The choice of frequency transform methods in the nose pattern code generation unit may be determined according to the performance and the processing speed of the image recognition unit.

Below is a detailed account of the process of generating frequency transform codes from the ROI in the frequency transform code generation unit.

Figure 50:
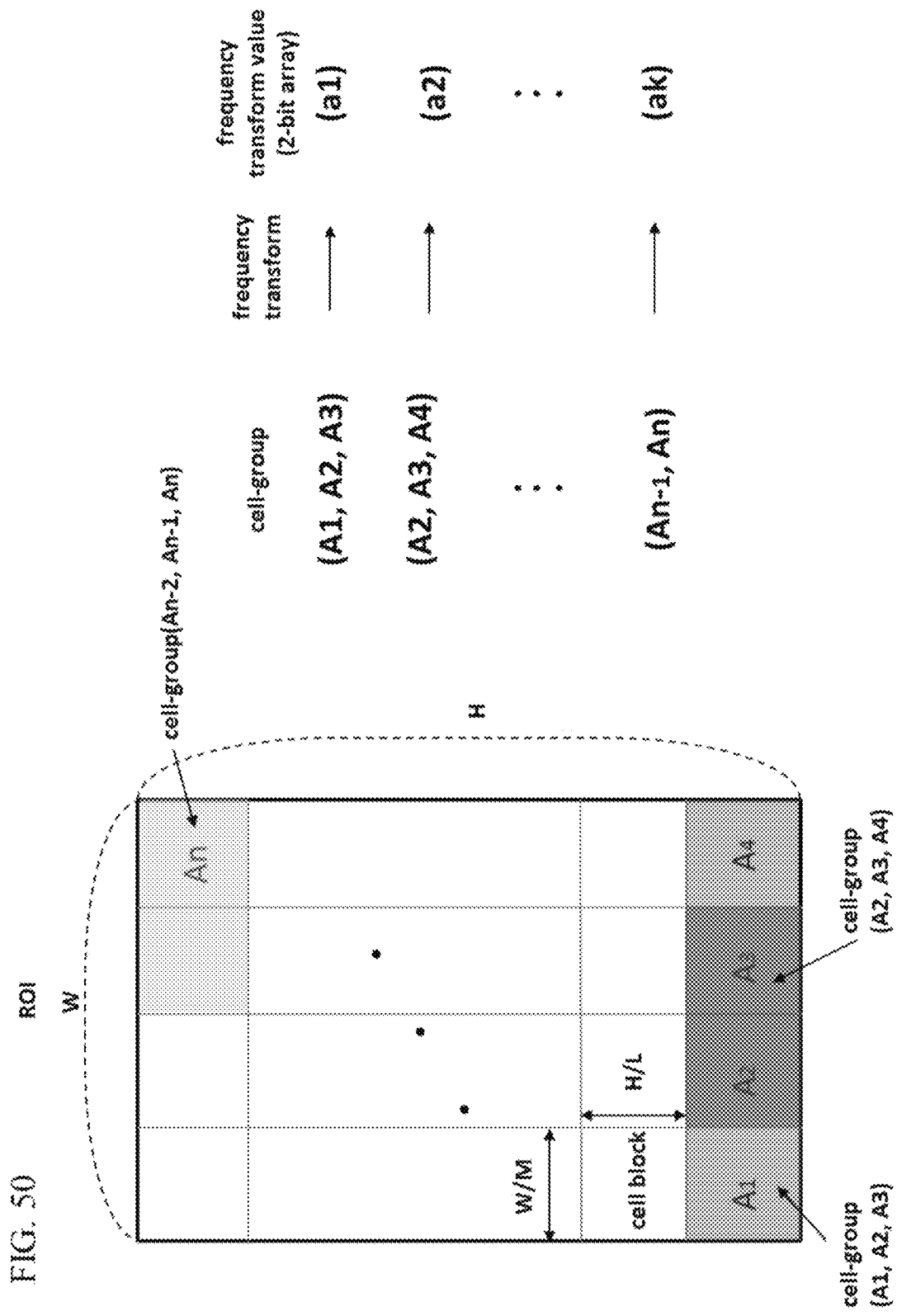
FIG. 50 is a diagram illustrating how to divide the region of interest into smaller cell blocks of specified dimensions, from which frequency transform codes are generated.

FIG. 50 is a diagram illustrating how to divide the ROI into smaller regions with specified dimensions which are called cell blocks and how frequency transform codes are generated from those cell blocks. Each cell block may consist of one or more pixels. When the size of the given nose image is large, a group of pixels may be reduced into one pixel by averaging the values in the group. The group of pixels may be regarded as a cell block in this process. In other words, each cell block may be represented by one pixel value using proper methods.

As shown in FIG. 50, the ROI with width W and height H is divided into n (=M*L) equally sized cell blocks. The total number of cell blocks and the size of each cell block may be varied depending on the size of the nose image, the breed of the subject animal, the frequency transform methods, parameters used in the frequency transform methods, etc.

Also the frequency transform codes consist of frequency transform values, each of which is obtained from a group of cell blocks called a cell-group as shown in FIG. 50. In other words, a cell-group is the basic unit for obtaining frequency transform codes. Two different cell-groups may include some common cell blocks.

The number of cell-groups and the number of cell blocks in each cell-group may be varied depending on the breed of the subject animal, frequency transform methods, parameters used in the frequency transform methods, etc. Each frequency transform value from a cell-group is a binary bit value (0 or 1) calculated based on the predetermined frequency transform method and parameters.

While, in most cases, each cell-group gives only one frequency transform value so that the length of the frequency transform code is equal to the number of cell-groups, multiple frequency transform values may be obtained from one cell-group with multiple frequency transform methods and parameters. Also, with some frequency transform method, multiple frequency transform values may be obtained from each cell-group even with one parameter.

For example, by Gabor transform, two frequency transform values—the real and imaginary parts of the frequency transform—are generated from each cell-group. While frequency transform methods vary in the way the binary bit value from each cell-group is obtained, they are essentially the same except their transformation formula and parameters. Thus, the transformation formula and its parameters are explicitly considered only of Gabor transform, Gabor Cosine transform and Gabor Sine transform in the present invention.

Below is a detailed account of the process of generating frequency transform codes from the ROI described above in the case of Gabor transform, Gabor Cosine transform and Gabor Sine transform.

Example

Gabor Transform, Gabor Cosine Transform, Gabor Sine Transform

The frequency transformation method of Gabor transform is given by Equation (4) with its parameters, Gabor Cosine transform and Gabor Sine transform each, calculates the binary bit values of frequency transform codes using Equation (5) and Equation (6), respectively.

$$V = \int_0^W \int_0^H I(a,b) e^{-i\omega_x(a-a_0)} \qquad \text{(Equation 4)}$$
$$e^{-i\omega_y(b-b_0)} e^{-\frac{(a-a_0)^2}{\alpha^2}} e^{-\frac{(b-b_0)^2}{\beta^2}} db\, da$$

$$\text{Re}(V) = \int_0^W \int_0^H I(a,b) e^{-\frac{(a-a_0)^2}{\alpha^2}} \qquad \text{(Equation 5)}$$
$$e^{-\frac{(b-b_0)^2}{\beta^2}} \cos(\omega_x(a-a_0) + \omega_y(b-b_0)) db\, da$$

$$\text{Im}(V) = -\int_0^W \int_0^H I(a,b) e^{-\frac{(a-a_0)^2}{\alpha^2}} \qquad \text{(Equation 6)}$$
$$e^{-\frac{(b-b_0)^2}{\beta^2}} \sin(\omega_x(a-a_0) + \omega_y(b-b_0)) db\, da$$

In Equations (4), (5) and (6), I(a,b) denotes the brightness of the pixel in the ROI at the position of (a,b) and represent coordinates of a point in the ROI. Also, $\alpha$, $\beta$ are parameters of Gabor transform to determine how large is the effective region to consider when calculating the frequency transform, and are parameters to determine the horizontal frequency and the vertical frequency, respectively.

Although the integration is done continuously in Equations (4), (5) and (6) in the present invention, the integration is approximated by the sum of integrand values at finite lattice points.

Figure 51:
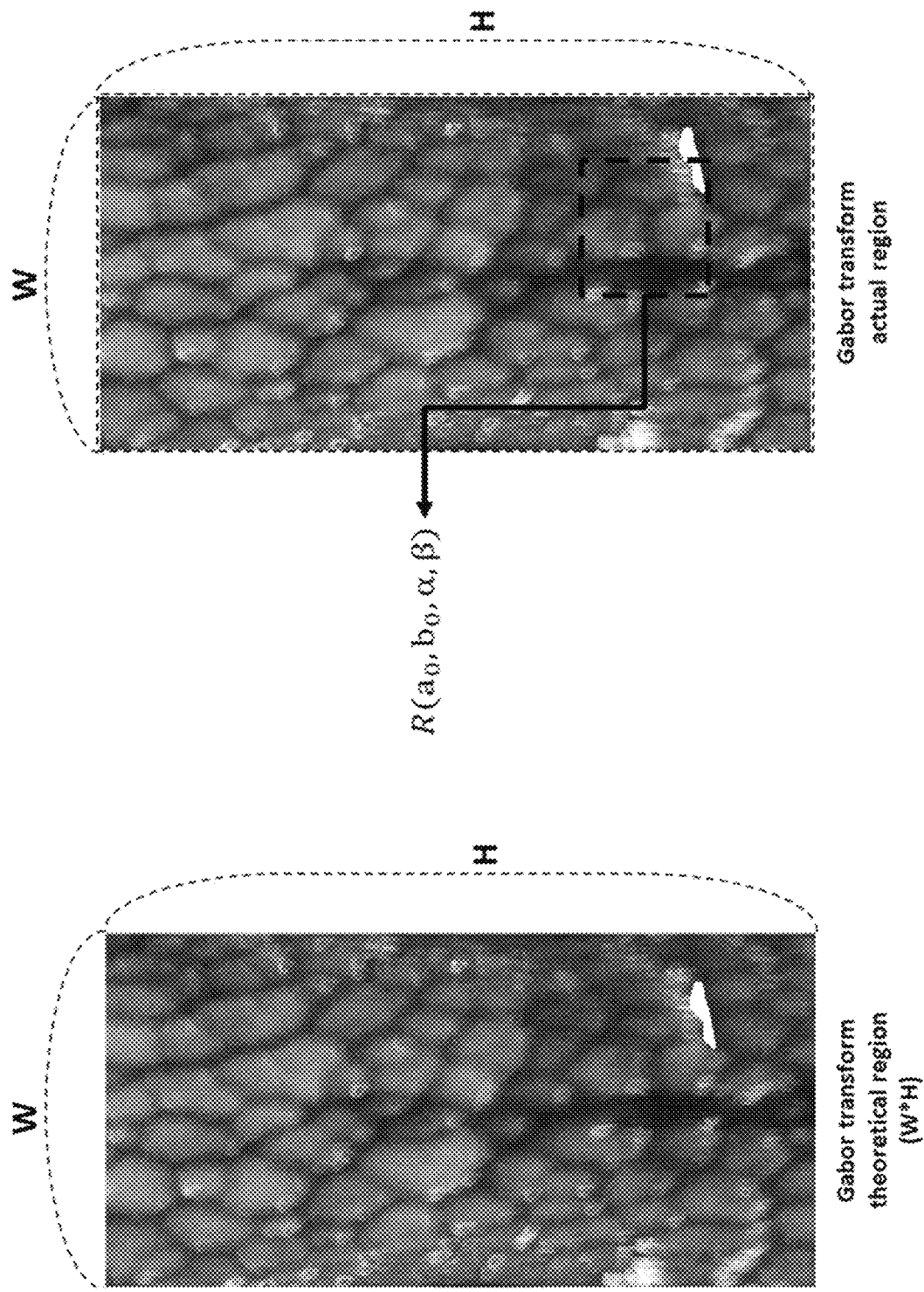
FIG. 51 is a diagram illustrating the comparison of a theoretical calculation area and the actual area when generating the frequency transform code using Gabor transform, Gabor cosine transform, Gabor sine transform, etc.

Below is a detailed account of the process of approximating the integrations in Equations (4), (5) and (6). The region of integration in Equations (4), (5) and (6) is different from the actual region to consider when approximating the integration. FIG. 51 is a diagram illustrating how the two regions differ when using Gabor transform, Gabor Cosine transform, Gabor Sine transform as one embodiment of the present invention.

As shown in FIG. 51, the theoretical region of integration in Equations (4), (5) and (6) is the whole ROI, but the actual region to consider when approximating the integration is restricted to the region where the value of $$e^{-\frac{(a-a_0)^2}{\alpha^2}} e^{-\frac{(b-b_0)^2}{\beta^2}}$$

is greater than the given threshold since the integration value has little difference with those pixels in the region where the value of $$e^{-\frac{(a-a_0)^2}{\alpha^2}} e^{-\frac{(b-b_0)^2}{\beta^2}}$$

is smaller than the given threshold. In this respect, cell-groups may be formed so that each cell-group only consists of cell blocks where the value of $$e^{-\frac{(a-a_0)^2}{\alpha^2}} e^{-\frac{(b-b_0)^2}{\beta^2}}$$

is greater than the given threshold.

Such cell blocks are determined by the point $(a_0, b_0)$ and parameters $\alpha$, $\beta$. The region of such a cell block is denoted as $R(a_0, b_0, \alpha, \beta)$ below. When approximating the integration in Equations (4), (5) and (6), only the region $R(a_0, b_0, \alpha, \beta)$ is considered. In other words, the actual region of integration in Equations (4), (5) and (6) is the region $R(a_0, b_0, \alpha, \beta)$. In FIG. 51, the rectangle with dotted lines represents the cell-group, $R(a_0, b_0, \alpha, \beta)$.

Thus, Equations (4), (5) and (6) can be approximated by Equations (4-1), (5-1) and (6-1).

$$V = \int\int_{R(a_0,b_0,\alpha,\beta)} I(a,b) e^{-i\omega_x(a-a_0)} \quad \text{(Equation 4-1)}$$
$$e^{-i\omega_y(b-b_0)} e^{-\frac{(a-a_0)^2}{\alpha^2}} e^{-\frac{(b-b_0)^2}{\beta^2}} db\, da$$

$$\mathrm{Re}(V) = \int\int_{R(a_0,b_0,\alpha,\beta)} I(a,b) e^{-\frac{(a-a_0)^2}{\alpha^2}} \quad \text{(Equation 5-1)}$$
$$e^{-\frac{(b-b_0)^2}{\beta^2}} \cos(\omega_x(a-a_0)+\omega_y(b-b_0)) db\, da$$

$$\mathrm{Im}(V) = \int\int_{R(a_0,b_0,\alpha,\beta)} I(a,b) e^{-\frac{(a-a_0)^2}{\alpha^2}} \quad \text{(Equation 6-1)}$$
$$e^{-\frac{(b-b_0)^2}{\beta^2}} \sin(\omega_x(a-a_0)+\omega_y(b-b_0)) db\, da$$

When calculating Gabor Cosine transform or Gabor Sine transform, V in Equation (4-1) is evaluated on the region $R(a_0, b_0, \alpha, \beta)$. In the case of Gabor Cosine transform, the binary bit value of the frequency transform code is determined by the sign of $\mathrm{Re}(V)$ in Equation (5-1): it is 1 if $\mathrm{Re}(V) \geq 0$, and 0 otherwise. In the case of Gabor Sine transform, the binary bit value of the frequency transform code is determined by the sign of $\mathrm{Im}(V)$ in Equation (6-1) in the same way.

In this way, for N configurations of frequency transform methods and values of $a_0, b_0, \alpha, \beta, \omega_x, \omega_y$, N bit binary code is generated. Here, N denotes the length of the frequency transform code. Since multiple frequency transform values can be obtained from each cell-group using different frequency methods and their parameters, the length of the frequency transform code, N, may be different from the number of cell-groups.

Each binary value of the frequency transform codes can be obtained based on its own predetermined frequency transform method and parameters. In other words, different frequency methods or different parameters may be used for each binary value of the frequency transform code. In this way, the various features of a nose pattern image may be better encoded into the frequency transform code, and therefore increase the accuracy rate of recognition in comparison with the case where every binary value is calculated by using the same frequency method or parameters.

This strategy can also be applied to each breed type. Although the same frequency transform method or parameters may be chosen regardless of breed type, the accuracy rate of recognition may be increased if different frequency methods or parameters are properly chosen for each breed type.

For example, the best frequency transform method and parameters (e.g., frequencies) may be chosen when generating nose pattern codes based on the estimated size of nose pattern features in the given nose pattern image. Using this strategy, a fine distinction between breeds may be achieved where the sizes of nose pattern features are significantly different.

Below is a detailed account of the process of generating the masking code from the ROI in the masking code generation unit.

Each bit value of a masking code corresponds to a bit value of a frequency transform code. When a frequency code of N bits is generated from N configurations of frequency transform methods and values of $a_0, b_0, \alpha, \beta, \omega_x, \omega_y$, each bit value of a masking code is also computed from each of the N configurations. Thus, the length of masking codes is the same as the length of frequency transform codes.

The masking code generation process goes through a light-reflection masking step and an additional masking step. Depending on the methods of masking code generation, either steps or only one step may be applied.

(A) Light-Reflection Masking Step

When there are strong light reflections due to the wet nose or unexpected illumination problems, the nose pattern may appear damaged in the acquired nose image. Such regions are marked as damaged regions in the masking code.

More specifically, each value of the making code is assigned so that it can be distinguished from the value whether the corresponding frequency transform value is damaged or not due to the light reflections. For example, when the actual integration region $R(a_0, b_0, \alpha, \beta)$ includes damaged regions due to light reflections as in FIG. 50, the value of 0 is assigned to the corresponding masking bit value to mark the frequency transform value as a damaged one. Otherwise, the value of 1 is assigned to the corresponding masking bit value.

(B) Additional Masking Step

The region containing nose patterns in the nose images of subject animals can be damaged due to nose or facial hairs, long whiskers, or foreign substances attached to wet noses. When the region $R(a_0, b_0, \alpha, \beta)$ is damaged due to these reasons, the value of 0 is assigned to the corresponding masking bit value to mark the frequency transform value as a damaged one. Otherwise, the value of 1 is assigned to the corresponding masking bit value.

Once the nose pattern code consisting of the above-mentioned frequency transform code and masking code is generated, it is stored in the nose pattern code DB in the image recognition unit.

Below is a detailed account of the nose pattern code matching unit.

Figure 52:
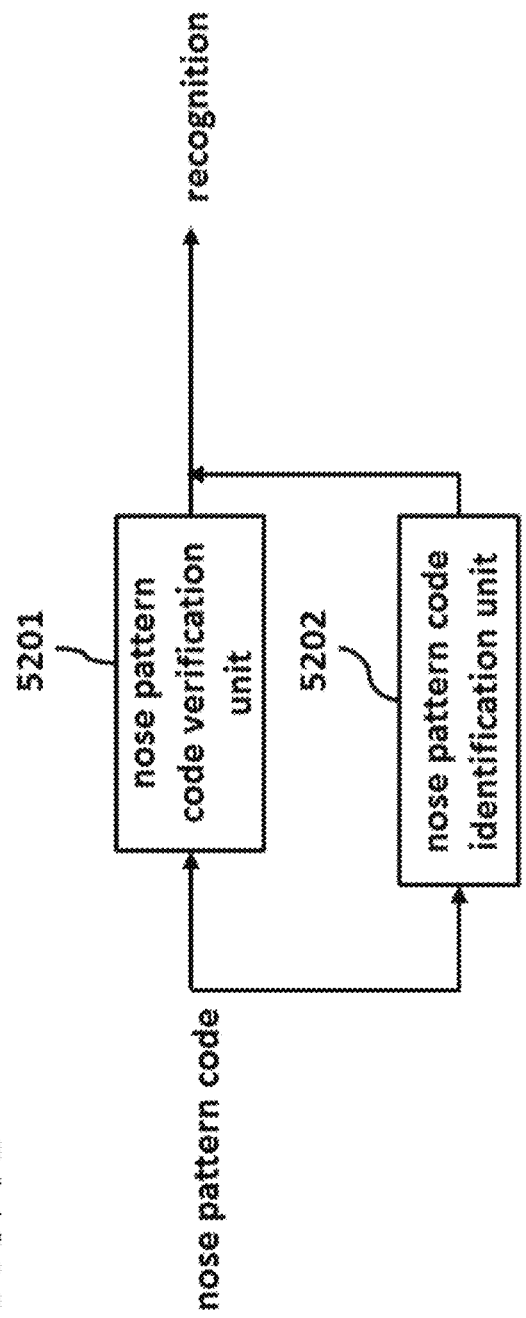
FIG. 52 is a simplified block diagram describing the nose pattern code matching unit.

FIG. 52 is a simplified block diagram describing the nose pattern code matching unit. As shown in FIG. 52, the nose pattern code matching unit may include the nose pattern code verification unit 5201 and the nose pattern code identification unit 5202.

The nose pattern code verification unit performs verification (one-to-one matching) by comparing the nose pattern code generated for verification and the nose pattern code stored in the nose pattern code DB in the image recognition unit. Verification of the generated nose pattern code is performed by computing the dissimilarity (the distance) of two nose pattern codes using one of following matching methods: a) simple matching, b) shift matching and c) block-wise shift matching.

(A) Simple Matching

Figure 53:
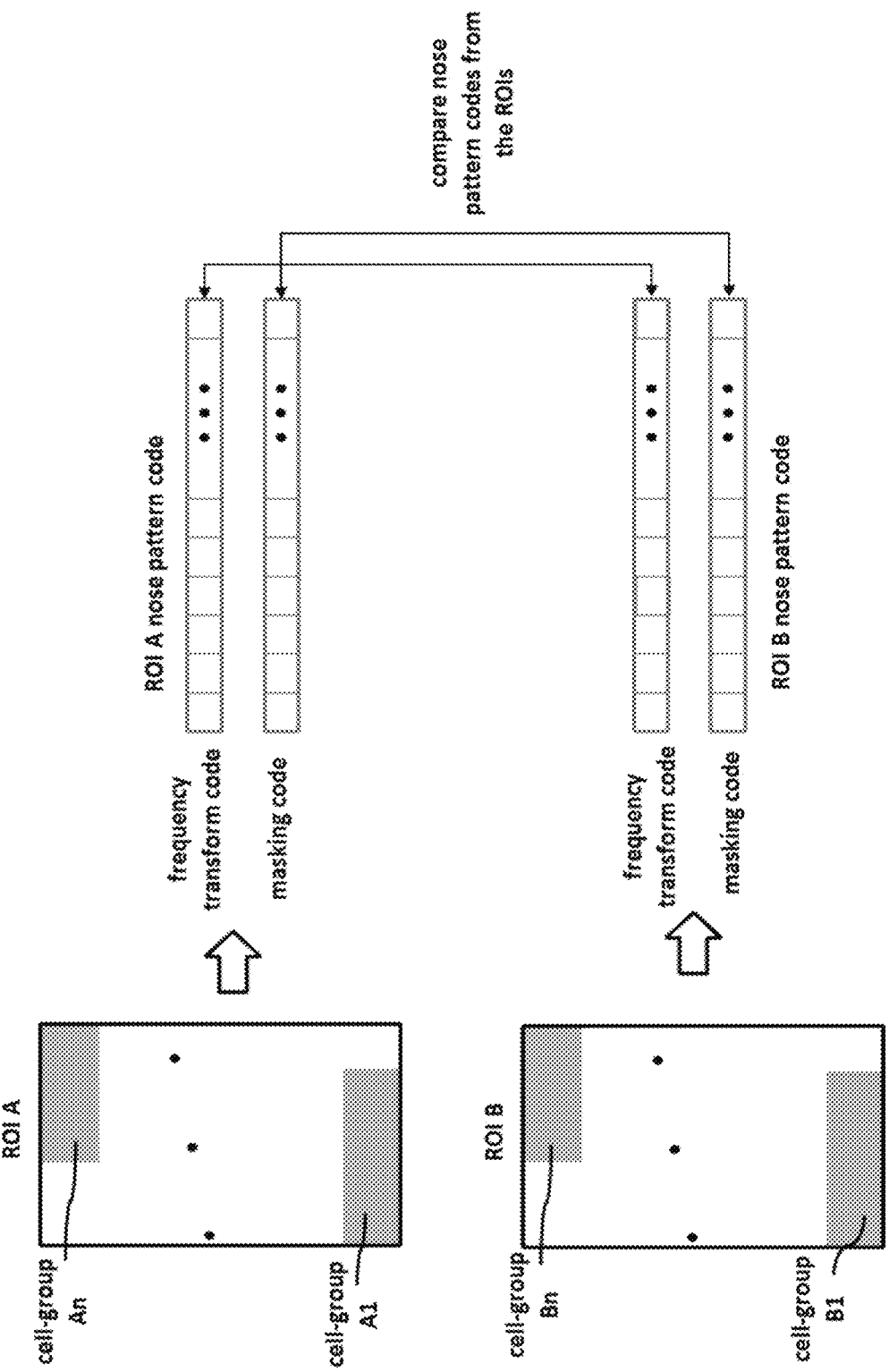
FIG. 53 is a diagram illustrating the method of nose pattern code identification through simple matching.

FIG. 53 is a diagram illustrating the method of nose pattern code verification through simple matching. As shown in FIG. 53, the whole ROI A is compared to the whole ROI B in the simple matching. When the distance between the two nose pattern codes corresponding to cell-groups from A1 to An of ROI A and cell-groups from B1 to Bn of ROI B is less than the given threshold, it is concluded that the two nose pattern images are taken from the same subject. Otherwise, it is concluded that the two images are taken from different subject animals.

Figure 54:
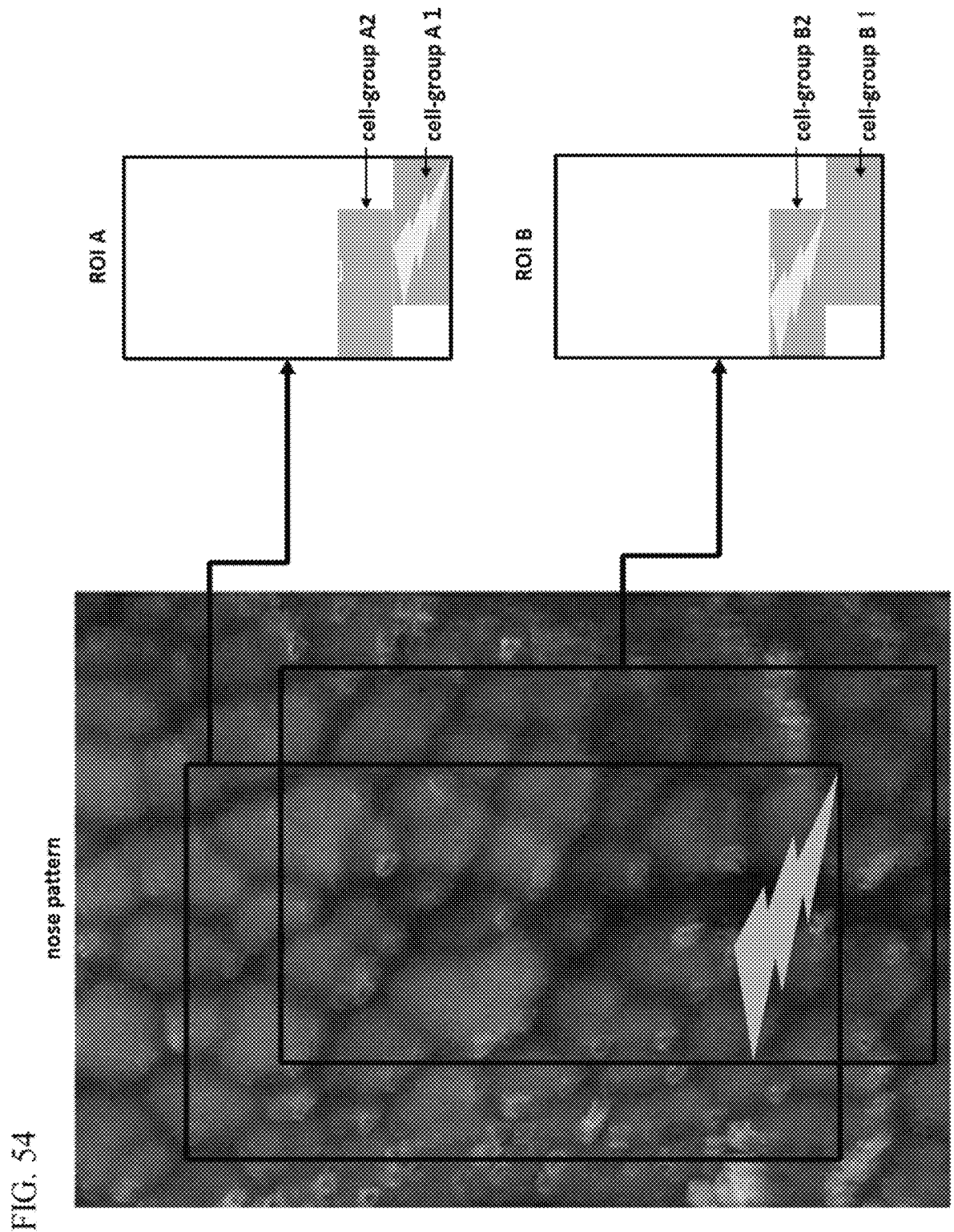
FIG. 54 is a diagram illustrating a situation in which different regions of interest have been selected from the same nose pattern image of the same individual for matching.

FIG. 54 is a diagram illustrating a situation in which different ROIs have been selected from the same nose pattern image of an individual for matching. As shown in FIG. 54, selecting the same ROI is critical in increasing the accuracy rate of recognition since the different ROIs from the same subject animal result in high distance, and thus in a false non-match in the simple matching. There is a high probability of error in simple matching if it is difficult to locate the same ROI from the nose pattern images.

(B) Shift Matching

As shown in FIG. 54, the probability of getting a false non-match is high when ROI A and ROI B are compared in simple matching even though they are from the same subject animal. More specifically, when cell-group A1 from ROI A and cell-group B1 from ROI B are compared in simple matching, it is concluded that they are taken from different individuals.

However, if cell-group A1 from ROI A and cell-group B2 from ROI B are compared, the distance between the two cell-groups will be very small since they contain the same nose pattern and thus the same frequency transform codes. Therefore, there is a low probability of error in matching if partial regions (local regions) of two ROIs are compared rather than the whole.

Figure 55:
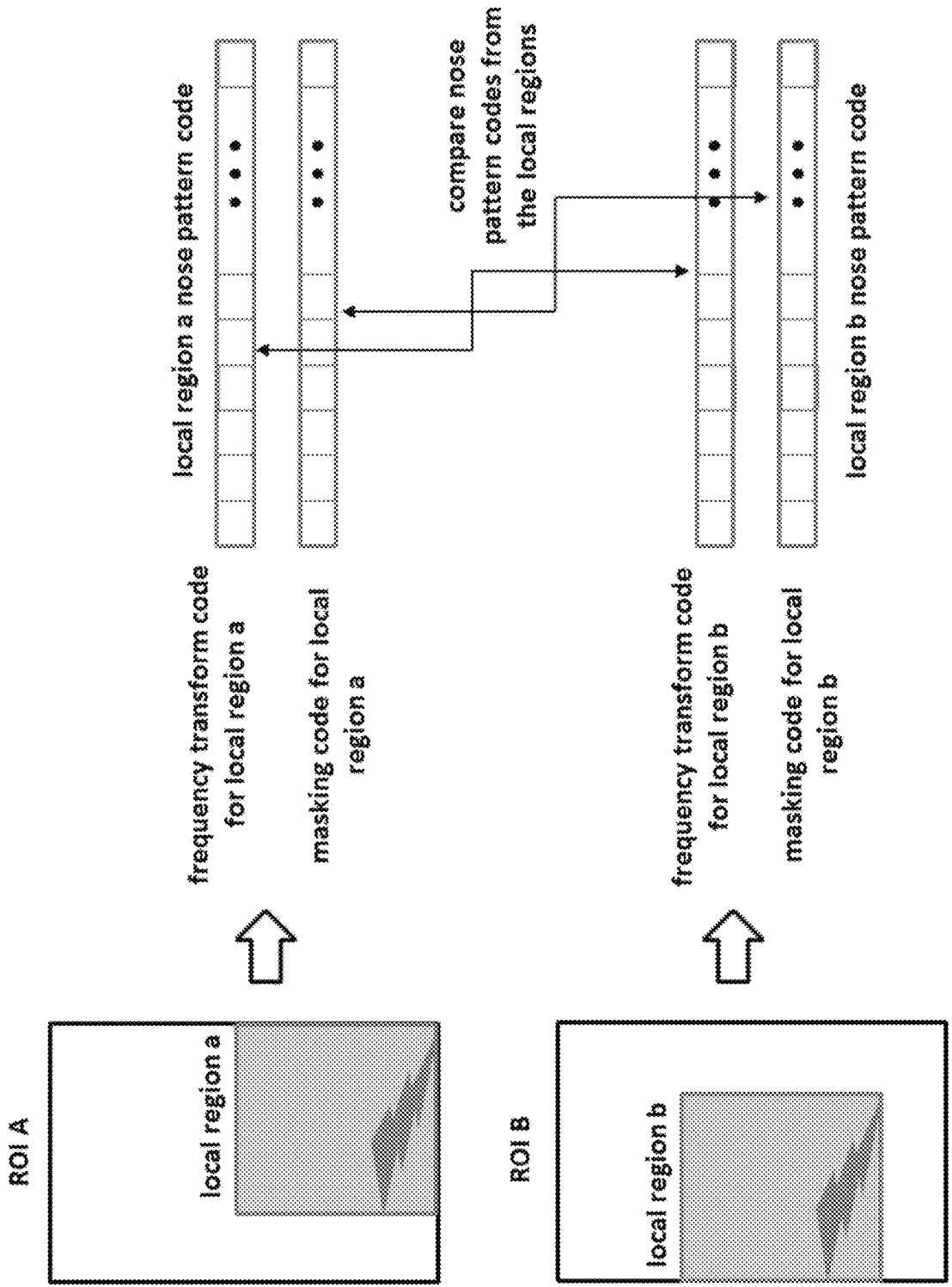
FIG. 55 is a diagram illustrating the method of nose pattern code identification through shift matching.

FIG. 55 is a diagram illustrating the method of nose pattern code identification through shift matching as one embodiment of the present invention. As shown in FIG. 55, the local region a in ROI A is compared to the local region b in ROI B. The nose pattern code generated from cell-groups through of the local region "a" is compared to the nose pattern code generated from cell-groups through of the local region "b".

In shift matching, the distance between two nose pattern codes is computed for each pair of local region "a" in ROI A and local region "b" in ROI B. By translating the local regions a and b in each ROI, multiple values of distance are computed. If the minimum of the multiple values of distance is less than the given threshold, it is concluded that the two nose pattern images are taken from the same individual. Otherwise, it is concluded that the two nose pattern images are taken from different subject animals.

For shift matching, nose pattern codes from all possible local regions in the ROI should be generated. In other words, the value of frequency transform should be computed for each cell-group in all possible local regions. Thus, it is required to compute all values of the frequency transform for all cell-groups in all possible local regions. For efficiency, the values of frequency transform from pre-computed cell-groups may be used rather than computing every value of frequency transform for every cell-group. When a cell-group is in a different local region, the pre-computed value from one local region is used for the other local region rather than re-computing the value of frequency transform for the cell-group. For this reason, local regions and cell-groups may be constructed with the efficiency of this computation in mind. In the case where this kind of computational efficiency is utilized, all values of frequency transform from all possible cell-groups are computed first and the nose pattern code for each local region is constructed using the pre-computed values of frequency transform.

Figure 56:
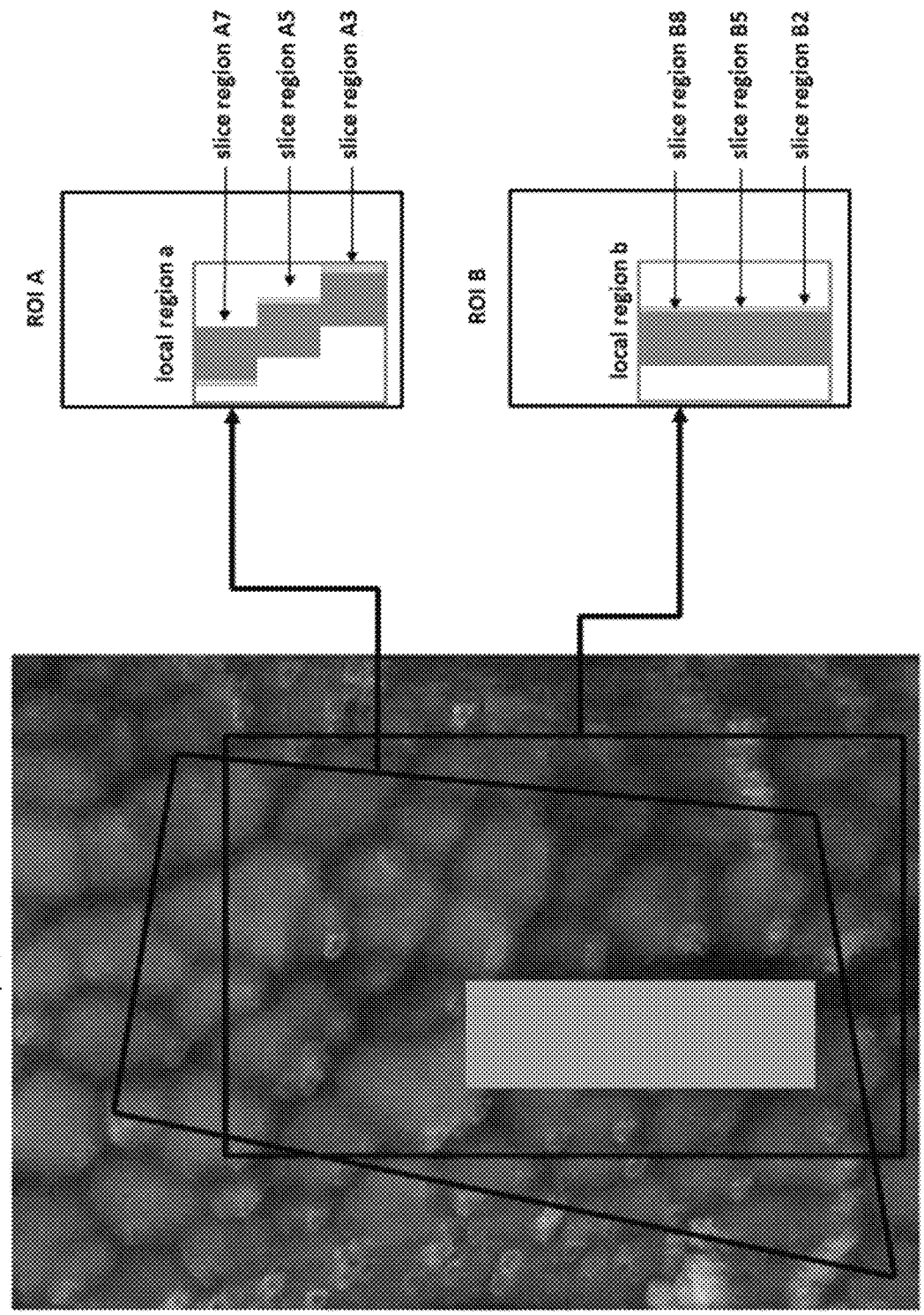
FIG. 56 is a diagram illustrating a matching situation in which the regions of interest of the nose pattern code selected from the same individual have nonidentical vertical and horizontal proportions.

FIG. 56 is a diagram illustrating a matching situation in which the ROIs of the nose pattern code selected from the same individual have nonidentical vertical and horizontal proportions. As shown in FIG. 56, it is critical to increasing the accuracy rate of recognition that the transformation from a quadrilateral ROI to a standard rectangular ROI should be incorporated in the shift matching since different shapes of ROI from the same subject animal result in different transformations, and in non-matching even though all of the translated local regions are compared. Therefore, the probability of error is high in the shift matching if any of the translated local regions of one ROI does not match any local region of the other ROI or different transformations are applied to make a standard rectangular ROI.

(C) Block-Wise Shift Matching

As shown in FIG. 56, if the local region a in ROI A is compared to the translated local region of b in ROI B, the probability of recognizing the same source animal is low. However, there is a low probability of error in identification if a partial region (called a slice region) of a local region is selected and compared by translating the slice region in a local region. For example, as in FIG. 56, if slice regions A3, A5, A7 in local region "a" have the same nose pattern as slice regions B2, B5, B8 in local region "b," respectively, the corresponding values of frequency transform from those slice regions are the same. Thus, by translating a slice region, it is probable that a match will be made between ROI A and ROI B.

Figure 57:
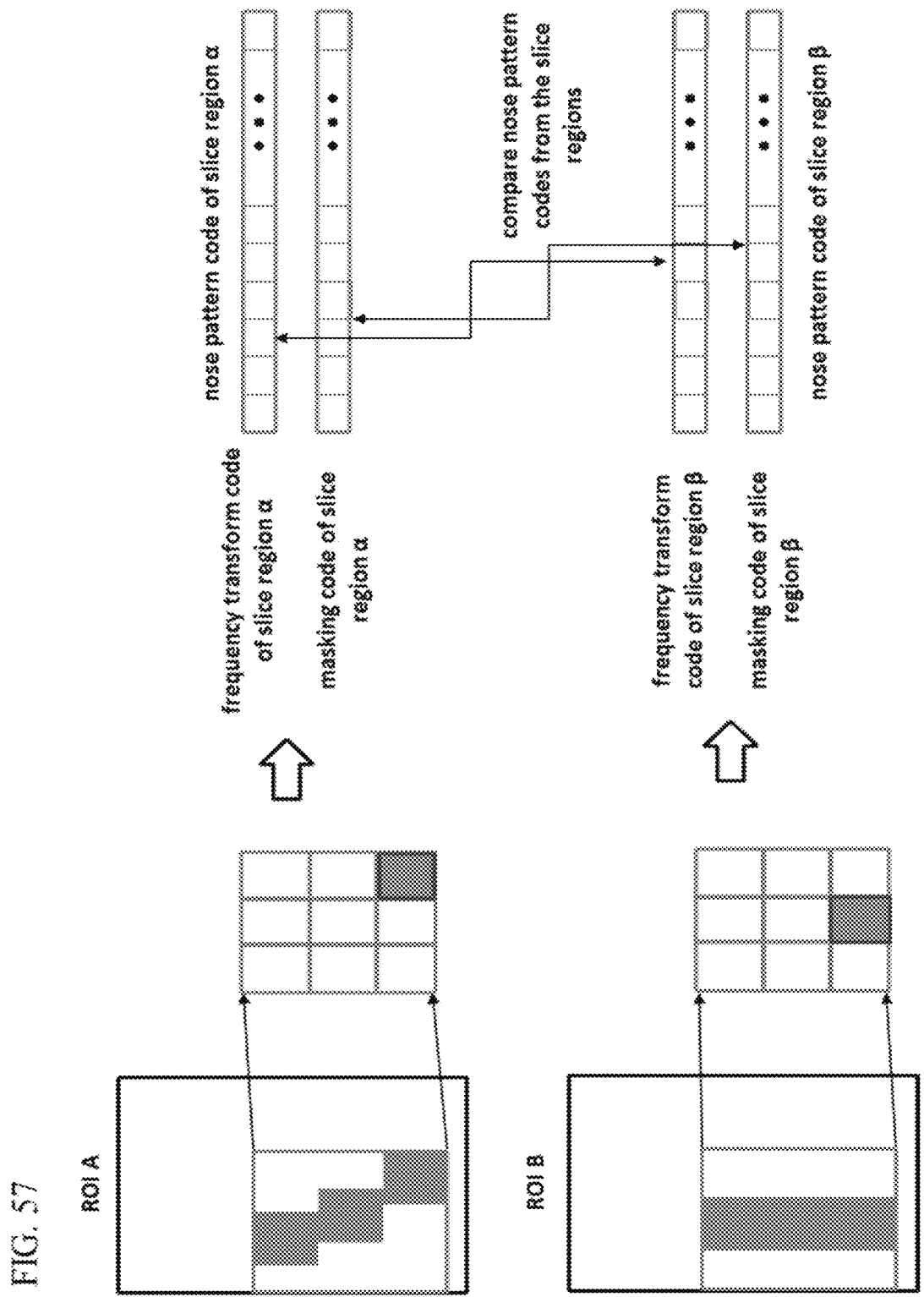
FIG. 57 is a diagram illustrating the method of nose pattern code identification through block-wise shift matching.

FIG. 57 is a diagram illustrating the method of nose pattern code identification through block-wise shift matching as one embodiment of the present invention. As shown in FIG. 57, slice region α of local region "a" in ROI A is compared to slice region β of local region "b" in ROI B. Local region "a" in ROI A and local region "b" in ROI B are subdivided into n*m equal sized pieces with n horizontal pieces and m vertical pieces. Then the distance between the nose pattern code corresponding to each piece of local region "a" and local region "b" is computed.

In block-wise shift matching, slice regions a and 13 are translated in a given range so that multiple values of distance are computed. Thus, while only one distance is computed for each pair of local regions in shift matching, in block-wise shift matching the distance is computed for each pair of slice regions and thus multiple values of distance for each pair of local regions. So, one representative value of distance (called "final distance") from multiple values of distance needs to be computed to compare with the given threshold.

To compute the final distance for each pair of local regions in block-wise shift matching, the distance should be computed for each pair of slice regions. The distance (called block distance) between a pair of slice regions is the minimum value of all possible distances computed from all possible translations of slice regions. Then, the final distance may be defined as one of the minimum, a geometric average, an arithmetic average of all block distances. When this final distance is less than the given threshold, two animal subjects are regarded as the same individual. Otherwise, the two animal subjects are regarded as different individuals.

In these verification methods (simple matching, shift matching, and block-wise shift matching), the above ROI A can be the ROI from which a stored nose pattern code is generated, and the ROI B can be the one from which the nose pattern code for verification is generated, and vice versa.

Below is a detailed account of matching methods for Gabor Sine transform.

Example

Gabor Sine Transform (A) Simple Matching

For a ROI, let C denote a frequency transform code from the ROI and M a masking code from the ROI generated by Gabor Sine transform. Then, the nose pattern code for ROI A consists of N bits of frequency transform code C1 and N bits of masking code M1, and the nose pattern code for ROI B consists of N bits of frequency transform code C2 and N bits of masking code M2.

The distance (D) between two nose pattern codes can be computed by Equation (7).

$$D = \frac{|(C_1 \text{ XOR } C_2) \text{ AND } (M_1 \text{ AND } M_2)|}{|M_1 \text{ AND } M_2|}] \quad \text{(Equation 7)}$$

In Equation (7), XOR denotes the operator of bitwise Exclusive-OR, AND the operator of bitwise AND. The number of bits whose value is 1 in the array of bits A is denoted by |A|.

When the above computed distance is less than the given threshold, it is concluded that the two animal subjects represented by those two nose pattern codes are identical, and they are different individuals otherwise.

(B) Shift Matching

For a local region in a ROI, let C denote a frequency transform code from the local region and M a masking code from the local region generated by Gabor Sine transform. Then, the nose pattern code for local region "a" in ROI A consists of N bits of frequency transform code C1 and N bits of masking code M1, and the nose pattern code for local region "b" in ROI B consists of N bits of frequency transform code C2 and N bits of masking code M2.

Figure 58:
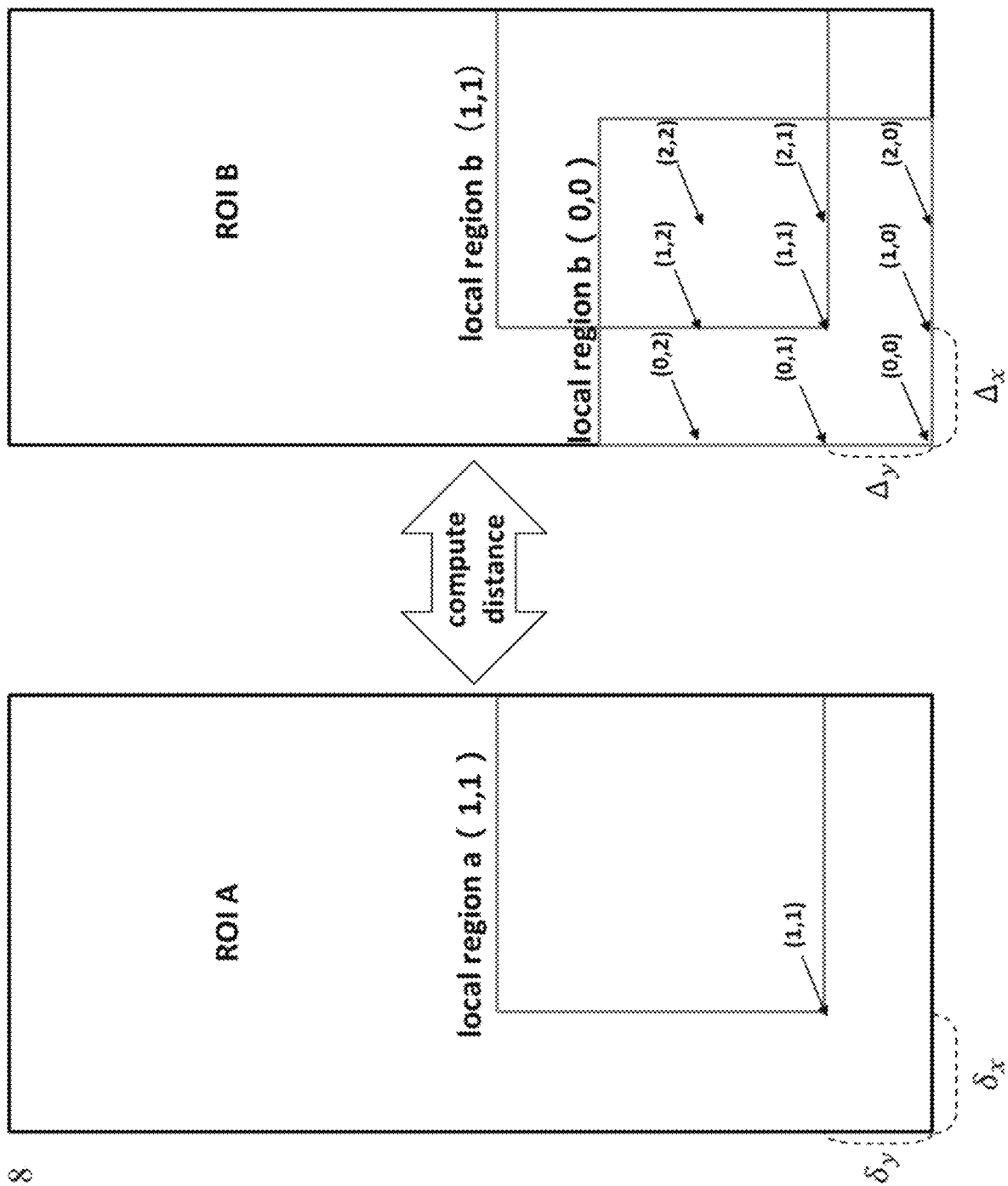
FIG. 58 is a diagram illustrating the process of nose pattern code identification through shift matching using Gabor sine transform.

FIG. 58 is a diagram illustrating the process of nose pattern code identification through shift matching using Gabor Sine transform. Let R1 be the set of all the points $(\delta_x, \delta_y)$ of the lower left vertices of all the possible translated local regions in ROI A, and R2 the set of all the points $(\Delta_x, \Delta_y)$ of the lower left vertices of all the possible translated local regions in ROI B. FIG. 58 is a diagram illustrating the case where R1={(1,1)}, R2={(0,0),(1,0),(2,0),(0,1),(1,1),(2,1),(0,2),(1,2),(2,2)}.

Then, one nose pattern code (a(1,1)) from ROI A, and nine nose pattern codes (b(0,0), b(1,0), b(2,0), b(0,1), b(1,1), b(2,1),b(0,2), b(1,2), b(2,2)) from ROI B are generated, and these codes give a total of nine values of distance by one-by-one comparison. Thus, in this case, it is only necessary to see if the minimum of nine values of distance is less than the given threshold.

In this way, when the nose pattern code for a local region "a" in ROI A is denoted by C1($\delta_x$, $\delta_y$), M1($\delta_x$, $\delta_y$) and that for a local region "b" in ROI B denoted by C2 ($\Delta_x$, $\Delta_y$), M2($\Delta_x$, $\Delta_y$) the distance between the two ROIs can be computed by Equation (8).

$$D = \min_{(\delta_x, \delta_y) \in R_1, (\Delta_x, \Delta_y) \in R_2} \frac{|(C1 \text{ XOR } C2) \text{ AND } (M1 \text{ AND } M2)|}{|M1 \text{ AND } M2|} \quad \text{(Equation 8)}$$

In Equation (8), XOR denotes the operator of bitwise Exclusive-OR, AND the operator of bitwise AND. The number of bits whose value is 1 in the array of bits A is denoted by |A|.

(C) Block-Wise Shift Matching

For a slice region of a local region in a ROI, let C denote a frequency transform code from the slice region and M a masking code from the slice region generated by Gabor Sine transform. Then, the nose pattern code for slice region α of local region "a" in ROI A consists of N bits of frequency transform code C1 and N bits of masking code M1, and the nose pattern code for slice region β of local region "b" in ROI B consists of N bits of frequency transform code C2 and N bits of masking code M2.

Figure 59:
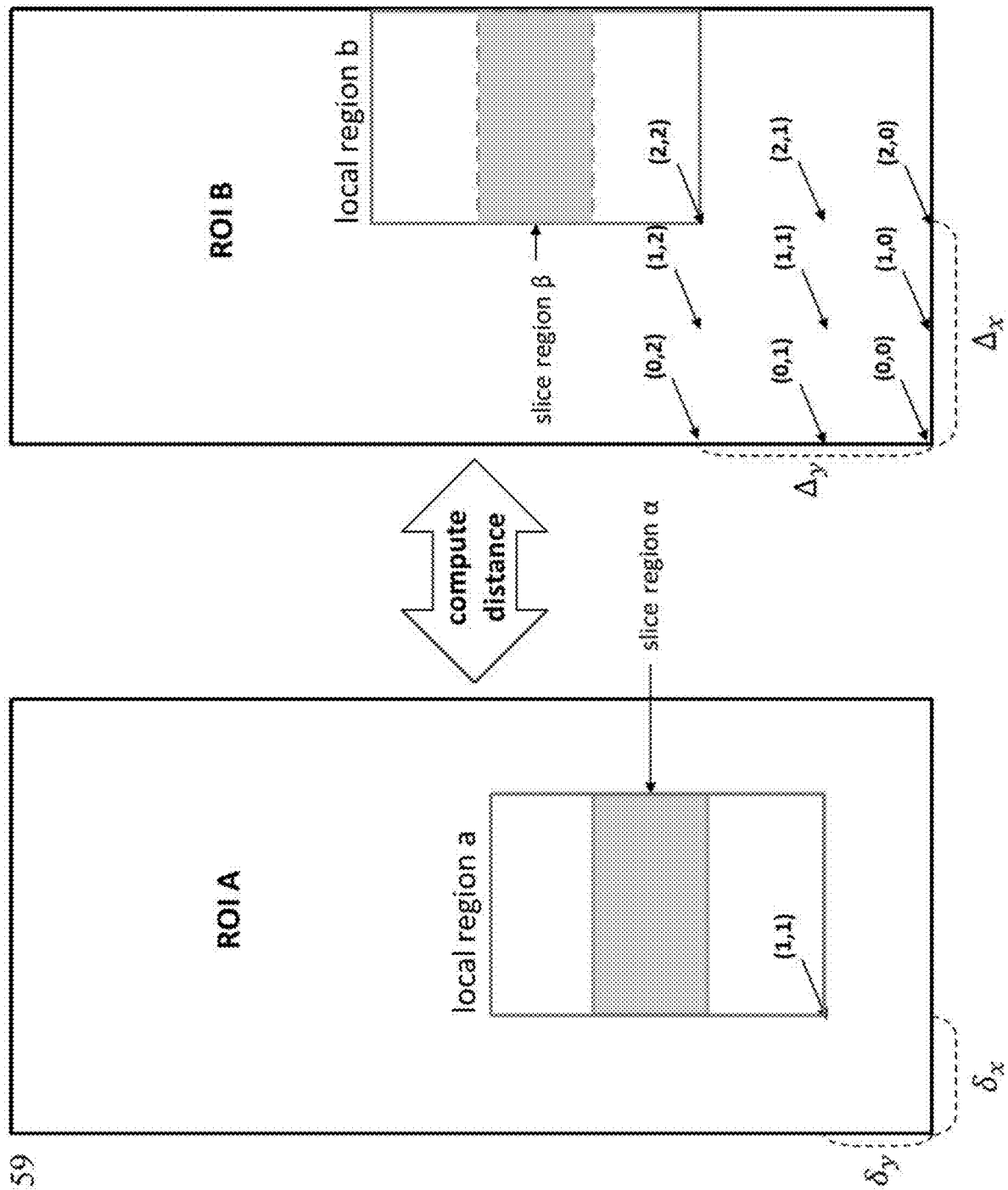
FIG. 59 is a diagram illustrating the process of nose pattern code identification through block-wise shift matching using Gabor sine transform.

FIG. 59 is a diagram illustrating the process of nose pattern code identification through block-wise shift matching using Gabor Sine transform.

Let R1 be the set of all the points $(\delta_x, \delta_y)$ of the lower left vertices of all the possible translated regions from slice region α in ROI A, and R2 the set of all the points $(\Delta_x, \Delta_y)$ of the lower left vertices of all the possible translated regions from slice region β in ROI B. FIG. 58 is a diagram illustrating the case where R1={(1,1)}, R2={(0,0),(1,0),(2,0),(0,1),(1,1),(2,1),(0,2),(1,2),(2,2)}.

Then, one nose pattern code (α(1,1)) from slice region α in ROI A, and nine nose pattern codes (β(0,0), β(1,0), β(2,0), β(0,1), β(1,1), β(2,1), β(0,2), β(1,2), β(2,2)) from slice region β in ROI B are generated, and these codes give a total of nine values of distance by one-by-one comparison. The minimum of all these values of distance is called the distance between slice regions, and the final distance between two ROIs may be defined as one of the arithmetic average, the geometric average, and the minimum of all possible distances between two corresponding slice regions.

In this way, when the nose pattern code for the translated region of the k-th slice region α in ROI A is denoted by C1 (k, $\delta_x$, $\delta_y$), M1(k, $\delta_x$, $\delta_y$) and that for the translated region of the k-th slice region β in ROI B is denoted by C2(k, $\Delta_x$, $\Delta_y$), M2(k, $\Delta_x$, $\Delta_y$), the distance between two corresponding k-th slice regions can be computed by Equation (9).

$$D(k) = \min_{(\delta_x, \delta_y) \in R_1, (\Delta_x, \Delta_y) \in R_2} \frac{|(C_1 \text{ XOR } C_2) \text{ AND } (M_1 \text{ AND } M_2)|}{|M_1 \text{ AND } M_2|} \quad \text{(Equation 9)}$$

In Equation (9), XOR denotes the operator of bitwise Exclusive-OR, AND the operator of bitwise AND. The number of bits whose value is 1 in the array of bits A is denoted by |A|.

The final distance between two ROIs may be defined as one of the geometric average, the arithmetic average, and the minimum of all values of distance between two corresponding slice regions for all pairs of slice regions. When the above computed final distance is less than the given threshold, it is concluded that the two animal subjects represented by those nose pattern codes are identical, and they are different individuals otherwise.

In these verification methods (simple matching, shift matching, and block-wise shift matching), the above ROI A can be the ROI from which a stored nose pattern code is generated, and the ROI B can be the one from which the nose pattern code for verification is generated, and vice versa.

Below is a detailed account of the above nose pattern code identification unit.

The nose pattern code identification unit performs identification (one-to-many matching) by comparing the nose pattern code generated for identification with multiple nose pattern codes stored in the nose pattern code DB in the image recognition unit.

While verification (one-to-one matching) requires computing the distance between a single nose pattern code and a single stored nose pattern code through simple matching, shift matching or block-wise shift matching, identification (one-to-many matching) requires computing the distances between a single nose pattern code and each of the multiple nose pattern codes stored in the DB.

Figure 60:
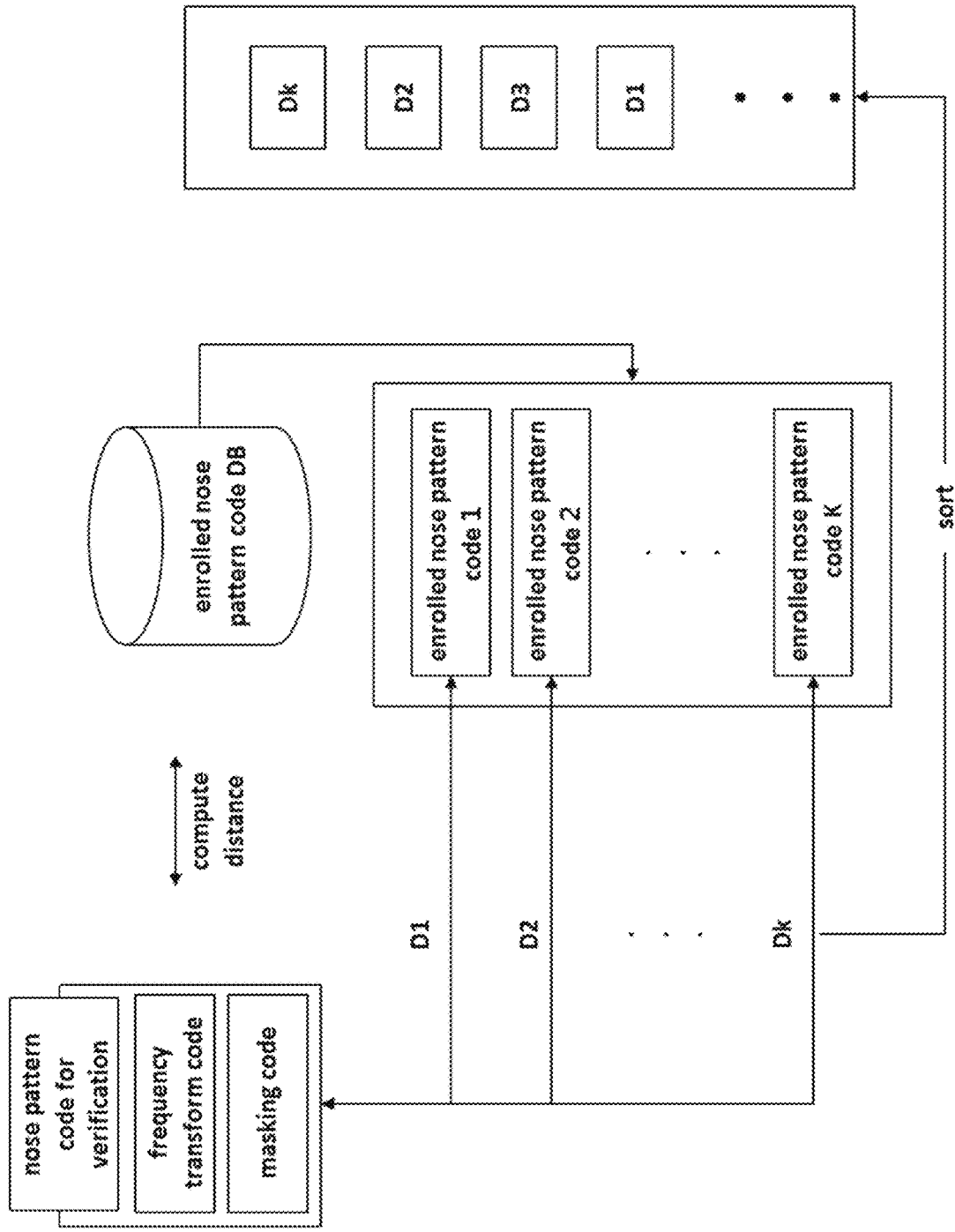
FIG. 60 is a diagram illustrating the method of nose pattern code identification (one-to-many matching).

FIG. 60 is a diagram illustrating the method of nose pattern code identification (one-to-many matching) as one embodiment of the present invention. As shown in FIG. 60, identification is performed by computing the distances between a single nose pattern code given for identification and each of k nose pattern codes (nose pattern code_1, . . . , nose pattern code_k) stored in the DB. As previously described, each nose pattern code stored in the DB consists of the frequency transform code C and the masking code M, and the DB of pre-registered nose pattern codes may be constructed as a part of the image recognition unit.

From k nose pattern codes stored in the DB and a single nose pattern code given for identification, a total of k distances are computed, and these k distances may be denoted by D1, . . . , Dk. The values of D1, . . . , Dk may be sorted in a descending or ascending order. One or more candidate nose pattern codes can be selected, according to one of three predefined selection rules: (a) a rule selecting the nose pattern code that gives the minimum distance among all those that yield distances less than the given threshold, (b) a rule selecting all the nose pattern codes whose distance is less than the given threshold, and (c) a rule selecting a predefined number, say n, of nose pattern codes whose distance is within top n least distances.

For example, as shown in FIG. 60, when the distances D1, D2, . . . , Dk are sorted in such a way that D3<D1<Dk<D2< . . . and the values of D3, D1, Dk, D2 are all the values less than the given threshold, the group of selected nose pattern codes consists of only one nose pattern code whose distance is D3 by rule (a); all of D3, D1, Dk, D2 by rule (b); or D3, D1 and Dk by rule (c) with n=3.

The image recognition unit according to an embodiment of the present invention as described above may be implemented as a program and recorded on a medium readable by a computer, which includes all kinds of compatible data storing devices such as ROM, RAM, CD ROM, magnetic tapes, floppy disks, and optical data storage devices, and carrier wave (e.g., transmission through the Internet).

The recording medium may also be distributed over network coupled computer systems so that the computer readable code can be stored and executed in a distributed manner. In addition, the functional programs, codes, and code segments for implementing the present invention may be easily construed by programmers skilled in the area relevant to the invention.

The following looks at the technical configuration of the aforementioned animal recognition method involving the characteristics of the subject animal.

The flowchart in FIG. 11 summarizes the method of animal recognition in the present invention, starting with S1101 selecting and S1102 fitting the animal into the appropriate body stabilizer unit; S1103 fixing the nose of the subject onto the image acquisition unit and S1104 acquiring the nose pattern image; S1105 at the image recognition unit, generating a nose pattern code using the raw or processed nose pattern image and S1106 enrolling and identifying the individual using the nose pattern code.

Further technical details have been omitted to avoid redundancy.

Figure 21:
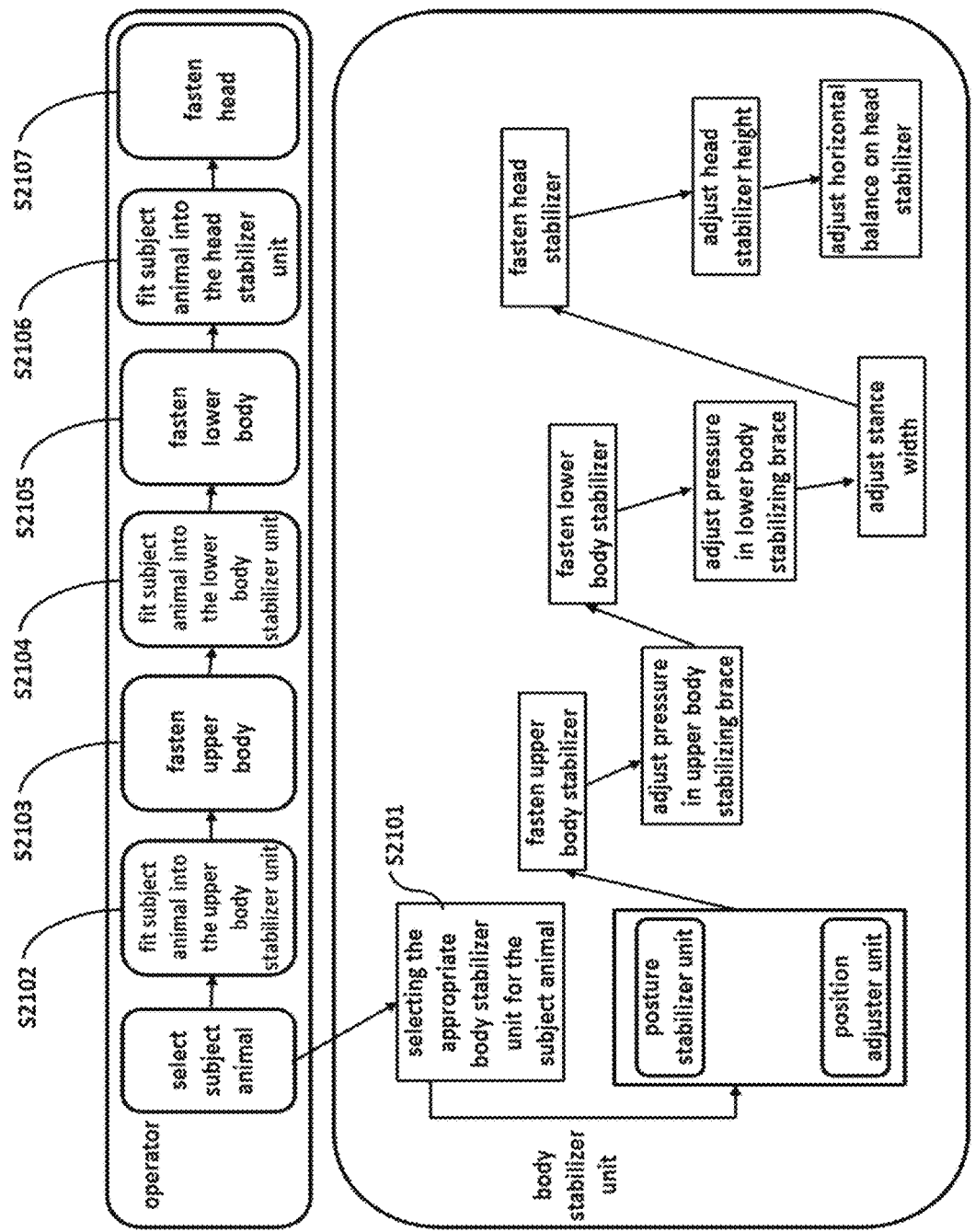
FIG. 21 is a flowchart illustrating a method of operating the body stabilizer unit in the present invention.

The sequence of operation for the body stabilizer unit as shown in FIG. 21 is as follows: S2101 select the appropriate body stabilizer unit for the subject animal by taking into consideration the overall size, leg length, feet size, head size, and the relative location of the nose; S2102 fit the subject animal into the upper body stabilizer unit; S2103 fasten the upper body by utilizing the upper body stabilizing brace subunit and upper body stabilizing brace pressure adjuster subunit to fit the shoulder width; S2104 fit the subject animal into the lower body stabilizer; S2105 fasten the lower body by utilizing the lower body stabilizing brace subunit and lower body stabilizing brace pressure adjuster subunit to fit the ankles or legs; S2106 set the stance width adjuster, and also the height adjuster to fit the subject's height if necessary to connect the upper and lower body stabilizer units; S2107 fasten the head by utilizing the head stabilizer unit, making sure to set the height adjuster unit to the correct height and the horizontal balance adjuster unit to have the nose facing the image acquisition unit head-on.

Further technical details have been omitted to avoid redundancy.

An example of the image acquisition process is illustrated in FIG. 38; the order of events need not be limited as follows. S3801 the operator selects the species on the display unit to start the automatic mode, or chooses the manual mode; S3802 in automatic mode, once the species selection is made, pressing the capture button starts the acquisition of the batch of nose pattern images at n frames per second while the lens module is shifted about within the preset range of positions (adjusting values of a and b). In the automatic mode, the image capture unit, illumination unit and front unit are automatically adjusted to accommodate the subject animal based on the values stored in the parameter DB for FOV, focus, luminosity, etc. However, in manual mode, the operator visually evaluates the features and variables of the nose pattern images through the display unit, and selects the best image. S3803 The nose pattern images acquired from the sensor of the image capture unit are stored in the buffer, upon which the main processor unit calculates the individual scores and compares to the threshold values in the reference DB. S3804 Once the best image that passes all the thresholds is selected, it is stored in the buffer.

Further technical details have been omitted to avoid redundancy.

FIG. 40 illustrates the method by which an animal nose pattern image is analyzed to be used for identification, the order of which may be modified to better suit the equipment or circumstances: S4001 acquisition of the subject animal's nose pattern image by utilizing the body stabilizer unit and image acquisition unit; S4003 setting the ROI on the (processed) nose pattern image; S4005 generating a nose pattern code from the fixed ROI; S4006 enrolling the generated nose pattern code; S4007 comparing the stored nose pattern code from the enrollment to the newly generated nose pattern code in one-to-one matching for verification; and S4008 running one-to-many matching for identification. Images acquired from S4001 that have been processed are called processed nose pattern images, and an additional step S4002 for storing them may be included. Also, the step S4004 that generates a standardized ROI from the ROI selected in S4003 may also need to occur.

Further technical details have been omitted to avoid redundancy.

The following steps describe the process of selecting usable nose pattern images. The main processor unit selects nose pattern images that are of sufficient quality to be used in the image recognition unit, out of all the images captured by the image capture unit. When multiple nose pattern images are obtained by the image capture unit, each image is given individual scores on specific variables, and images that pass the threshold set by the image analysis unit are selected. If none out of a particular batch meet the threshold, then that whole group is discarded and a request for a new batch is sent to the image capture unit. During this selection process, the images are evaluated on such criteria as, the amount of light reflection, sharpness, contrast ratio, ROI for capture, noise level, etc; and only those images that pass the threshold for each variable are accepted. When more than one image out of a single batch pass the threshold the one with the highest total score (sum of individual scores) is selected, and this process may take place simultaneously as the image acquisition in the image analysis unit or the image recognition unit.

There are two types of variables: those that are not related to species-specific characteristics (A1-A3) and those that are (A4-A12). The former includes sharpness A1, contrast A2, and noise level A3; the latter includes ROI for capture A4, presence of light reflection A5, nostril location A6, sharpness of nostril image A7, contrast level of nostril image A8, noise level of nostril image A9, sharpness of the border between the nostril and ROI A10, contrast level at the border between the nostril and ROI A11, and noise level at the border between the nostril and ROI A12. Variables may be appropriately added to or subtracted from the above list depending on a subject animal species' particular characteristics.

When selecting nose pattern images, each image in a batch is given individual scores on specific variables, and images that pass the threshold set by the image analysis unit are selected. When more than one image out of a single batch pass the threshold the one with the highest total score (sum of individual scores) is selected.

Further technical details have been omitted to avoid redundancy.

Below is a detailed account of the methods of processing raw nose pattern images into processed nose pattern images.

Freshly acquired nose pattern images may require processing in order to increase the identification rate. Raw acquired images may present different levels of noise and blurring, and may require contrast adjustments to normalize the distribution of pixel values.

The present invention uses the histogram equalization technique to normalize the distribution of pixel values of images. In order to adjust the distribution of pixel values, a distribution function is fixed and applied with histogram equalization for each nose pattern image to have the same fixed distribution function.

Image filtering techniques may also be applied to take care of the noise and blurring issues, with Gaussian or median filters for noise level adjustment, and a variety of low-pass filters in the frequency domain. Moreover, sharpening techniques using derivatives can be used to accentuate the embossed nose patterns, and de-convolution techniques can be used to restore damaged images.

Below is a detailed account of the method of fixing the ROI from the (processed) nose pattern image.

In the first step, the nostril boundary needs to be found in order to fix the ROI from the nose pattern image.

FIG. 42 is a schematic diagram illustrating how to find the nostril boundary as one embodiment of the present invention. FIG. 42 illustrates the nostril boundary setting process, where the nostrils appear as a shade due to the indirect illumination. The boundary of this shade is the basis for the nostril boundary, which may take the form of a circular or elliptical arc, etc. In order to extract the boundary points, starting with a point(s) within the shade as the center point(s), the boundary points are located based on the change in brightness along the ray from the fixed center points. Points along the rays extending in various directions that display a sharp change in brightness are marked as candidate points, and the correct boundary points are found among those candidate points based on the statistical analysis of nostril shape and location.

Using the above statistical analysis, not all of the boundary points of the nostril in various directions may be extracted resulting in that only parts of boundary points are extracted.

Sometimes, even with indirect illumination certain areas that are not in the nostrils may appear to be inside of a similar shade, and therefore it is helpful to use multiple center points and statistical analysis utilizing the shape and location information of nostrils to prevent finding incorrect boundary points.

The nostril boundaries are approximated by curves fitting the boundary points found in the above step. In this approximation, the final approximation curve is the best curve fitting the boundary points found by various regression analyses, and it is usually a circular arc or elliptical arc.

Although the left and right nostril boundaries can be regarded as symmetric curves when they are seen from the front of the nose, the two approximation curves can be asymmetric ellipses if the nose pattern image is taken from askew.

Also, since the curve approximation unit separately approximates the left and right nostril boundaries, the two approximation curves can have different shapes resulting in that one curve is a circle, and the other an ellipse. It is also possible that the two approximation curves are different in size although they are all either circle or ellipses.

A quadrilateral region of a nose pattern image between the two approximation curves obtained from the above step is to be defined. This process consists of two steps: a) the region between two approximation curves is identified and b) a quadrilateral region contained in the identified region is extracted.

(A) the First Step where the Region Between Two Approximation Curves is Identified:

FIG. 44 is a schematic diagram illustrating how to identify the region between the two approximation curves (circles or ellipses) as one embodiment of the present invention. As shown in FIG. 44, two points which are on the intersections between each approximation curve and the line segment connecting two centers of the approximation curves are located, and the two tangent lines which tangent at each located point to the approximation curve (the left tangent line is denoted by T_L, and the right tangent line by T_R) are found. These tangent lines may be perpendicular to the line segment connecting the two centers when the two approximation curves are symmetrical, and may not be perpendicular when they are not symmetrical.

The two connecting lines are then found: one line connecting two upper vertex points of the approximation curves and the other line connecting two lower vertex points (the upper line is denoted by T_U, and the lower line denoted by T_D). In this step, the two connecting lines are tangent lines which tangent to the both of the approximation curves when they are both circles and the two lines connects two upper vertex points or two lower vertex points when they are both ellipses.

(B) The Second Step where the Quadrilateral Region Between Two Approximation Curves is Extracted as the ROI.

FIG. 45 is a schematic diagram illustrating how to extract the quadrilateral region between the two approximation curves as one embodiment of the present invention. As shown in FIG. 45, the ROI is the quadrilateral region encompassed by four lines obtained in Step A. The shape and the size of the ROI may be varied depending on the relative position of the nose to the position of the image acquisition unit when the nose image is captured, and thus even the ROI from the same animal subject may be varied.

In the approximation curve unit, the two approximation curves may be obtained so that the line segment connecting two center points of the approximation curves passes each of vertex points of two approximation curves when they are both approximated by ellipses.

By assuming that two nostril boundary curves are symmetric when they are captured directly from the front, the line segment connecting the two center points of the two elliptical nostril boundary curves should pass the vertex point of each ellipse. Using this fact, the boundary curves can be approximated by ellipses so that the line segment connecting two center points of ellipses passes the vertex points of ellipses.

Further technical details have been omitted to avoid redundancy.

Below is a detailed account of the step to generate the standardized ROI from the above ROI.

The ROI is transformed into the standardized ROI when it is necessary to normalize the above ROI obtained from the step of ROI fixing. FIG. 46 is a diagram illustrating how the ROI from the same nose pattern image may be varied depending on the approximation curves of the nostril boundaries. As shown in FIG. 46, the quadrilateral ROI from even the same nose pattern image may be varied when different approximation curves are used, and the above quadrilateral ROI from even the same subject animal may also be varied depending on the relative position of the nose to the image acquisition unit during capture.

To increase the identification rate, it is necessary to transform the given ROI into the standardized shape independent of the relative position of the nose and the approximation curve shapes. The standardized ROI fixing unit takes care of the transformation process of the ROI into the standard rectangular shape based on Equation (2).

By the above transformation various shapes of quadrilateral ROIs can be transformed into a rectangular shape, which is the standard ROI and thusly stored in the memory or the DB. The technical details of the standard ROI have been omitted to avoid redundancy.

Below is a detailed account of the process of generating nose pattern codes from the above-stated ROI.

Nose pattern codes are generated via steps of generating the a) frequency transform code and b) masking code from the ROI.

Below is a detailed account of the process of generating frequency transform codes from the ROI stated above.

FIG. 49 is a block diagram illustrating the process of generating nose pattern codes from the ROI. As shown in FIG. 49, a nose pattern code consists of the frequency transform code and the masking code generated from the whole ROI. The nose pattern code is a 2-bit array and its component value is determined by predetermined frequency transform methods and parameters of the transforms.

The predetermined frequency transform methods may include several frequency methods including Gabor transform, Haar transform, Gabor Cosine transform, Gabor Sine transform, Sine transform, Cosine transform, and various wavelet transforms.

In the present invention, different frequencies for real and imaginary parts of Gabor transform may be used. Also, either of the real part of Gabor transform (Gabor Cosine transform) or the imaginary part of Gabor transform (Gabor Sine transform) may be used alone. The choice of frequency transform methods may be determined based on the performance and the processing speed of the image recognition unit. The technical details regarding the generation of frequency transform codes have been omitted to avoid redundancy.

Below is a detailed account of the process of generating masking codes from the ROI stated above.

Each bit value of a masking code corresponds to a bit value of a frequency transform code. When a frequency code of N bits is generated from N configurations of frequency transform methods and values of $a_0$, $b_0$, $\alpha$, $\beta$, $\omega_x$, $\omega_y$, each bit value of a masking code is also computed from each of the N configurations. Thus, the length of making codes is the same as the length of frequency transform codes.

The masking code generation process goes through a light-reflection masking step and an additional masking step. Depending on the methods of masking code generation, either steps or only one step may be applied. The technical details regarding the generation of masking codes have been omitted to avoid redundancy.

Below is a detailed account of the process of verification (one-to-one matching), in which a nose pattern code generated for verification is compared to a nose pattern code stored in the nose pattern code DB.

The nose pattern code verification unit performs verification (one-to-one matching) by comparing the nose pattern code generated for verification and the stored nose pattern code. Verification of the generated nose pattern code is performed by computing the distance between two nose pattern codes through one of the following matching methods: a) simple matching, b) shift matching and c) block-wise shift matching. The technical details regarding the matching methods have been omitted to avoid redundancy.

Below is a detailed account of the process of identification (one-to-many matching), in which the distances between the nose pattern code generated for identification and each of the multiple nose pattern codes stored in the nose pattern code DB is computed.

While verification (one-to-one matching) requires computing the distance between a single nose pattern code and a single stored nose pattern code through simple matching, shift matching or block-wise shift matching, identification (one-to-many matching) requires computing the distances between a single nose pattern code and each of the multiple nose pattern codes stored in the DB.

FIG. 60 is a diagram illustrating the method of nose pattern code identification (one-to-many matching) as one embodiment of the present invention. As shown in FIG. 60, identification is performed by computing the distances between a single nose pattern code given for identification and each of k nose pattern codes (nose pattern code_1, . . . , nose pattern code_k) stored in the DB. As previously described, each nose pattern code stored in the DB consists of the frequency transform code C and the masking code M, and the DB of pre-registered nose pattern codes may be constructed as a part of the image recognition unit.

From k nose pattern codes stored in the DB and a single nose pattern code given for identification, a total of k distances are computed, and these k distances may be denoted by D1, . . . , Dk. The values of D1, . . . , Dk may be sorted in a descending or ascending order. One or more candidate nose pattern codes can be selected, according to one of three predefined selection rules: (a) a rule selecting the nose pattern code that gives the minimum distance among all those that yield distances less than the given threshold, (b) a rule selecting all the nose pattern codes whose distance is less than the given threshold, and (c) a rule selecting a predefined number, say n, of nose pattern codes whose distance is within top n least distances.

Further technical details have been omitted to avoid redundancy.

Finally, it should be noted, that certain components of the present invention have been described as operating in combination, or combined into one, does not suggest that the invention is necessarily limited to such embodiments. In other words, within the scope of the present invention, such components may operate by selectively binding to one or all of the other components. Moreover, although each component may be implemented as an independent hardware, a part of or all of each component may be optionally combined to perform one or a combination of some or all functions of each component.

In addition, the functional programs, codes, and code segments for implementing the present invention may be easily construed by programmers skilled in the area relevant to the invention. Such a computer program may be saved onto a computer readable media to be read and executed by a computer, and possible storage devices include ROM, RAM, CD ROM, magnetic tapes, floppy disks, and optical data storage devices, and carrier wave.

Moreover, terms such as "to include," "to comprise" or "to have" as set forth above, unless specified otherwise, should not be interpreted to exclude other components, but rather that it may also include others.

All terms, including technical and scientific terms, unless defined otherwise, should be interpreted to mean the conventional definition. Other commonly used terms should be understood to match the contextual meaning relevant to the art.

The present invention relates to the apparatus and method of animal recognition using nose patterns. Specifically, it involves the use of a body stabilizer unit, image acquisition unit, and image recognition unit to obtain identifiable nose pattern images. The proposed method is physically and economically easy to implement and requires little expertise on the part of the operator; and as such, presents a very high potential for industrial applicability.

What is claimed is:

1. An animal recognition apparatus using nose patterns, comprising a body stabilizer unit to minimize movement and resistance in subject animals during nose pattern image capture and acquisition, wherein the body stabilizer unit comprises a posture stabilizer unit to hold the subject animals in place.

2. The animal recognition apparatus according to claim 1, wherein the body stabilizer unit further comprises a position adjuster unit to adjust height, stance width and horizontal balance settings of the posture stabilizer unit as per each subject animal's physical characteristics.

3. The animal recognition apparatus according to claim 2, wherein the position adjuster unit comprises one or more of a height adjuster unit, a stance width adjuster unit and a horizontal balance adjuster unit that levels the head position.

4. The animal recognition apparatus according to claim 3, wherein the height adjuster unit comprises a chin support height adjuster unit.

5. The animal recognition apparatus according to claim 4, wherein the chin support height adjuster unit comprises:
a base;
a connector subunit connecting the base and the chin support; and
a chin support height adjuster subunit for adjusting the height of the connector subunit.

6. The animal recognition apparatus according to claim 3 wherein the horizontal balance adjuster unit comprises a horizontal balance sensor with a display unit.

7. The animal recognition apparatus according to claim 6, wherein the horizontal balance sensor comprises one or more of gravity, gyro, and pressure sensors.

8. The animal recognition apparatus according to claim 3 wherein the stance width adjuster unit comprises a connector subunit for adjusting the distance between the forefeet and a length adjuster subunit for the connector subunit.

9. The animal recognition apparatus according to claim 8, wherein the connector subunit has a belt or a cable connecting the two forefeet.

10. The animal recognition apparatus according to claim 3, wherein the height adjuster unit connects an upper body stabilizer unit to a lower body stabilizer unit.

11. The animal recognition apparatus according to claim 10, wherein the height adjuster unit connecting the upper body stabilizer unit to the lower body stabilizer unit comprises a connector subunit and a length adjuster subunit.

12. The animal recognition apparatus according to claim 11, wherein the connector subunit has a belt or cable.

13. The animal recognition apparatus according to claim 2, wherein the body stabilizer unit with the posture stabilizer unit and the position adjuster unit is configured according to the size and morphology of each subject animal.

14. The animal recognition apparatus according to claim 1, wherein the posture stabilizer unit comprises an upper body stabilizer unit and a head stabilizer unit.

15. The animal recognition apparatus according to claim 14, wherein the upper body stabilizer unit comprises an upper body stabilizing brace subunit and an upper body stabilizing brace lock subunit.

16. The animal recognition apparatus according to claim 15, wherein the upper body stabilizing brace subunit comprises at least one of a cover, a belt and cables enwrapping a portion of the upper body.

17. The animal recognition apparatus according to claim 16, wherein the upper body stabilizing brace lock subunit comprises at least one of a manual lock subunit and an electronic lock subunit fixing the cover, belt or cables of the upper body stabilizing brace subunit.

18. The animal recognition apparatus according to claim 15, wherein the upper body stabilizing brace subunit is coupled with an upper body stabilizing brace pressure adjuster subunit that applies an appropriate amount of pressure while enwrapping the upper body of the subject animal.

19. The animal recognition apparatus according to claim 18, wherein the upper body stabilizing brace pressure adjuster subunit comprises an adjusting mechanism for volume or length of the upper body stabilizing brace subunit, or a pressure injector inflating the brace with some liquid or gas.

20. The animal recognition apparatus according to claim 14, wherein the head stabilizer unit comprises a chin support on which to position the head of the subject animal.

21. The animal recognition apparatus according to claim 20, wherein the chin support withstands a weight of the subject animal's head, is shaped and accompanied by necessary attachments to accommodate different sizes and shapes, and is made of wood, plastic, rubber, and/or metal.

22. The animal recognition apparatus according to claim 14, wherein the head stabilizer unit further comprises a stabilizing muzzle subunit holding the nose or mouth area, and a stabilizing muzzle lock subunit.

23. The animal recognition apparatus according to claim 22, wherein the stabilizing muzzle subunit comprises at least one of a cover, a belt and cables enwrapping a portion of the head.

24. The animal recognition apparatus according to claim 23, wherein the stabilizing muzzle lock subunit comprises at least one of a manual lock subunit and an electronic lock subunit fixing the cover, belt or cables of the stabilizing muzzle subunit.

25. The animal recognition apparatus according to claim 22, wherein the stabilizing muzzle subunit is coupled with a stabilizing muzzle pressure adjuster subunit that applies an appropriate amount of pressure while enwrapping the head of the subject animal.

26. The animal recognition apparatus according to claim 25, wherein the stabilizing muzzle pressure adjuster subunit comprises an adjusting mechanism for volume or length of the stabilizing muzzle subunit, or a pressure injector inflating the muzzle with some liquid or gas.

27. The animal recognition apparatus according to claim 14, wherein the head stabilizer unit further comprises a horizontal balance adjuster unit with left, right, up and down controls to level the head position.

28. The animal recognition apparatus according to claim 1, wherein the posture stabilizer unit further comprises a lower body stabilizer unit.

29. The animal recognition apparatus according to claim 28, wherein the lower body stabilizer unit comprises a lower body stabilizing brace subunit, and a lower body stabilizing brace lock subunit.

30. The animal recognition apparatus according to claim 29, wherein the lower body stabilizing brace subunit comprises at least one of a cover, a belt and cables enwrapping a portion of the lower body.

31. The animal recognition apparatus according to claim 29, wherein the lower body stabilizing brace lock subunit comprises at least one of a manual lock subunit and an electronic lock subunit fixing the cover, belt or cables of the lower body stabilizing brace subunit.

32. The animal recognition apparatus according to claim 29, wherein the lower body stabilizing brace subunit is coupled with a lower body stabilizing brace pressure adjuster subunit that applies an appropriate amount of pressure while enwrapping the lower body of the subject animal.

33. The animal recognition apparatus according to claim 32, wherein the lower body stabilizing brace pressure adjuster subunit comprises an adjusting mechanism for volume or length of the lower body stabilizing brace subunit, or a pressure injector inflating the brace with some liquid or gas.

34. The animal recognition apparatus according to claim 28, wherein the lower body stabilizer unit is coupled with a lower body stabilizer supporting subunit anchoring the stabilizer unit to a ground or work station.

35. The animal recognition apparatus according to claim 34, wherein the lower body stabilizer supporting subunit comprises:
a lower body supporting subunit anchoring the stabilizer unit to the ground or work station; and
a lower body supporter connector subunit connecting the lower body supporting subunit and the lower body stabilizer unit.

36. The animal recognition apparatus according to claim 35, wherein the lower body supporting subunit and the lower body supporter connector subunit have a hook form or other device to ensure a good hold of the lower body stabilizer unit depending on the subject animal species or breed; and are made of steel or other metals, durable synthetic fibers, rubber and/or fabric.

37. The animal recognition apparatus according to claim 28, wherein the lower body stabilizer unit further comprises a stance width adjuster unit to fit the forefeet of the subject animals of various species and sizes.

* * * * *